US008603758B2

(12) United States Patent
Acevedo-Duncan et al.

(10) Patent No.: US 8,603,758 B2
(45) Date of Patent: Dec. 10, 2013

(54) PROSTATE CARCINOGENESIS PREDICTOR

(75) Inventors: Mildred Acevedo-Duncan, Plant City, FL (US); Hla Y. Win, Tampa, FL (US); Raoul Salup, Tampa, FL (US)

(73) Assignees: University of South Florida, Tampa, FL (US); The United States of America as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 13/532,364

(22) Filed: Jun. 25, 2012

(65) Prior Publication Data
US 2012/0294932 A1 Nov. 22, 2012

Related U.S. Application Data

(62) Division of application No. 12/253,663, filed on Oct. 17, 2008, now abandoned.

(60) Provisional application No. 60/980,611, filed on Oct. 17, 2007.

(51) Int. Cl.
*C12Q 1/00* (2006.01)
*G01N 1/00* (2006.01)
*G01N 33/00* (2006.01)
*G01N 33/48* (2006.01)
*G01N 33/53* (2006.01)
*G01N 33/567* (2006.01)
*G01N 33/574* (2006.01)

(52) U.S. Cl.
USPC ............... 435/7.1; 435/4; 435/7.2; 435/7.21; 435/7.23; 435/7.92; 436/64; 436/86; 436/174; 436/501; 436/536

(58) Field of Classification Search
USPC ............... 435/4, 7.1, 7.2, 7.21, 7.23, 7.92; 436/64, 86, 174, 501, 536
See application file for complete search history.

(56) References Cited

U.S. PATENT DOCUMENTS

2007/0212721 A1* 9/2007 Fischer et al. ................ 435/6

OTHER PUBLICATIONS

Cornford et al. Protein kinase c isoenzyme patterns characteristically modulated in early prostate cancer. American Journal of Pathology 154(1): 137-144, Jan. 1999.*

* cited by examiner

*Primary Examiner* — Alana Harris Dent
(74) *Attorney, Agent, or Firm* — Saliwanchik Lloyd & Eisenschenk

(57) ABSTRACT

A method of detecting prostate tumorigenesis in a subject, the method including the steps of (a) obtaining a sample from the prostate of the human subject, (b) detecting quantitatively or semi-quantitatively in the sample a level of expression for PKC-ι and (c) comparing the expression level in (b) to a level of expression in a normal control, wherein overexpression of PKC-ι, with respect to the control, indicates the presence of prostate cancer in the subject. The present invention is based upon the discovery that PKC-ι levels are elevated during prostate tumorigenesis. Furthermore, the proliferation rate of the tumor correlates with the level of PKC-ι. The invention also provides methods of treating prostate cancer by administering to the subject a compound that inhibits the expression of PKC-ι. The compound can be a small interfering RNA (siRNA) molecule.

12 Claims, 10 Drawing Sheets

PROSTATE CARCINOGENESIS PREDICTOR

CROSS-REFERENCE TO RELATED APPLICATIONS

This application is a divisional of U.S. patent application Ser. No. 12/253,663, filed Oct. 17, 2008, which claims the benefit of U.S. provisional application Ser. No. 60/980,611, filed Oct. 17, 2007, which are herein incorporated by reference in their entirety.

FIELD OF INVENTION

This invention relates to detection and treatment of prostate cancer. More specifically, the invention relates to use of protein kinase C-iota (PKC-ι) in the detection of prostate cancer and methods of inhibiting the expression and activity of protein kinase C-iota as a treatment for prostate cancer.

BRIEF SUMMARY

As described herein, the invention consists of a means and product to detect protein kinase C-iota (PKC-ι) levels in prostate glands to identify prostate carcinogenesis. Prostate cancers are highly lethal tumors and are the second most prevalent type of cancer (following skin cancer) among men in the United States. Approximately one third of men diagnosed with cancer each year will have prostate cancer. Despite significant educational efforts, improved diagnostic techniques, and rigorous therapies, prostate cancer control remains static. To address this health issue, the presence of PKC-ι in normal prostate tissue and prostate cancer tissue was investigated, to establish if PKC-ι could be used as a predictor of carcinogenesis. Western blots probing for PKC-ι were performed on 7 normal prostate biopsies, 2 prostate intraepithelial neoplasia and 14 prostate cancers. Results demonstrated minimal or no detection of PKC-ι the in normal prostate tissue. In comparison, PKC-ι was robustly present in prostate intraepithelial neoplasia (PIN). Similarly, PKC-ι was present in all prostate cancer biopsies. The increase in PKC-ι in prostate cancer biopsies was 100 fold compared to normal prostate tissue (P=0.00048). These results indicate that detection of PKC-ι is a predictor of prostate carcinogenesis and of patients that could benefit from anti-PKC-ι therapy.

Also described herein, the subject invention comprises a method of treatment for cancer cells directed at suppressing PKC-ι. Treatment of RWPE-1 (transformed non-malignant prostate cells) cells with PKC-ι short interference RNA (siRNA) reduced cell proliferation, and arrested cells at $G_2/M$ phase of the cell cycle (55%) compared to control siRNA at 24 h. PKC-ι siRNA decreased cell cycle kinase phosphor-cdk2 (p-cdk2; Ther160) phosphorylation in RWPE-1 normal prostate cells. In comparison, both LNCaP and DU-145 carcinoma cells undergo apoptosis when treated with PKC-ι siRNA. In DU-145 cells, PKC-ι siRNA treatment results in time-dependent cell cycle arrest at $G_0/G_1$ phase (32% at 24 h and 23% at 48 h). Additionally, in DU-145 prostate cancer cells, PKC-ι siRNA provokes cytochrome C release from mitochondria into the cytoplasm leading to Caspase activation followed by poly(ADP-ribose) polymerase (PARP) cleavage and apoptosis. These results indicate that PKC-ι is a relevant target for the treatment of prostate cancer.

BRIEF DESCRIPTION OF THE DRAWINGS

For a fuller understanding of the invention, reference should be made to the following detailed description, taken in connection with the accompanying drawings, in which.

BRIEF DESCRIPTION OF THE SEQUENCES

Figure 1:
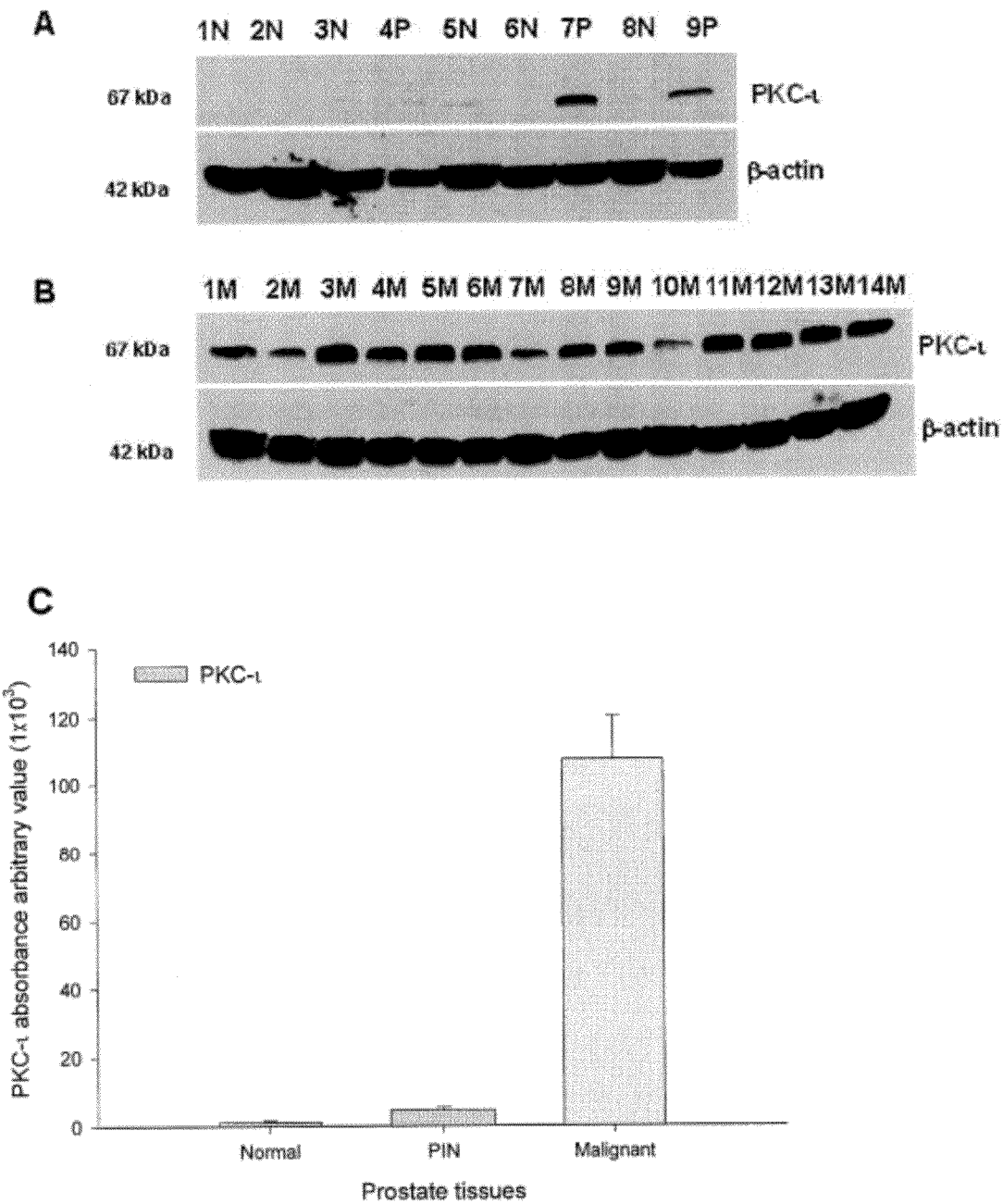
FIG. 1 is a protein blot for protein kinase-iota (PKC-ι) levels in normal prostate (A), malignant tumor prostate (B), and a graph of the quantified PKC-ι protein levels from normal prostate, prostate intraepithelial neoplasia, and malignant prostate tumor tissue.

```
                                    SEQ ID NO: 1
5'-CAAGCCAAGCGUUUCAACA-3'
is a single strand of PKC-ι siRNA;

SEQ ID NO: 2
5'-UGUUGAAACGCUUGGCUUG-3'
is a single strand of PKC-ι siRNA;

SEQ ID NO: 3
739 5'-GGAACGAUUGGGUUGUCAU-3'
is a single strand of PKC-ι siRNA;

SEQ ID NO: 4
5'-AUGACAACCCAAUCGUUUCC-3'
is a single strand of PKC-ι siRNA;

SEQ ID NO: 5
2137 5'-CCCAAUAUCUUCUCUUGUA-3'
is a single strand of PKC-ι siRNA;
```

-continued

```
                                      SEQ ID NO: 6
5'-UACAAGAGAAGAUAUUGGG3'
is a single strand of PKC-ι siRNA;

SEQ ID NO: 7
5'-AAGACGACACAUGUCUCUCACCCUGUCUC-3'
is a single strand of PKC-ζ siRNA;

SEQ ID NO: 8
5'-AUACAUUUCU ACAGCUAGC-3'
is a single strand of PKC-ζ siRNA;

SEQ ID NO: 9
5'-GAGACAGGGUGAGAGACAUGUGUCGUCUU-3'
is a single strand of PKC-ζ siRNA;

SEQ ID NO: 10
5'-GCUAGC UGUAGAAAUGUAU-3'
is a single strand of PKC-ζ siRNA;

SEQ ID NO: 11
5'-UCAUAAAUCAGUUUCUCAC-3'
is a single strand of PKC-δ siRNA;

SEQ ID NO: 12
5'-AUGACAAAGAAAUUCUGAC-3'
is a single strand of PKC-δ siRNA;

SEQ ID NO: 13
GUGAGAAACUGAUUUAUGA-3'
is a single strand of PKC-δ siRNA;
and

SEQ ID NO: 14
5'-GUCAGAAUUUCUUUGUCAU-3'
is a single strand of PKC-δ siRNA.
```

DETAILED DESCRIPTION

Prostate Tissue

Besides skin cancer, prostate cancer is the most common type of cancer among men in the United States. Approximately one third of men diagnosed with cancer each year will have prostrate cancer. Despite significant educational efforts, improved diagnostic techniques, and rigorous therapies, prostate cancer control remains static. Certain prostate cancers are highly lethal tumors due to the emergence of therapy-resistant prostate cancer cells. Protein kinase C (PKC) may be involved in several cell signaling pathways (cell survival including repair of radiation damage and cell cycle (Hallahan et al., 1992)), thus its inhibition may result in radiosensitization. However, specific PKC isozymes responsible for prostate cancer cell proliferation and survival are unknown. PKC is a family of fourteen known isozymes which are found in varying ratios in the cytoplasmic and membrane fraction of cells depending on the type of tissue and its physiological state (Nishizuka, 1992). PKC isozymes can be classified into three groups. Group I includes $Ca^{2+}$ dependent isozymes: cPKC-α, cPKC-βI, cPKC-βII, and cPKC-γ. Isozymes in group II (nPKC-ε, nPKC-δ, nPKC-η and PKC-θ) are $Ca^{2+}$ independent. Group III includes the atypical PKCs (aPKC-ι (Selbie et al., 1993), aPKC-ζ, aPKC-ζII (Hirai et al., 2003) aPKC-μ (protein kinase D) and aPKC-ν) (Hayashi et al., 1999)) which are insensitive to both diacylglycerol and calcium and neither bind to nor are activated by phorbol esters. PKC regulates cellular functions, metabolism and proliferation by phosphorylating proteins in response to transmembrane signals from hormones, growth factors, neuro-transmitters, and pharmacological agents. Activation of PKC by various agonists (including radiation) results in altered transcription of a considerable number of genes. Some PKC isozymes are transiently translocated from the cytosol to a membrane structure. Membrane association leads to binding alterations in PKC's regulatory subunit (phospholipid-/diacylglycerol/phorbol ester) and its 50 KD catalytic domain (ATP/substrate). For PKCs to be activated, phosphoinositide-dependent kinase (PDK-1; (Dutil et al., 1998)) docks on the carboxyl terminus of unphosphorylated PKC (Edwards et al., 1999), PDK-1 phosphorylates PKCs on the activation loop, and upon release of PDK-1, the carboxyl terminus is unmasked and allows autophosphorylation (Dutil et al., 1998; Edwards et al., 1999; Keranen et al., 1995). This sequence of phosphorylation events is required before PKCs are able to respond to cofactor second messengers (phosphatidylserine/ diacylglycerol (Dutil et al., 1998; Edwards et al., 1999)). Proteolytic degradation of membrane PKC leads to its down-regulation. PKC is the major receptor for tumor promoting phorbol esters, but the extent of PKC involvement in cellular malignancy is not clearly defined. Various studies indicate that increased tumorigenicity results from dysregulation of PKC activity, or changes in PKC concentration, or both (Persons et al., 1988; Housey et al., 1988; Kamata et al., 1987; Weyman et al., 1988; Mizuguhi et al., 1988).

PKC isozymes have been implicated in carcinogenesis for some time but only recently did we attain modest information about the functional significance of these enzymes in human cancers. PKC isoenzymes—α, β, δ, ε, γ, ι, ζ, μ, and η are expressed in both normal prostate and tumor tissues (Cornfor et al., 1999). LNCaP cells are a widely studied model for prostate cancer. Early studies showed that activation of PKC-α with 12-O-tetradecanoylphorbol-13-acetate (TPA) induced apoptosis in LNCaP cells (Powell et al., 1996). However, androgen-independent prostate PC-3 and DU-145 cells are insensitive to TPA (Powell et al., 1996; Gonzalex-Guerrico et al., 2005; Garcia-Bermejo et al., 2002.

There is an expanding body of knowledge regarding the status of atypical PKC-ι which does not contain a $Ca^{2+}$-binding region, has one zinc finger-like motif and is the human homolog of the mouse PKC-λ (Diaz-Meco et al., 1996). Elder et al. provided evidence for the role of PKC-ι in cell proliferation by showing that increased PKC-ι protein levels were associated with increased cyclin E protein expression and proliferation of ovarian cancers. In nonserous ovarian cancers they demonstrated that increased PKC-ι protein levels markedly decreased overall survival. Work from Field's laboratory indicated that PKC-ι is critical for non-small cell lung cancer proliferation in-vivo by activation of Rac1/Pak/Mek1,2/Erk1,2 signaling pathway which has been implicated in tumor cell proliferation and concluded that PKC-ι is an oncogene in human non-small cell lung cancer (Regala et al., 2005; Regala et al., 2005b). Additional powerful evidence of PKC-ι's importance in cellular malignancy includes its exclusive association with transformed phenotype of human melanomas in-vivo and in-vitro (Selzer et al., 2002), it's overexpression in human non-small lung cancer cell lines (Regala et al., 2005), cholangiocarcinoma (Li et al., 2008), and tumors (Regala et al., 2005b) and it's presence in the transformed growth of human lung adenocarcinoma A549 cell line in-vitro and tumorigenicity in-vivo (Regala et al., 2005). Work from our laboratory also depicts PKC-ι's exclusive association with the transformed phenotype of gliomas, benign and malignant meningiomas (Patel et al., 2008). Studies have shown that PKC-ι protects cells against drug induced apoptosis (Wu et al., 2004; Flescher and Rotem 2002). Murray and Fields stably transfected K562 leukemia cells with expression plasmids containing cDNA for human PKC-ι in the sense and antisense orientation (Murray and Fields, 1997). They found that overexpression or inhibition has no significant effect on the proliferation activity of K562 cells. However, overexpression of PKC-ι led to increased resistance to okadaic acid and taxol-induced apoptosis, whereas inhibition of PKC-ι expression sensitized the cells to okadaic acid-induced apoptosis. Thus, Murray and Fields demonstrated a potential role for PKC-ι in leukemia cell survival (Murray and Fields, 1997). Other lines of evidence comes from Xie et al., who demonstrated that overexpression of PKC-ι increased resistance of PC12 neural cells to apoptosis induced by amyloid β-peptide by attenuating the levels of oxidative stress and intracellular calcium (Xie et al., 2000). Xie et al. suggested that PKC-ι prevents apoptosis by maintaining ion homeostasis and mitochondrial function. In this study Western blot analysis demonstrated that PKC-ι is overexpressed in some PIN and in malignant prostate tissue but not in BPH tissues. Immunohistochemistry results demonstrated greater PKC-ι staining intensity in the adenocarcinoma glands compared to benign glands and glands with HGPIN. The benign glands showed similar weak staining of PKC-ι in samples obtained from patients with and without prostatic adenocarcinoma. The stromal cells depicted weak to moderate staining of PKC-ι in samples with and without adenocarcinoma. These results indicate that detection of PKC-ι could be used as a predictor of prostate carcinogenesis and of patients that could benefit from anti-PKC-ι therapy.

In PC-3 and DU-145 cells, epidermal growth factor (EGF) signals to PKC-α and PKC-α is associated with growth inhibition (Stewart and O'Brian, 2005; Shih et al., 2004; Lamm et al., 1997). In addition, the PKC-α gene is part of chromosome 17q, and is commonly amplified in prostate cancers (Oxley et al., 2002; Lahn et al., 2004). Hence, a specific inhibitor, aprinocarsen, a phosphorothioate antisense oligonucleotides, has been developed to block PKC-α expression (Dean et al., 1994; Davies et al., 2003). Besides classical PKC-α, novel PKC-δ overexpressed in LNCaP cells provoke phorbol ester-induced apoptosis. However, lack of proteolytic cleavage and caspase-3 inactivation suggested that an allosteric activation of PKC-δ is sufficient to induce apoptosis in LNCaP cells (Fujii et al., 2000). In PC-3 and DU-145 cells, PKC-δ is involved in cell motility and invasion of prostate tumor cells (Kharait et al., 2006; Rosenberg and David 2006). Moreover, PKC-ε along with Akt promotes matrix adhesions containing actin filaments and βI intergins in recurrent prostate cancer cells (Wu et al., 2004). PKC-ε also regulates P-glycoprotein (P-gp) expression, which is responsible for drug resistance in LNCaP prostate carcinoma cells (Flescher and Rotem 2002). In DU-145 cells the downregulation of PKC-ε prevented apoptosis (Rusnak and Lazo 1996). Hence, PKC-ε is being targeted for prostate therapy.

PKC-μ and PKC-ζ-mTOR (mammalian target of rapamycin)/p70 S6 kinase pathway is associated with progression of androgen-dependent prostate cancer to androgen-independent prostate cancer (Rao et al., 2003; Jaggi et al., 2003; Inoue et al., 2006). However, this linkage remains to be established. Nonetheless, understanding PKC isoforms in prostate cancer may contribute to possible therapeutic strategies. We have investigated the content of PKC-ι in BPH, PIN and malignant prostate biopsies by Western blotting and immunohistochemistry. Our findings show for the first time that the PKC-ι protein levels are increased in PIN and malignant prostate compared to BPH.

In one embodiment of the invention, a sandwich enzyme-linked immunosorbent assay (ELISA) can be developed using monoclonal antibodies specific for PKC-ι. This assay can be used to detect the presence of PKC-ι in suspect tissues of patients.

In another embodiment of the invention, an ELISA of the subject invention for detection of PKC-ι is simple to use. It has high degrees of specificity and sensitivity, low intra- and inter-assay coefficients of variation, and uses chemicals that pose a low risk to human health and are easily disposed of. Thus it has a low cost to benefit ratio. It is flexible in its sample handling and can be used to process either low or high numbers of samples.

It makes available for the first time the ability to measure human PKC-ι protein expression in a large number of samples at a low cost and with simplicity and accuracy.

The methods of the invention can be carried out on a solid support. The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. PKC-ι can be detected in a sample in vivo or in vitro (ex vivo). When, according to an embodiment of the invention, the amount of PKC-ι in a sample is to be determined without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

A contacting step in the assay (method) of the invention can involve contacting, combining, or mixing the biological sample and the solid support, such as a reaction vessel, microvessel, tube, microtube, well, multi-well plate, or other solid support.

Samples and/or PKC-ι-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, PKC-ι-specific binding agents may be immobilized on the solid support.

In one aspect, the present invention includes kits comprising the required elements for detecting PKC-ι. Preferably, the kits comprise a container for collecting a sample, such as biological fluid from a patient, and an agent for detecting the presence of PKC-ι in the fluid. The components of the kits can be packaged either in aqueous medium or in lyophilized form.

The methods of the invention can be carried out using a diagnostic kit for qualitatively or quantitatively detecting PKC-ι in a sample. By way of example, the kit can contain binding agents (e.g., antibodies) specific for PKC-ι, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit.

As indicated above, kits of the invention include reagents for use in the methods described herein, in one or more containers. The kits may include primers, specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample.

Kits of the invention can be provided in suitable packaging. As used herein, "packaging" refers to a solid matrix or material customarily used in a system and capable of holding within fixed limits one or more of the reagent components for use in a method of the present invention. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe, primer, molecular beacon, specific internal control, etc. Preferably, the solid matrix is a planar material such as the side of a microtiter well or the side of a dipstick. In certain embodiments, the kit includes a microtiter tray with two or more wells and with reagents including primers, probes, specific internal controls, and/or molecular beacons in the wells.

Kits of the invention may optionally include a set of instructions in printed or electronic (e.g., magnetic or optical disk) form, relating information regarding the components of the kits and/or how to make various determinations (e.g., PKC-ι levels, comparison to control standards, etc.). The kit may also be commercialized as part of a larger package that includes instrumentation for measuring other biochemical components.

As used herein, the term "ELISA" includes an enzyme-linked immunosorbent assay that employs an antibody or antigen bound to a solid phase and an enzyme-antigen or enzyme-antibody conjugate to detect and quantify the amount of an antigen (e.g., PKC-ι) or antibody present in a sample. A description of the ELISA technique is found in Chapter 22 of the $4^{th}$ Edition of Basic and Clinical Immunology by D. P. Sites et al., 1982, published by Lange Medical Publications of Los Altos, Calif. and in U.S. Pat. Nos. 3,654,090; 3,850,752; and 4,016,043, the disclosures of which are herein incorporated by reference. ELISA is an assay that can be used to quantitate the amount of antigen, proteins, or other molecules of interest in a sample. In particular, ELISA can be carried out by attaching on a solid support (e.g., polyvinyl-chloride) an antibody specific for an antigen or protein of interest. Cell extract or other sample of interest such as urine or blood can be added for formation of an antibody-antigen complex, and the extra, unbound sample is washed away. An enzyme-linked antibody, specific for a different site on the antigen is added. The support is washed to remove the unbound enzyme-linked second antibody. The enzyme-linked antibody can include, but is not limited to, alkaline phosphatase. The enzyme on the second antibody can convert an added colorless substrate into a colored product or can convert a non-fluorescent substrate into a fluorescent product. The ELISA-based assay method provided herein can be conducted in a single chamber or on an array of chambers and can be adapted for automated processes.

In some embodiments, the antibodies can be labeled with pairs of FRET dyes, bioluminescence resonance energy transfer (BRET) protein, fluorescent dye-quencher dye combinations, and beta gal complementation assays protein fragments. The antibodies may participate in FRET, BRET, and fluorescence quenching or beta-gal complementation to generate fluorescence, colorimetric or enhanced chemiluminescence (ECL) signals, for example.

These methods are routinely employed in the detection of antigen-specific antibody responses, and are well described in general immunology text books such as Immunology by Ivan Roitt, Jonathan Brostoff and David Male (London: Mosby, c1998. 5th ed. and Immunobiology: Immune System in Health and Disease/Charles A. Janeway and Paul Travers. Oxford: Blackwell Sci. Pub., 1994), the contents of which are herein incorporated by reference.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), ultrasound, CT, and MRI, or by needle aspirations. The use of these latter techniques is more common in early detection. Molecular and phenotypic analysis of cancer cells within a tissue will usually confirm if the cancer is endogenous to the tissue or if the lesion is due to metastasis from another site.

A "sample" (biological sample) can be any composition of matter of interest from a human or non-human subject, in any physical state (e.g., solid, liquid, semi-solid, vapor) and of any complexity. The sample can be any composition reasonably suspected of containing PKC-ι that can be analyzed by the methods, devices, and kits of the invention. Preferably, the sample is a fluid (biological fluid). Samples preferably include human samples. The sample may be contained within a test tube, culture vessel, multi-well plate, or any other container or supporting substrate. The sample can be, for example, a cell culture or human tissue. Fluid homogenates of cellular tissues are biological fluids that may contain PKC-ι for detection by the invention. Others are fluid tissues, for example, blood.

The "complexity" of a sample refers to the relative number of different molecular species that are present in the sample.

The terms "body fluid" and "bodily fluid", as used herein, refer to a composition obtained from a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions or mixtures containing homogenized solid material, such as feces, tissues, and biopsy samples.

The term "ex vivo," as used herein, refers to an environment outside of a subject. Accordingly, a sample of bodily fluid collected from a subject is an ex vivo sample of bodily fluid as contemplated by the subject invention. In-dwelling embodiments of the method and device of the invention obtain samples in vivo.

As used herein, the term "conjugate" refers to a compound comprising two or more molecules bound together, optionally through a linking group, to form a single structure. The binding can be made by a direct connection (e.g., a chemical bond) between the molecules or by use of a linking group.

As used herein, the terms solid "support", "substrate", and "surface" refer to a solid phase which is a porous or non-porous water insoluble material that can have any of a number of shapes, such as strip, rod, particle, beads, or multi-welled plate. In some embodiments, the support has a fixed organizational support matrix that preferably functions as an organization matrix, such as a microtiter tray. Solid support materials include, but are not limited to, cellulose, polysaccharide such as Sephadex, glass, polyacryloylmorpholide, silica, controlled pore glass (CPG), polystyrene, polystyrene/latex, polyethylene such as ultra high molecular weight polyethylene (UPE), polyamide, polyvinylidine fluoride (PVDF), polytetrafluoroethylene (PTFE; TEFLON), carboxyl modified teflon, nylon, nitrocellulose, and metals and alloys such as gold, platinum and palladium. The solid support can be biological, non-biological, organic, inorganic, or a combination of any of these, existing as particles, strands, precipitates, gels, sheets, pads, cards, strips, dipsticks, test strips, tubing, spheres, containers, capillaries, pads, slices, films, plates, slides, etc., depending upon the particular application. Preferably, the solid support is planar in shape, to facilitate contact with a biological sample such as urine, whole blood, plasma, serum, peritoneal fluid, or ascites fluid. Other suitable solid support materials will be readily apparent to those of skill in the art. The solid support can be a membrane, with or without a backing (e.g., polystyrene or polyester card backing), such as those available from Millipore Corp. (Bedford, Mass.), e.g., Hi-Flow™ Plus membrane cards. The surface of the solid support may contain reactive groups, such as carboxyl, amino, hydroxyl, thiol, or the like for the attachment of nucleic acids, proteins, etc. Surfaces on the solid support will sometimes, though not always, be composed of the same material as the support. Thus, the surface can be composed of any of a wide variety of materials, such as polymers, plastics, resins, polysaccharides, silica or silica-based materials, carbon, metals, inorganic glasses, membranes, or any of the aforementioned support materials (e.g., as a layer or coating).

As used herein, the terms "label" and "tag" refer to substances that may confer a detectable signal, and include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, isothiocynate, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc., which may be further labeled with a dye, catalyst or other detectable group.

As used herein, the term "receptor" and "receptor protein" are used herein to indicate a biologically active proteinaceous molecule that specifically binds to (or with) other molecules such as PKC-ι.

As used herein, the term "ligand" refers to a molecule that contains a structural portion that is bound by specific interaction with a particular receptor protein.

As used herein, the term "antibody" refers to immunoglobulin molecules and immunologically active portions (fragments) of immunoglobulin molecules, i.e., molecules that contain an antibody combining site or paratope. The term is inclusive of monoclonal antibodies and polyclonal antibodies.

As used here, the terms "monoclonal antibody" or "monoclonal antibody composition" refer to an antibody molecule that contains only one species of antibody combining site capable of immunoreacting with a particular antigen. A monoclonal antibody composition thus typically displays a single binding affinity for any antigen with which it immunoreacts. A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature*, 1975, 256:495-497, the disclosure of which is herein incorporated by reference. An exemplary hybridoma technology is described by Niman et al., *Proc. Natl. Acad. Sci. U.S.A.*, 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoire as described by Sasatry, et al., *Proc. Natl. Acad. Sci. USA*, 1989, 86:5728-5732; and Huse et al., *Science*, 1981, 246:1275-1281. The references cited are hereby incorporated herein by reference.

As used herein, a semi-permeable membrane refers to a bio-compatible material which is impermeable to liquids and capable of allowing the transfer of gases through it. Such gases include, but are not limited to, oxygen, water vapor, and carbon dioxide. Semi-permeable membranes are an example of a material that can be used to form a least a portion of an enclosure defining a flow chamber cavity. The semi-permeable membrane may be capable of excluding microbial contamination (e.g., the pore size is characteristically small enough to exclude the passage of microbes that can contaminate the analyte, such as cells). In a particular aspect, a semi-permeable membrane can have an optical transparency and clarity sufficient for permitting observation of an analyte, such as cells, for color, growth, size, morphology, imaging, and other purposes well known in the art.

As used herein, the term "bind" refers to any physical attachment or close association, which may be permanent or temporary. The binding can result from hydrogen bonding, hydrophobic forces, van der Waals forces, covalent, or ionic bonding, for example.

As used herein, the term "diagnosis" or "diagnostic" generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

The subject invention also pertains to novel therapeutic agents (including but not limited to monoclonal antibodies and siRNA) and the use of these agents in, for example, treatment of prostate cancer.

As used herein, the term "particle" includes insoluble materials of any configuration, including, but not limited to, spherical, thread-like, brush-like, and irregular shapes. Particles can be porous with regular or random channels inside. Particles can be magnetic. Examples of particles include, but are not limited to, silica, cellulose, Sepharose beads, polystyrene (solid, porous, derivatized) beads, controlled-pore glass, gel beads, magnetic beads, sols, biological cells, subcellular particles, microorganisms (protozoans, bacteria, yeast, viruses, and other infectious agents), micelles, liposomes, cyclodextrins, and other insoluble materials.

A "coding sequence" or "coding region" is a polynucleotide sequence that is transcribed into mRNA and/or translated into a polypeptide. For example, a coding sequence may encode a polypeptide of interest. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

The terms "operably-linked" or "operatively-linked" are used herein interchangeably to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" is used to refer to any molecule (e.g., nucleic acid, plasmid, or virus) used to transfer coding information (e.g., a polynucleotide of the invention) to a host cell. The terms "expression vector" and "transcription vector" are used interchangeably to refer to a vector that is suitable for use in a host cell (e.g., a subject's cell) and contains nucleic acid sequences that direct and/or control the expression of exogenous nucleic acid sequences. Expression includes, but is not limited to, processes such as transcription, translation, and RNA splicing, if introns are present.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as PKC-ι.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., PKC-ι mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

The term "dominant negative mutant" is art-recognized and refers to the mutant form of a wild-type protein that interferes with the function of the wild-type protein (e.g., by interacting with the wild-type protein). Thus, overexpression of the dominant negative mutant can be expected to interfere with the function of the wild-type version of the protein. As used herein, the term "mismatch" refers to a basepair consisting of noncomplementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines, in an organism.

The methods of the invention may include further steps. In some embodiments, a subject with the relevant condition or disease (e.g., prostate cancer) is identified or a patient at risk for the condition or disease is identified prior to administration of the PKC-ι inhibitor. A patient may be someone who has not been diagnosed with the disease or condition (diagnosis, prognosis, and/or staging) or someone diagnosed with the disease or condition (diagnosis, prognosis, monitoring, and/or staging), including someone treated for the disease or condition (prognosis, staging, and/or monitoring). Alternatively, the person may not have been diagnosed with the disease or condition but suspected of having the disease or condition based either on patient history or family history, or the exhibition or observation of characteristic symptoms.

As used herein, an "effective amount" of a PKC-ι inhibitor (such as an interfering RNA, an antisense oligonucleotide, or a ribozyme, which selectively interferes with expression of PKC-ι) is that amount effective to bring about the physiological changes desired in the cells to which the PKC-ι inhibitor is administered in vitro (e.g., ex vivo) or in vivo. The term "therapeutically effective amount" as used herein, means that amount of PKC-ι inhibitor alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. Preferably, suppression of PKC-ι function (e.g., by reduction of PKC-ι expression) results in tumor shrinkage or increased sensitivity to chemotherapy.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Reduction (suppression) of expression results in a decrease of PKC-ι mRNA and/or protein. For example, in a given cell, the suppression of PKC-ι mRNA by administration of a PKC-ι inhibitor that reduces PKC-ι function by reducing PKC-ι expression (such as interfering RNA, antisense oligonucleotide, or ribozyme) results in a decrease in the quantity of PKC-ιmRNA relative to an untreated cell. Suppression may be partial. Preferred degrees of suppression are at least 50%, more preferably one of at least 60%, 70%, 80%, 85%, or 90%. A level of suppression between 90% and 100% is generally considered a "silencing" of expression.

PKC-ι gene expression can be determined before and/or after introduction of the PKC-ιinhibitor in vitro or in vivo. Reduction in PKC-ι gene expression can be detected at either the protein or mRNA level. Protein expression analysis can be performed by Western blotting, immunofluorescence, or flow cytometry and cell sorting (FACS). Reduction in PKC-ι gene expression can be detected at the mRNA level by real-time RT-PCR, microarray analysis, or Northern blotting, for example. Preferably, all expression data is compared with levels of a "house keeping" gene to normalize for variable amounts of RNA in different samples.

In one embodiment of the invention, monoclonal antibodies specific for PKC-ι can be used as a delivery vehicle for drug or toxin. Drug or toxin can be conjugated to the antibodies using a biochemical approach. Monoclonal antibodies specific for the amino-terminus of PKC-ιcan be used as a delivery vehicle for drug or toxin. This enables the transport of drug or toxin to tumor cells with high expression of PKC-ι.

In a further embodiment of the invention, an anti-PKC-ι, or PKC-ι antagonist, antibody is used to inhibit the symptoms of a cancer overexpressing PKC-ι. The PKC-ι antagonist for use in treatment inhibits the activity of the overexpressed PKC-ι protein.

The terms "treatment" and "therapy" are used interchangeably herein, and as used herein include both prophylactic and responsive treatment, can be either acute short-term or chronic long-term, and denote the inhibition or amelioration of prostate cancer in a patient. "Patient" includes animals, including humans. The term "therapeutically effective" means that the amount of therapeutic agent (anti-PKC-ι monoclonal antibody, PKC-L-directed siRNA used is of sufficient quantity to inhibit or ameliorate the symptoms of prostate cancer.

In one embodiment of the method of the invention, the detection comprises: (a) contacting the biological sample with a binding agent that binds PKC-ι protein to form a complex; (b) detecting the complex; and (c) correlating the detected complex to the amount of PKC-ι protein in the sample, wherein the presence of elevated PKC-ι protein is indicative of cancer. In a specific embodiment, the detecting of (b) further comprises linking or incorporating a label onto the agent, or using ELISA-based immunoenzymatic detection.

Optionally, the methods of the invention further comprise detecting a biomarker of cancer in the same biological sample or a different biological sample obtained from the subject, before, during, or after said detecting of PKC-ι. In one embodiment, the biomarker of cancer is a biomarker of prostate cancer.

In some embodiments, the subject is suffering from cancer, such as prostate cancer, and the detecting is performed at several time points at intervals, as part of a monitoring of the subject before, during, or after the treatment of the cancer.

Optionally, the methods of the invention further comprise comparing the level of PKC-ι in the biological sample with the level of PKC-ι present in a normal control sample, wherein a higher level of PKC-ι in the biological sample as compared to the level in the normal control sample is indicative of cancer such as prostate cancer.

In some embodiments, the subject exhibits no symptoms of cancer at the time the detecting of PKC-ι is carried out. In other embodiments, the subject exhibits one or more symptoms of cancer at the time the detecting of PKC-ι is carried out.

In another embodiment, the invention includes a method for prognostic evaluation of a subject having, or suspected of having, cancer, comprising: a) determining the level of PKC-ι in a biological sample obtained from the subject, such as urine, blood, or ascites fluid; b) comparing the level determined in step (a) to a range of PKC-ι known to be present in a biological sample obtained from a normal subject that does not have cancer; and c) determining the prognosis of the subject based on the comparison of step (b), wherein a high level of PKC-ι in step (a) indicates an aggressive form of cancer and, therefore, a poor prognosis.

The terms "detecting" or "detect" include assaying or otherwise establishing the presence or absence of the target PKC-ι (PKC-ι encoding nucleic acid sequence or PKC-ι gene product (polypeptide)), subunits thereof, or combinations of agent bound targets, and the like, or assaying for, interrogating, ascertaining, establishing, or otherwise determining one or more factual characteristics of prostate cancer, metastasis, stage, or similar conditions. The term encompasses diagnostic, prognostic, and monitoring applications for PKC-ι and other cancer biomarkers. The term encompasses quantitative, semi-quantitative, and qualitative detection methodologies. In embodiments of the invention involving detection of PKC-ι protein (as opposed to nucleic acid molecules encoding PKC-ι protein), the detection method is preferably an ELISA-based method. Preferably, in the various embodiments of the invention, the detection method provides an output (i.e., readout or signal) with information concerning the presence, absence, or amount of PKC-ι in a sample from a subject. For example, the output may be qualitative (e.g., "positive" or "negative"), or quantitative (e.g., a concentration such as nanograms per milliliter).

In an embodiment, the invention relates to a method for detecting cancer in a subject by quantitating PKC-ι protein or encoding nucleic acids (DNA or RNA) in a biological sample such as urine from the subject, comprising (a) contacting (reacting) the biological sample with an antibody specific for PKC-ι which is directly or indirectly labeled with a detectable substance; and (b) detecting the detectable substance.

In an embodiment, the invention relates to a method for diagnosing and/or monitoring cancer in a subject by quantitating PKC-ι in a biological sample, such as urine or blood, from the subject, comprising (a) reacting the biological sample with an antibody specific for PKC-ι which is directly or indirectly labeled with a delectable substance; and (b) detecting the detectable substance.

Embodiments of the methods of the invention involve (a) contacting a biological sample from a subject with an antibody specific for PKC-ι which is directly or indirectly labeled with an enzyme; (b) adding a substrate for the enzyme wherein the substrate is selected so that the substrate, or a reaction product of the enzyme and substrate, forms fluorescent complexes; (c) quantitating PKC-ι in the sample by measuring fluorescence of the fluorescent complexes; and (d) comparing the quantitated levels to that of a standard.

A preferred embodiment of the invention comprises the following steps:

(a) incubating a biological sample with a first antibody specific for PKC-ι which is directly or indirectly labeled with a detectable substance, and a second antibody specific for PKC-ι which is immobilized;

(b) separating the first antibody from the second antibody to provide a first antibody phase and a second antibody phase;

(c) detecting the detectable substance in the first or second antibody phase thereby quantitating PKC-ι in the biological sample; and (d) comparing the quantitated PKC-ι with a standard.

A standard used in a method of the invention may correspond to PKC-ι levels obtained for samples from healthy control subjects, from subjects with benign disease (e.g., benign prostate disease), subjects with early stage prostate cancer, or from other samples of the subject. Increased levels of PKC-ι as compared to the standard may be indicative of cancer, such as early or late stage prostate cancer.

The invention also contemplates using the methods, devices, and kits described herein in conjunction with one or more additional markers ("biomarkers") for cancer. Therefore, the invention contemplates a method for analyzing a biological sample for the presence of PKC-ι and analyzing the same sample, or another biological sample from the same subject, for other markers that are specific indicators of a cancer. The one or more additional markers may be detected before, during, and/or after detection of PKC-ι is carried out. The methods, devices, and kits described herein may be modified by including agents to detect the additional markers, or nucleic acids encoding the markers.

Cancer markers that may be used in conjunction with the invention include, but are not limited to: alpha fetoprotein (AFP), e.g., for pancreatic, kidney, liver, cervical, and testicular cancers; carcinogenic embryonic antigen (CEA), e.g., for lung, pancreatic, kidney, breast, uterine, liver, gastric, and colorectal cancers; carbohydrate antigen 15-3 (CA15-3), e.g., for lung, pancreatic, breast, and liver cancers; carbohydrate antigen 19-9 (CA19-9), e.g., for lung, uterine, liver, gastric, colorectal, and bile duct cancers; cancer antigen 125 (CA125), e.g., for lung, pancreas, breast, liver, cervical, uterine, gastric, and colorectal cancers; free prostate specific antigen and prostate specific antigen-alpha(1) (PSA), for prostate cancer; free prostate specific antigen (PSAF), for prostate and colorectal cancers; prostate specific antigen-alpha(1)antichymotrypsin complex (PSAC), for prostate cancer; prostatic acid phosphatase (PAP), for prostate cancer; human thyroglobulin (hTG), for thyroid cancer or Wilm's tumor; human chorionic gonadaotropin beta (hCGb), e.g., for lung, pancreatic, kidney, liver, uterine, testicular, colorectal, bladder, and brain cancers; ferritin (Ferr), e.g., for lung cancer, testicular cancer, cancer of the larynx, Burkitt's lymphoma, neuroblastoma, and leukemia; neuron specific enolase (NSE), for lung cancer, thyroid cancer, Wilm's tumor, and neuroblastoma; interleukin 2 (IL-2), for kidney cancer and multiple myeloma; interleukin 6 (IL-6), for kidney cancer, breast cancer, liver cancer, and multiple myeloma; beta 2 microglobulin (B2M), for kidney cancer, liver cancer, prostate cancer, leukemia, multiple myeloma, and lymphoma; and alpha 2 microglobulin (A2M), for prostate cancer. The selection of biological sample (such as blood or urine) in which the aforementioned cancer markers are diagnostic and/or prognostic can be readily determined by those skilled in the art.

As indicated above, the present invention provides a method for monitoring, diagnosing, or for the prognosis of cancer, such as prostate cancer, in a subject by detecting PKC-ι in a biological sample from the subject. In an embodiment, the method comprises contacting the sample with an antibody specific for PKC-ι which is directly or indirectly labeled with a detectable substance, and detecting the detectable substance.

The methods of the invention may be used for the detection of either an over- or an under-abundance of PKC-ι relative to a non-disorder state or the presence of a modified (e.g., less than full length) PKC-ι which correlates with a disorder state (e.g., prostate cancer), or a progression toward a disorder state. The methods described herein may be used to evaluate the probability of the presence of malignant or pre-malignant cells. Such methods can be used to detect tumors, quantitate their growth, and assist in the diagnosis and prognosis of prostate cancer. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods of the invention are particularly useful in the diagnosis of early stage prostate cancer (e.g., when the subject is asymptomatic) and for the prognosis of prostate cancer disease progression and mortality. As illustrated herein, increased levels of PKC-ι detected in a sample (e.g., urine, serum, plasma, whole blood, ascites) compared to a standard (e.g., levels for normal or benign disorders) are indicative of advanced disease stage, serous histological type, suboptimal debulking, large residual tumor, and/or increased risk of disease progression and mortality.

The terms "sample", "biological sample", and the like refer to a type of material known to or suspected of expressing or containing PKC-ι, such as urine. The test sample can be used directly as obtained from the source or following a pretreatment to modify the character of the sample. The sample can be derived from any biological source, such as tissues or extracts, including cells (e.g., tumor cells) and physiological fluids, such as, for example, whole blood, plasma, serum, peritoneal fluid, ascites, and the like. The sample can be obtained from animals, preferably mammals, most preferably humans. The sample can be pretreated by any method and/or can be prepared in any convenient medium that does not interfere with the assay. The sample can be treated prior to use, such as preparing plasma from blood, diluting viscous fluids, applying one or more protease inhibitors to samples such as urine (e.g., 4-(2 aminoethyl)-benzene sulfonyl fluoride, EDTA, leupeptin, and/or pepstatin), and the like. Sample treatment can involve filtration, distillation, extraction, concentration, inactivation of interfering components, the addition of reagents, and the like.

The presence of PKC-ι may be detected in a variety of biological samples, including tissues or extracts thereof. Preferably, PKC-ι is detected in human serum or plasma.

In embodiments of the invention, the method described herein is adapted for diagnosing and monitoring prostate cancer by quantitating PKC-ι in biological samples from a subject. Preferably, the amount of PKC-ι quantitated in a sample from a subject being tested is compared to levels quantitated for another sample or an earlier sample from the subject, or levels quantitated for a control sample. Levels for control samples from healthy subjects may be established by prospective and/or retrospective statistical studies. Healthy subjects who have no clinically evident disease or abnormalities may be selected for statistical studies. Diagnosis may be made by a finding of statistically different levels of PKC-ι compared to a control sample or previous levels quantitated for the same subject.

Agents that are capable of detecting PKC-ι in the biological samples of subjects are those that interact or bind with the PKC-ι polypeptide or the nucleic acid molecule encoding PKC-ι. Examples of such agents (also referred to herein as binding agents) include, but are not limited to, PKC-ι antibodies, PKC-ι binding partners or fragments thereof that bind PKC-ι, PKC-ι binding partners, and nucleic acid molecules that hybridize to the nucleic acid molecules encoding PKC-ι polypeptides. Preferably, the binding agent is labeled with a detectable substance (e.g., a detectable moiety). The binding agent may itself function as a label.

PKC-ι Antibodies

Antibodies specific for PKC-ι that are used in the methods of the invention may be obtained from scientific or commercial sources. Alternatively, isolated native PKC-ι or recombinant PKC-ι may be utilized to prepare antibodies, monoclonal or polyclonal antibodies, and immunologically active fragments (e.g., a Fab or (Fab)$_2$ fragment), an antibody heavy chain, an antibody light chain, humanized antibodies, a genetically engineered single chain F$_v$ molecule (Ladne et al., U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against PKC-ι if they bind with a K$_a$ of greater than or equal to $10^7$ M. In a sandwich immunoassay of the invention, mouse polyclonal antibodies and rabbit polyclonal antibodies are utilized.

In order to produce monoclonal antibodies, a host mammal is inoculated with a PKC-ι protein or peptide and then boosted. Spleens are collected from inoculated mammals a few days after the final boost. Cell suspensions from the spleens are fused with a tumor cell in accordance with the general method described by Kohler and Milstein (*Nature*, 1975, 256:495-497). In order to be useful, a peptide fragment must contain sufficient amino acid residues to define the epitope of the PKC-ι molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of a PKC-ι binding region, including such as Fv, F(ab')$_2$, Fab fragments (Harlow and Lane, 1988, Antibody, Cold Spring Harbor Laboratory Press) for the detection of PKC-ι in the fluids of prostate cancer patients or those at risk, preferably in the urine or blood of prostate cancer patients.

For use in detection and/or monitoring of cancer, the purified antibodies can be covalently attached, either directly or via linker, to a compound which serves as a reporter group to permit detection of the presence of PKC-ι. A variety of different types of substances can serve as the reporter group, including but not limited to enzymes, dyes, radioactive metal and non-metal isotopes, fluorogenic compounds, fluorescent compounds, etc. Methods for preparation of antibody conjugates of the antibodies (or fragments thereof) of the invention useful for detection and monitoring are described in U.S. Pat. Nos. 4,671,958; 4,741,900 and 4,867,973.

In one aspect of the invention, preferred binding epitopes may be identified from a known PKC-ι gene sequence and its encoded amino acid sequence and used to generate PKC-ι antibodies with high binding affinity. Also, identification of binding epitopes on PKC-ι can be used in the design and construction of preferred antibodies. For example, a DNA encoding a preferred epitope on PKC-ι may be recombinantly expressed and used to select an antibody which binds selectively to that epitope. The selected antibodies then are exposed to the sample under conditions sufficient to allow specific binding of the antibody to the specific binding epitope on PKC-ι and the amount of complex formed then detected. Specific antibody methodologies are well understood and described in the literature. A more detailed description of their preparation can be found, for example, in Practical Immunology, Butt, W. R., ed., Marcel Dekker, New York, 1984.

The present invention also contemplates the detection of PKC-ι DNA and antibodies. PKC-ι is a prostate cancer-specific marker. Thus, detection of PKC-ι DNA or antibodies in biological fluids of a subject may enable the diagnosis of prostate cancer.

Protein Binding Assays

Antibodies specifically reactive with PKC-ι, or derivatives, such as enzyme conjugates or labeled derivatives, may be used to detect PKC-ι in various biological samples, for example they may be used in any known immunoassays which rely on the binding interaction between an antigenic determinant of a protein and the antibodies. Examples of such assays are radioimmunoassays, enzyme immunoassay (e.g., ELISA), immunofluorescence, immunoprecipitation, latex agglutination, hemagglutination, and histochemical tests.

An antibody specific for PKC-ι can be labeled with a detectable substance and localized in biological samples based upon the presence of the detectable substance. Examples of detectable substances include, but are not limited to, the following radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against PKC-ι. By way of example, if the antibody having specificity against PKC-ι is a rabbit IgG antibody, the second antibody may be goat anti-rabbit gamma-globulin labeled with a detectable substance as described herein.

Methods for conjugating or labeling the antibodies discussed above may be readily accomplished by one of ordinary skill in the art. (See, for example, Imman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988, regarding methods for conjugating or labeling the antibodies with an enzyme or ligand binding partner).

Time-resolved fluorometry may be used to detect a signal. For example, the method described in Christopoulos T. K. and Diamandis E. P., *Anal. Chem.*, 1992:64:342-346 may be used with a conventional time-resolved fluorometer.

Therefore, in accordance with an embodiment of the invention, a method is provided wherein a PKC-ι antibody is labeled with an enzyme, a substrate for the enzyme is added wherein the substrate is selected so that the substrate, or a reaction product of the enzyme and substrate, forms fluorescent complexes with a lanthanide metal. A lanthanide metal is added and PKC-ι is quantitated in the sample by measuring fluorescence of the fluorescent complexes. The antibodies specific for PKC-ι may be directly or indirectly labeled with an enzyme. Enzymes are selected based on the ability of a substrate of the enzyme, or a reaction product of the enzyme and substrate, to complex with lanthanide metals such as europium and terbium. Examples of suitable enzymes include alkaline phosphatase and beta-galactosidase. Preferably, the enzyme is akline phosphatase. The PKC-ι antibodies may also be indirectly labeled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. Preferably the antibodies are biotinylated, and the enzyme is coupled to streptavidin.

In an embodiment of the method, antibody bound to PKC-ι in a sample is detected by adding a substrate for the enzyme. The substrate is selected so that in the presence of a lanthanide metal (e.g., europium, terbium, samarium, and dysprosium, preferably europium and terbium), the substrate or a reaction product of the enzyme and substrate, forms a fluorescent complex with the lanthanide metal. Examples of enzymes and substrates for enzymes that provide such fluorescent complexes are described in U.S. Pat. No. 5,3112,922 to Diamandis. By way of example, when the antibody is directly or indirectly labeled with alkaline phosphatase, the substrate employed in the method may be 4-methylumbeliferyl phosphate, or 5-fluorpsalicyl phosphate. The fluorescence intensity of the complexes is typically measured using a time-resolved fluorometer, e.g., a CyberFluor 615 Immoanalyzer (Nordion International, Kanata Ontario).

The sample, antibody specific for PKC-ι, or PKC-ι, may be immobilized on a carrier. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling.

In accordance with an embodiment, the present invention provides a mode for determining PKC-ι in an appropriate sample such as urine or blood, preferably serum or plasma, by measuring PKC-ι by immunoassay. It will be evident to a skilled artisan that a variety of immunoassay methods can be used to measure PKC-ι. In general, a PKC-ι immunoassay method may be competitive or noncompetitive. Competitive methods typically employ an immobilized or immobilizable antibody to PKC-ι (anti-PKC-ι) and a labeled form of PKC-ι.

Sample PKC-ι and labeled PKC-ι compete for binding to anti-PKC-ι. After separation of the resulting labeled PKC-ι that has become bound to anti-PKC-ι (bound fraction) from that which has remained unbound (unbound fraction), the amount of the label in either bound or unbound fraction is measured and may be correlated with the amount of PKC-ι in the biological sample in any conventional manner, e.g., by comparison to a standard curve.

Preferably, a noncompetitive method is used for the determination of PKC-ι, with the most common method being the "sandwich" method. In this assay, two anti-PKC-ι antibodies are employed. One of the anti-PKC-ι antibodies is directly or indirectly labeled (also referred to as the "detection antibody") and the other is immobilized or immobilizable (also referred to as the "capture antibody"). The capture and detection antibodies can be contacted simultaneously or sequentially with the biological sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally, it is measured in the capture antibody phase since it comprises PKC-ι bound by ("sandwiched" between) the capture and detection antibodies.

In a typical two-site immunometric assay for PKC-ι, one or both of the capture and detection antibodies are polyclonal antibodies. The label used in the detection antibody can be selected from any of those known conventionally in the art. As with other embodiments of the protein detection assay, the label can be an enzyme or a chemiluminescent moiety, for example, or a radioactive isotope, a fluorophore, a detectable ligand (e.g., detectable by a secondary binding by a labeled binding partner for the ligand), and the like. Preferably, the antibody is labeled with an enzyme that is detected by adding a substrate that is selected so that a reaction product of the enzyme and substrate forms fluorescent complexes. The capture antibody is selected so that it provides a mode for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody can comprise an antibody covalently or noncovalently attached to a solid phase such as a magnetic particle, a latex particle, a microtiter multi-well plate, a bead, a cuvette, or other reaction vessel. An example of an immobilizable capture antibody is an antibody that has been chemically modified with a ligand moiety, e.g., a hapten, biotin, or the like, and that can be subsequently immobilized by contact with an immobilized form of a binding partner for the ligand, e.g., an antibody, avidin, or the like. In an embodiment, the capture antibody can be immobilized using a species specific antibody for the capture antibody that is bound to the solid phase.

A particular sandwich immunoassay method of the invention employs two antibodies reactive against PKC-ι, a second antibody having specificity against an antibody reactive against PKC-ι labeled with an enzymatic label, and a fluorogenic substrate for the enzyme. In an embodiment, the enzyme is alkaline phosphatase (ALP) and the substrate is 5-fluorosalicyl phosphate. ALP cleaves phosphate out of the fluorogenic substrate, 5-fluorosalicyl phosphate, to produce 5-fluorosalicylic acid (FSA). 5-Fluorosalicylic acid can then form a highly fluorescent ternary complex of the form FSA-Tb(3+)-EDTA, which can be quantified by measuring the $Tb^{3+}$ fluorescence in a time-resolved mode. Fluorescence intensity is typically measured using a time-resolved fluorometry as described herein.

The above-described immunoassay methods and formats are intended to be exemplary and are not limiting since, in general, it will be understood that any immunoassay method or format can be used in the present invention.

The protein detection methods, devices, and kits of the invention can utilize nanowire sensor technology (Zhen et al., *Nature Biotechnology*, 2005, 23(10):1294-1301; Lieber et al., *Anal. Chem.*, 2006, 78(13):4260-4269, which are incorporated herein by reference) or microcantilever technology (Lee et al., *Biosens. Bioelectron*, 2005, 20(10):2157-2162; Wee et al., *Biosens. Bioelectron.*, 2005, 20(10):1932-1938; Campbell and Mutharasan, *Biosens. Bioelectron.*, 2005, 21(3):462-473; Campbell and Mutharasan, *Biosens. Bioelectron.*, 2005, 21(4):597-607; Hwang et al., *Lab Chip*, 2004, 4(6):547-552; Mukhopadhyay et al., *Nano. Lett.*, 2005, 5(12):2835-2388, which are incorporated herein by reference) for detection of PKC-I in samples. In addition, Huang et al. describe a prostate specific antigen immunoassay on a commercially available surface plasmon resonance biosensor (*Biosens. Bioelectron.*, 2005, 21(3):483-490, which is incorporated herein by reference) which may be adapted for detection of PKC-ι. High-sensitivity miniaturized immunoassays may also be utilized for detection of PKC-ι (Cesaro-Tadic et al., *Lab chip*, 2004, 4(6):563-569; Zimmerman et al., *Biomed. Microdevices*, 2005, 7(2):99-110, which are incorporated herein by reference).

Nucleic Acids

Nucleic acids including naturally occurring nucleic acids, oligonucleotides, antisense oligonucleotides, and synthetic oligonucleotides that hybridize to the nucleic acid encoding PKC-ι, are useful as agents to detect the presence of PKC-ι in the biological samples of prostate cancer patients or those at risk of prostate cancer, preferably in the urine of prostate cancer patients or those at risk of prostate cancer. The present invention contemplates the use of nucleic acid sequences corresponding to the coding sequence of PKC-ι and to the complementary sequence thereof, as well as sequences complementary to the PKC-ι transcript sequences occurring further upstream or downstream from the coding sequence (e.g., sequences contained in, or extending into, the 5' and 3' untranslated regions) for use as agents for detecting the expression of PKC-ι in biological samples of prostate cancer patients, or those at risk of prostate cancer, preferably in the blood of prostate cancer patients or those at risk of prostate cancer.

The preferred oligonucleotides for detecting the presence of PKC-ι in biological samples are those that are complementary to at least part of the cDNA sequence encoding PKC-ι. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosohodiester linkage. Additionally, these nucleotides themselves, and/or the ribose moieties may be modified.

The oligonucleotides may be synthesized chemically, using any of the known chemical oligonucleotide synthesis methods well described in the art. For example, the oligonucleotides can be prepared by using any of the commercially available, automated nucleic acid synthesizers. Alternatively, the oligonucleotides may be created by standard recombinant DNA techniques, for example, inducing transcription of the noncoding strand. The DNA sequence encoding PKC-ι may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding PKC-ι, oligonucleotides typically within the range of 8-100 nucleotides are preferred. Most preferable oligonucleotides for use in detecting PKC-ι in urine or blood samples are those within the range of 15-50 nucleotides.

The oligonucleotide selected for hybridizing to the PKC-ι nucleic acid molecule, whether synthesized chemically or by recombinant DNA technology, is then isolated and purified using standard techniques and then preferably labeled (e.g., with $^{35}$S or $^{32}$P) using standard labeling protocols.

The present invention also contemplates the use of oligonucleotide pairs in polymerize chain reactions (PCR) to detect the expression of PKC-ι in biological samples. The oligonucleotide pairs include a forward PKC-ι primer and a reverse PKC-ι primer.

The presence of PKC-ι in a sample from a patient may be determined by nucleic acid hybridization, such as but not limited to Northern blot analysis, dot blotting, Southern blot analysis, fluorescence in situ hybridization (FISH), and PCR. Chromatography, preferably HPLC, and other known assays may also be used to determine messenger RNA levels of PKC-ι in a sample.

The PKC-ι encoding nucleic acid molecules conceivably may be found in the biological fluids inside a PKC-ι-positive cancer cell that is being shed or released in the fluid under investigation.

In one aspect, the present invention contemplates the use of nucleic acids as agents for detecting PKC-ι in biological samples of patients, wherein the nucleic acids are labeled. The nucleic agents may be labeled with a radioactive label, a fluorescent label, an enzyme, a chemiluminescent tag, a colorimetric tag or other labels or tags that are discussed above or that are known in the art.

In another aspect, the present invention contemplates the use of Northern blot analysis to detect the presence of PKC-ι mRNA in a sample of bodily fluid. The first step of the analysis involves separating a sample containing PKC-ι nucleic acid by gel electrophoresis. The dispersed nucleic acids are then transferred to a nitrocellulose filter or another filter. Subsequently, the labeled oligonucleotide is exposed to the filter under suitable hybridizing conditions, e.g., 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of PKC-ι nucleic acid present in the biological fluid of a patient.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. The skilled artisan to detect the presence of desired sequence (U.S. Pat. No. 4,683,195) routinely uses polymerase chain reaction.

A specific example of PCR that is routinely performed by the skilled artisan to detect desired sequences is reverse transcript PCR(RT-PCR; Saiki et al., *Science,* 1985, 230:1350; Scharf et al., *Science,* 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

In a preferred embodiment, the methods of detecting PKC-ι nucleic acid in biological fluids of prostate cancer patients or those at risk thereof, preferably blood (or prostate tissue homogenate or extracts) of prostate cancer patients or those at risk thereof, include Northern blot analysis, dot blotting, Southern blot analysis, FISH, and PCR.

Devices

The methods of the invention can be carried out on a solid support. The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. PKC-ι can be detected in a sample in vivo or in vitro (ex vivo). When, according to an embodiment of the invention, the amount of PKC-ι in a sample is to be determined without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

A contacting step in the assay (method) of the invention can involve contacting, combining, or mixing the biological sample and the solid support, such as a reaction vessel, microvessel, tube, microtube, well, multi-well plate, or other solid support. In an embodiment of the invention, the solid support to be contacted with the biological sample (e.g., urine) has an absorbent pad or membrane for lateral flow of the liquid medium to be assayed, such as those available from Millipore Corp. (Bedford, Mass.), including but not limited to Hi-Flow Plus™ membranes and membrane cards, and SureWick™ pad materials.

The diagnostic device useful in carrying out the methods of the invention can be constructed in any form adapted for the intended use. Thus, in one embodiment, the device of the invention can be constructed as a disposable or reusable test strip or stick to be contacted with a biological sample such as urine or blood for which PKC-ι level is to be determined. In another embodiment, the device can be constructed using art recognized micro-scale manufacturing techniques to produce needle-like embodiments capable of being implanted or injected into an anatomical site, such as the peritoneal cavity, for indwelling diagnostic applications. In other embodiments, devices intended for repeated laboratory use can be constructed in the form of an elongated probe.

In preferred embodiments, the devices of the invention comprise a solid support (such as a strip or dipstick), with a surface that functions as a lateral flow matrix defining a flow path for a biological sample such as urine, whole blood, serum, plasma, peritoneal fluid, or ascites.

Immunochromatographic assays, also known as lateral flow test strips or simply strip tests, for detecting various analytes of interest, have been known for some time, and may be used for detection of PKC-ι. The benefits of lateral flow tests include a user-friendly format, rapid results, long-term stability over a wide range of climates, and relatively low cost to manufacture. These features make lateral flow tests ideal for applications involving home testing, rapid point of care testing, and testing in the field for various analytes. The principle behind the test is straightforward. Essentially, any ligand that can be bound to a visually detectable solid support, such as dyed microspheres, can be tested for, qualitatively, and in many cases even semi-quantitatively. For example, a one-step lateral flow immunostrip for the detection of free and total prostate specific antigen in serum is described in Fernandez-Sanchez et al. (*J. Immuno. Methods*, 2005, 307 (1-2):1-12, which is incorporated herein by reference) and may be adapted for detection of PKC-ι in a biological sample such as blood or urine.

Some of the more common immunochromatographic assays currently on the market are tests for pregnancy (as an over-the-counter (OTC) test kit), Strep throat, and *Chlamydia*. Many new tests for well-known antigens have been recently developed using the immunochromatographic assay method. For instance, the antigen for the most common cause of community acquired pneumonia has been known since 1917, but a simple assay was developed only recently, and this was done using this simple test strip method (Murdoch, D. R. et al. *J Clin Microbiol*, 2001, 39:3495-3498). Human immunodeficiency virus (HIV) has been detected rapidly in pooled blood using a similar assay (Soroka, S. D. et al. *J Clin Virol*, 2003, 27:90-96). A nitrocellulose membrane card has also been used to diagnose schistosomiasis by detecting the movement and binding of nanoparticles of carbon (van Dam, G. J. et al. *J Clin Microbial*, 2004, 42:5458-5461).

The two common approaches to the immunochromatographic assay are the non-competitive (or direct) and competitive (or competitive inhibition) reaction schemes (Tech-Note #303, Rev. #001, 1999, Bangs Laboratories, Inc., Fishers, IN). The direct (double antibody sandwich) format is typically used when testing for larger analytes with multiple antigenic sites such as luteinizing hormone (LH), human chorionic gonadotropin (hCG), and HIV. In this instance, less than an excess of sample analyte is desired, so that some of the microspheres will not be captured at the capture line, and will continue to flow toward the second line of immobilized antibodies, the control zone. This control line uses species-specific anti-immunoglobulin antibodies, specific for the conjugate antibodies on the microspheres. Free antigen, if present, is introduced onto the device by adding sample (urine, serum, etc.) onto a sample addition pad. Free antigen then binds to antibody-microsphere complexes. Antibody 1, specific for epitope 1 of sample antigen, is coupled to dye microspheres and dried onto the device. When sample is added, microsphere-antibody complex is rehydrated and carried to a capture zone and control lines by liquid. Antibody 2, specific for a second antigenic site (epitope 2) of sample antigen, is dried onto a membrane at the capture line. Antibody 3, a species-specific, anti-immunoglobulin antibody that will react with antibody 1, is dried onto the membrane at the control line. If antigen is present in the sample (i.e., a positive test), it will bind by its two antigenic sites, to both antibody 1 (conjugated to microspheres) and antibody 2 (dried onto membrane at the capture line). Antibody 1-coated microspheres are bound by antibody 3 at the control line, whether antigen is present or not. If antigen is not present in the sample (a negative test), microspheres pass the capture line without being trapped, but are caught by the control line.

The competitive reaction scheme is typically used when testing for small molecules with single antigenic determinants, which cannot bond to two antibodies simultaneously. As with double antibody sandwich assay, free antigen, if present is introduced onto the device by adding sample onto a sample pad. Free antigen present in the sample binds to an antibody-microsphere complex. Antibody 1 is specific for sample antigen and couple to dyed microspheres. An antigen-carrier molecule (typically BSA) conjugate is dried onto a membrane at the capture line. Antibody 2 (Ab2) is dried onto the membrane at the control line, and is a species-specific anti-immunoglobulin that will capture the reagent particles and confirm that the test is complete. If antigen is present in the sample (a positive test), antibody on microspheres (Ab1) is already saturated with antigen from sample and, therefore, antigen conjugate bound at the capture line does not bind to it. Any microspheres not caught by the antigen carrier molecule can be caught by Ab2 on the control line. If antigen is not present in the sample (a negative test), antibody-coated dyed microspheres are allowed to be captured by antigen conjugate bound at the capture line.

Normally, the membranes used to hold the antibodies in place on these devices are made of primary hydrophobic materials, such as nitrocellulose. Both the microspheres used as the solid phase supports and the conjugate antibodies are hydrophobic, and their interaction with the membrane allows them to be effectively dried onto the membrane.

Samples and/or PKC-ι-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, PKC-ι-specific binding agents may be immobilized on the solid support.

Detection of PKC-ι and cancer biomarkers, and other assays that are to be carried out on samples, can be carried out simultaneously or sequentially with the detection of other target molecules, and may be carried out in an automated fashion, in a high-throughput format.

The PKC-ι-specific binding agents can be deposited but "free" (non-immobilized) in the conjugate zone, and be immobilized in the capture zone of a solid support. The PKC-ι-specific binding agents may be immobilized by non-specific adsorption onto the support or by covalent bonding to the support, for example. Techniques for immobilizing binding agents on supports are known in the art and are described for example in U.S. Pat. Nos. 4,399,217, 4,381,291, 4,357,311, 4,343,312 and 4,260,678, which are incorporated herein by reference. Such techniques can be used to immobilize the binding agents in the invention. When the solid support is polytetrafluoroethylene, it is possible to couple hormone antibodies onto the support by activating the support using sodium and ammonia to aminate it and covalently bonding the antibody to the activated support by means of a carbodiimide reaction (yon Klitzing, Schultek, Strasburger, Fricke and Wood in "Radioimmunoassay and Related Procedures in Medicine 1982", International Atomic Energy Agency, Vienna (1982), pages 57-62.).

The diagnostic device of the invention can utilize lateral flow strip (LFS) technology, which has been applied to a number of other rapid strip assay systems, such as over-the-counter early pregnancy test strips based on antibodies to human chorionic gonadotropin (hCG). As with many other diagnostic devices, the device utilizes a binding agent to bind the target molecule (PKC-ι). The device has an application zone for receiving a biological sample such as blood or urine, a labeling zone containing label which binds to PKC-ι in the sample, and a detection zone where PKC-ι label is retained.

Binding agent retained in the detection zone gives a signal, and the signal differs depending on whether PKC-ι levels in the biological sample are lower than, equal to, or greater than a given threshold concentration. For example, in the case of serum PKC-ι for the detection of prostate cancer, the threshold concentration may be between 0 ng/ml and 2.0 ng/ml. A sample from a subject having a PKC-ι level equal to or greater than the given reference PKC-ι concentration can be referred to as a "threshold level", "threshold amount", or "threshold sample". The application zone in the device is suitable for receiving the biological sample to be assayed. It is typically formed from absorbent material such as blotting paper. The labeling zone contains binding agent that binds to any PKC-ι in the sample. In one embodiment, the binding agent is an antibody (e.g., monoclonal antibody, polyclonal antibody, antibody fragment). For ease of detection, the binding agent is preferably in association with a label that provides a signal that is visible to the naked eye, e.g., it is tagged with a fluorescent tag or a colored tag such as conjugated colloidal gold, which is visible as a pink color.

The detection zone retains PKC-ι to which the binding agent has bound. This will typically be achieved using an immobilized binding agent such as an immobilized antibody. Where the binding agent in the labeling zone and the detection zone are both antibodies, they will typically recognize different epitopes on the target molecule (PKC-ι protein). This allows the formation of a "sandwich" comprising antibody-PKC-ι-antibody.

The detection zone is downstream of the application zone, with the labeling zone typically located between the two. A sample will thus migrate from the application zone into the labeling zone, where any in the sample binds to the label. PKC-ι-binding agent complexes continue to migrate into the detection zone together with excess binding agent. When the PKC-ι-binding agent complex encounters the capture reagent, the complex is retained whilst the sample and excess binding agent continue to migrate. As PKC-ι levels in the sample increase, the amount of binding agent (in the form of PKC-ι-binding agent complex) retained in the detection zone increases proportionally.

In preferred embodiments, the device of the invention has the ability to distinguish between samples according to the threshold concentration. This can be achieved in various ways.

One type of device includes a reference zone that includes a signal of fixed intensity against which the amount of binding agent retained in the detection zone can be compared—when the signal in the detection zone equals the signal in the reference zone, the sample is a threshold sample; when the signal in the detection zone is less intense than the reference zone, the sample contains less PKC-ι than a threshold sample; when the signal in the detection zone is more intense than the reference zone, the sample contains more PKC-ι than a threshold sample.

A suitable reference zone can be prepared and calibrated without difficulty. For this type of device, the binding agent will generally be present in excess to PKC-ι in the sample, and the reference zone may be upstream or, preferably, downstream of the detection zone. The signal in the reference zone will be of the same type as the signal in the detection zone, i.e., they will typically both be visible to the naked eye, e.g., they will use the same tag. A preferred reference zone in a device of this type comprises immobilized protein (e.g., bovine serum albumin) which is tagged with colloidal gold.

In another device of the invention, the reference zone is downstream of the detection zone and includes a reagent which captures binding agent (e.g., an immobilised anti-binding agent antibody). Binding agent that flows through the device is not present in excess, but is at a concentration such that 50% of it is bound by a sample having PKC-ι at the threshold concentration. In a threshold sample, therefore, 50% of the binding agent will be retained in the detection zone and 50% in the reference zone. If the PKC-ι level in the sample is greater than in a threshold sample, less than 50% of the binding agent will reach the reference zone and the detection zone will give a more intense signal than the reference zone; conversely, if the PKC-ι level in the sample is less than in a threshold sample, less than 50% of the binding agent will be retained in the detection zone and the reference zone will give a more intense signal than the detection zone.

In another device of the invention which operates according to similar principles, the reference zone is downstream of the detection zone and includes a limiting amount of a reagent which captures binding agent (e.g., an immobilised anti-binding agent antibody). The reagent is present at a level such that it retains the same amount of label which would bind to the detection zone for a threshold sample, with excess label continuing to migrate beyond the reference zone.

In these three types of device, therefore, a comparison between the detection zone and the reference zone is used to compare the sample with the threshold concentration. The detection: reference binding ratio can preferably be determined by eye. Close juxtaposition of the detection and reference zones is preferred in order to facilitate visual comparison of the signal intensities in the two zones.

In a fourth type of device, no reference zone is needed, but the detection zone is configured such that it gives an essentially on/off response, e.g., no signal is given below the threshold concentration but, at or above the threshold, signal is given.

In a fifth type of device, no reference zone is needed, but an external reference is used which corresponds to the threshold concentration. This can take various forms, e.g., a printed card against which the signal in the detection zone can be compared, or a machine reader which compares an absolute value measured in the detection zone (e.g., a calorimetric signal) against a reference value stored in the machine.

In some embodiments of the invention, the device includes a control zone downstream of the detection zone. This will generally be used to capture excess binding agent that passes through the detection and/or reference zones (e.g., using immobilized anti-binding agent antibody). When binding agent is retained at the control zone, this confirms that mobilization of the binding agent and migration through the device have both occurred. It will be appreciated that this function may be achieved by the reference zone.

In a preferred embodiment, the detection, reference and control zones are preferably formed on a nitrocellulose support.

Migration from the application zone to the detection zone will generally be assisted by a wick downstream of the detection zone to aid capillary movement. This wick is typically formed from absorbent material such as blotting or chromatography paper.

The device of the invention can be produced simply and cheaply, conveniently in the form of a dipstick. Furthermore, it can be used very easily, for instance by the home user. The invention thus provides a device which can be used at home as a screen for cancer, such as prostate cancer.

In still other devices, using electromagnetic sensor, the detection sensitivity can be greatly enhanced, and can also increase the speed of the assay.

Kits for Diagnosing or Monitoring Prostate Cancer

In one aspect, the present invention includes kits comprising the required elements for diagnosing or monitoring cancer. Preferably, the kits comprise a container for collecting biological fluid from a patient and an agent for detecting the presence of PKC-ι or its encoding nucleic acid in the fluid. The components of the kits can be packaged either in aqueous medium or in lyophilized form.

The methods of the invention can be carried out using a diagnostic kit for qualitatively or quantitatively detecting PKC-ι in a sample such as blood or urine. By way of example, the kit can contain binding agents (e.g., antibodies) specific for PKC-ι, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit. In one embodiment, the kit includes one or protease inhibitors (e.g., a protease inhibitor cocktail) to be applied to the biological sample to be assayed (such as blood or urine).

Kits for diagnosing or monitoring prostate cancer containing one or more agents that detect the PKC-ι protein, such as but not limited to PKC-ι antibodies, fragments thereof, or PKC-ι binding partners, can be prepared. The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

Kits containing one or more agents that detect PKC-ι nucleic acid, such as but not limited to the full length PKC-ι nucleic acid, PKC-ι oligonucleotides, and pairs of PKC-ι primers can also be prepared. The agent(s) can be packaged with a container for collecting biological samples from a patient. The nucleic acid can be in the labeled form or to be labeled form.

Other components of the kit may include but are not limited to, means for collecting biological samples, means for labeling the detecting agent (binding agent), membranes for immobilizing the PKC-ι protein or PKC-ι nucleic acid in the biological sample, means for applying the biological sample to a membrane, means for binding the agent to PKC-ι in the biological sample of a subject, a second antibody, a means for isolating total RNA from a biological fluid of a subject, means for performing gel electrophoresis, means for generating cDNA from isolated total RNA, means for performing hybridization assays, and means for performing PCR, etc.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, *Curr. Opin. Genet. Dev.:* 12, 225-232 (2002); Sharp, *Genes Dev.,* 15:485-490 (2001)). In mammalian cells, RNAi can be triggered by 21-nucleotide (nt) duplexes of small interfering RNA (siRNA) (Chiu et al., *Mol. Cell.* 10:549-561 (2002); Elbashir et al., *Nature* 411:494-498 (2001)), or by micro-RNAs (miRNA), functional small-hairpin RNA (shRNA), or other dsRNAs which can be expressed in vivo using DNA templates with RNA polymerase III promoters (Zeng et al., *Mol. Cell.* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci. USA* 99(9):6047-6052 (2002); McManus et al., *RNA* 8:842-850 (2002); Sui et al., *Proc. Natl. Acad. Sci. USA* 99(6):5515-5520 (2002)), each of which are incorporated herein by reference in their entirety.

The scientific literature contains many reports of endogenous and exogenous gene expression silencing using siRNA, highlighting their therapeutic potential (Gupta, S. et al. *PNAS,* 2004, 101:1927-1932; Takaku, H. *Antivir Chem. Chemother,* 2004, 15:57-65; Pardridge, W. M. *Expert Opin. Biol. Ther.,* 2004, 4:1103-1113; Zheng, B. J. *Antivir. Ther.,* 2004, 9:365-374; Shen, W. G. *Chin. Med. J. (Engl),* 2004, 117:1084-1091; Fuchs, U. et al. *Curr. Mol. Med.,* 2004, 4:507-517; Wadhwa, R. et al. *Mutat. Res.,* 2004, 567:71-84; Ichim, T. E. et al. *Am. J. Transplant,* 2004, 4:1227-1236; Jana, S. et al. *Appl. Microbiol. Biotechnol.,* 2004, 65:649-657; Ryther, R. C. et al. *Gene Ther.,* 2005, 12:5-11; Chae, S-S. et al., *J. Clin. Invest.,* 2004, 114:1082-1089; Fougerolles, A. et al., *Methods Enzymol.,* 2005, 392:278-296), each of which is incorporated herein by reference in its entirety. Therapeutic silencing of endogenous genes by systemic administration of siRNAs has been described in the literature (Kim B. et al., *American Journal of Pathology,* 2004, 165:2177-2185; Soutschek J. et al., *Nature,* 2004, 432:173-178; Pardridge W. M., *Expert Opin. Biol. Ther.,* 2004, July, 4(7):1103-1113), each of which is incorporated herein by reference in its entirety.

Accordingly, the invention includes such interfering RNA molecules that are targeted to PKC-ι mRNA. The interfering RNA molecules are capable, when suitably introduced into or expressed within a cell that otherwise expresses PKC-ι mRNA, of suppressing expression of the PKC-ι gene by RNAi. The interfering RNA may be a double-stranded siRNA. As the skilled person will appreciate, and as explained further herein, an siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme Dicer, to yield two distinct, but hybridized, RNA molecules. In one embodiment, the invention provides an interfering RNA that is capable, when suitably introduced or expressed within a cell that normally expresses PKC-ι mRNA, suppresses its expression by RNAi, wherein the interfering RNA is generally targeted to the PKC-ι. Preferably, the interfering RNA sequence is within the range of about 19 to 23 nucleotides. For example, in those embodiments in which an shRNA is utilized, that portion of the shRNA targeting PKC-ι is preferably within the range of about 19 to 23 nucleotides.

It is expected that perfect identity/complementarity between the interfering RNA used in the method of the invention and the target sequence, although preferred, is not essential. Accordingly, the interfering RNA may include a single mismatch compared to the target sequence within the PKC-ι mRNA. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

siRNA Molecules

Short interfering RNAs (siRNAs) induce the sequence-specific suppression or silencing (i.e., reducing expression which may be to the extent of partial or complete inhibition) genes by the process of RNAi. Thus, siRNA is the intermediate effector molecule of the RNAi process. The interfering RNA that function as PKC-ι inhibitors include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the PKC-ι mRNA, and the other strand is identical or substantially identical to the first strand. The dsRNA molecules that function as PKC-ι inhibitors can be chemically synthesized, or can be transcribed in vitro from a DNA template, or in vivo from, e.g., shRNA. The dsRNA molecules can be designed using any method known in the art, for instance, by using the following protocol:

1. Using any method known in the art, compare the potential targets to the appropriate genome database (human, mouse, rat, etc.) and eliminate from consideration any target sequences with significant homology to other coding sequences. One such method for sequence homology searches is known as BLAST, which is available at the National Center for Biotechnology Information (NCBI) web site of the National Institutes of Health. Also available on the NCBI webs site is the HomoloGene database, which is a publicly available system for automated detection of homologs among the annotated genes of several completely sequenced eukaryotic genomes and is readily utilized by those of ordinary skill in the art.

2. Select one or more sequences that meet your criteria for evaluation. Further general information regarding the design and use of siRNA can be found in "The siRNA User Guide," available at the web site of the laboratory of Dr. Thomas Tuschl at Rockefeller University (Elbashir et al., *EMBO J.*, 2001, 20:6877-6888).

3. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Initially, basic criteria were defined for identification of efficient siRNA, such as GC content and position of the targeted sequence in the context of the mRNA (Elbashir S M. et al., *Methods*, 2002, 26:199-213). Further progress was achieved more recently, when the assembly of the RNAi enzyme complex was described as being dependent on thermodynamic characteristics of the siRNA (Khrvorova A. et al., *Cell*, 2003, 115:209-216; Schwarz D. S. et al., *Cell*, 2003, 115:199-208). The relative stability of both ends of the duplex was determined to have effects on the extent to which the individual strands enter the RNAi pathway. In addition, certain sequence motifs at defined positions of the siRNA were reported to influence its potency (Amarzguioui M. and H. Prydz, *Biochem. Biophys. Res. Commun.*, 2004, 316:1050-1058; Reynolds A. et al., *Nature Biotechnol.*, 2004, 22:326-330). On this basis, sophisticated algorithms have been developed to increase the success rate of siRNA design and are available to those skilled in the art (Amarzguioui M. and H. Prydz, 2004; Reynolds A. et al., 2004; and Ui-Tei K. et al., *Nucl. Acids Res.*, 2004, 32:936-948, each of which is incorporated herein in its entirety).

Other computational tools that may be used to select siRNAs of the present invention include the Whitehead siRNA selection Web Server from the bioinformatics group at the Whitehead Institute for Biomedical Research in Cambridge, Mass., and other disclosed in Yuan, B. et al. ("siRNA Selection Server: an automated siRNA oligonucleotide prediction server", *Nucleic Acids Research*, 2004, Vol. 32, W130-W134, Web Server issue) and Bonetta L. ("RNAi: Silencing never sounded better", *Nature Methods*, October, 2004, 1(1):79-86), each of which are incorporated by reference herein in their entirety.

The efficiencies of different siRNAs may differ significantly. However, strategies for rational design of effective interfering RNA exist (Gong D. and J. E. Ferrell Jr., TRENDS in Biotechnology, 2004, 22(9):451; Schubert S. et al., J. Mol. Biol., 2005, 348:883-893; Pancoska P. et al., Nucleic Acids Research, 2004, 32(4):1469-1479; Mittal V., *Nat. Rev. Genet.*, 2004, 5(5):355-365, each of which is incorporated herein by reference in its entirety).

Screening for the most efficient siRNAs using cell cultures may be carried out. Several in vitro screening methods based on the use of siRNA mixtures, which may contain a particular efficient siRNA (or several), have been developed. These include the preparation of siRNA mixtures using RNase III or Dicer enzymes to digest longer double-stranded RNAs, such as BLOCK-IT products (INVITROGEN, Carlsbad Calif.) (Yang D. et al., *Proc. Natl. Acad. Sci. USA*, 2002, 99:9942-9947; Myers J. W. et al., *Nat. Biotechnol.*, 2003, 21:324-328). The short RNAs produced as a result of these digestions have been found to be efficient in RNAi. Oligonucleotide arrays can also be used for the efficient preparation of defined mixtures of siRNAs for reducing the expression of exogenous and endogenous genes such as PKC-ι (Oleinikov A. V. et al., *Nucleic Acids Research*, 2005, 33(10):e92).

The PKC-ι inhibitors of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The PKC-ι inhibitors of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53 (1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The PKC-ι inhibitors of the present invention can also be labeled using any method known in the art; for instance, nucleic acids can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^3$H, $^{32}$P, or other appropriate isotope.

Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

There are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dharmacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, B. et al., *Nat. Med.*, 2005, 11(9), 944-951).

siRNA Delivery for Longer-Term Expression

Synthetic siRNAs can be delivered into cells by methods known in the art, including cationic liposome transfection (LIPOFECTAMINE 2000 reagent, for example) and electroporation, for example. However, these exogenous siRNA generally show short term persistence of the silencing effect (4 to 5 days in cultured cells), which may be beneficial in certain embodiments. To obtain longer suppression of PKC-ι expression and to facilitate delivery under certain circumstances, one or more siRNA duplexes, e.g., PKC-ι ds siRNA, can be expressed within cells from recombinant DNA constructs (McIntyre G. J. and G. C. Fanning, *BMC Biotechnology*, 2006, 6:1-8). Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of PKC-ι mRNA, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci. USA* 99(22):14236-40 (2002)). In adult mice, efficient delivery of siRNA can be accomplished by the "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)). Nanoparticles, liposomes and other cationic lipid molecules can also be used to deliver siRNA into animals. It has been shown that siRNAs delivered systemically in a liposomal formulation can silence the disease target apolipoprotein B (ApoB) in non-human primates (Zimmermann T. S. et al., *Nature*, 2006, 441:111-114). A gel-based agarose/liposome/siRNA formulation is also available (Jiamg M. et al., *Oligonucleotides*, 2004, Winter, 14(4):239-48).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the PKC-ι mRNA to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the PKC-ι mRNA. Antisense nucleic acid sequences and delivery methods are well known in the art (Goodchild J., *Curr. Opin. Mol. Ther.*, 2004, April, 6(2):120-128; Clawson G. A. et al., *Gene Ther.*, 2004, September, 11(17):1331-1341), which are incorporated herein by reference in their entirety. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence within the PKC-ι mRNA. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire PKC-ι mRNA sequence, but can also be an oligonucleotide that is antisense to only a portion of the PKC-ι mRNA.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., systemically or locally by direct injection at a tissue site), or generated in situ such that they hybridize with or bind to cellular mRNA and/or genomic DNA encoding the PKC-ι to thereby inhibit expression of the PKC-ι gene. Alternatively, antisense nucleic acid molecules can be modified to target selected cells (such as megakaryocytes and/or megakaryotcyte progenitors) and then administered systemically. For systemic administration, antisense molecules can be modified such that they specifically bind to receptors or antigens (such as CD9, CD41, CD61, actin, or FVIIIRAg) expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.*, 215:327-330 (1987)).

PKC-ι expression can be inhibited by targeting nucleotide sequences complementary to the regulatory region of the PKC-ι gene to form triple helical structures that prevent expression of PKC-ι in target cells. See generally, Helene, C. Anticancer Drug Des. 6:569-84 (1991); Helene, C. Ann. N. Y. Acad. Sci. 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. Ribozymes and methods for their delivery are well known in the art (Hendry P. et al., *BMC Chem. Biol.*, 2004, December, 4(1):1; Grassi G. et al., *Curr. Pharm. Biotechnol.*, 2004, August, 5(4):369-386; Bagheri S. et al., *Curr. Mol. Med.*, 2004, August, 4(5):489-506; Kashani-Sabet M., *Expert Opin. Biol. Ther.*, 2004, November, 4(11):1749-1755), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for PKC-ι mRNA can include one or more sequences complementary to a nucleotide sequence within the PKC-ι mRNA, and a sequence having a known catalytic sequence responsible for mRNA cleavage (see U.S. Pat. No. 5,093,246 or Haselhoff and Gerlach *Nature* 334:585-591 (1988)). For example, a derivative of a Tetrahymena L-19 IVS RNA can be constructed in which the nucleotide sequence of the active site is complementary to the nucleotide sequence to be cleaved in the mRNA encoded by a uORF of an extended, overlapping 5'-UTR AS mRNA species (see, e.g., Cech et al. U.S. Pat. No. 4,987,071; and Cech et al. U.S. Pat. No. 5,116,742). Alternatively, PKC-I mRNA can be used to select a catalytic RNA having a specific ribonuclease activity from a pool of RNA molecules (see, e.g., Bartel, D. and Szostak, J. W. *Science* 261:14111418 (1993)).

Nucleic Acid Targets

The nucleic acid targets of PKC-ι inhibitors that are polynucleotides (referred to herein as "polynucleotide PKC-ι inhibitors" or "nucleic acid PKC-ι inhibitors") such as the antisense, interfering RNA molecules, and ribozymes described herein, may be any portion of the PKC-ι gene or PKC-ι mRNA. In other embodiments, the nucleic acid target is a translation initiation site, 3' untranslated region, or 5' untranslated region.

The target PKC-ι sequence can be within any orthologue of PKC-ι, such as sequences substantially identical to human, mouse, rat, or bovine, or a portion of any of the foregoing, including but not limited to those publicly available from GenBank.

The term "orthologue" as used herein refers to a sequence which is substantially identical to a reference sequence. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known PKC-I nucleic acid sequences. BLAST protein searches can be performed with the XBLAST program, score=50, word length=3, to obtain amino acid sequences homologous to known polypeptide products of the PKC-I gene. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., a human cDNA library, using a probe designed to identify sequences which are substantially identical to a reference sequence.

Pharmaceutical Compositions and Methods of Administration

The PKC-ι inhibitors of the subject invention (such as interfering RNA molecules, antisense molecules, and ribozymes) can be incorporated into pharmaceutical compositions. Such compositions typically include the PKC-ι inhibitor and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, 19$^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N. J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the PKC-ι inhibitors can be delivered in the form of an aerosol spray from a pressurized container or dispenser which contains a suitable propellant, e.g., a gas such as carbon dioxide, or a nebulizer. Such inhalation methods and inhalant formulations include those described in U.S. Pat. No. 6,468,798.

Systemic administration of PKC-ι inhibitors can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The PKC-ι inhibitors can also be administered by transfection or infection using methods known in the art, including but not limited to the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm.* 53(2):151-160 (1996), erratum at *Am. J. Health Syst. Pharm.* 53(3):325 (1996).

PKC-ι inhibitors that are polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the polynucleotide PKC-ι inhibitors are prepared with carriers that will protect the polynucleotide against rapid elimination from, or degradation in, the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. Strategies that inhibit members of the RNAse A family of enzymes or can otherwise protect polynucleotide PKC-ι inhibitors from these enzymes may be utilized. For example, U.S. Pat. No. 6,096,720 (Love et al.) describes oligonucleotides targeted to human raf mRNA, which are entrapped in sterically stabilized liposomes. In one embodiment, the oligonucleotide in Love et al. is a chimeric olignonucleotide containing a first region to enhance target affinity and a second region that is a substrate for RNase. siSHIELD RNAse inhibitor is designed to prevent degradation of siRNA by RNase (MP BIOMEDICALS, Irvine, Calif.). A strategy for the compaction of short oligonucleotides into well-defined condensates may also be used to deliver the polynucleotides of the subject invention (Sarkar T.

et al., *Nucleic Acids Research*, 2005, 33(1):143-151), which is incorporated herein by reference in its entirety.

In particular, suitable techniques for cellular administration of the polynucleotide PKC-ι inhibitors, such as interfering RNA, in vitro or in vivo are disclosed in the following articles:

General Reviews:

Borkhardt, A. *Cancer Cell*, 2002, 2:167-8; Hannon, G. J. *Nature*, 2002, 418:244-51; McManus, M. T. and Sharp, P. A. *Nat Rev Genet.*, 2002, 3:737-47; Scherr, M. et al. *Curr Med. Chem.*, 2003, 10:245-56; Shuey, D. J. et al. *Drug Discov Today*, 2002, 7:1040-6; Gilmore, I. R. et al., *J. Drug Target.*, 2004, 12(6):315-340; Dykxhoorn, D. M. and Lieberman J., *Annu. Rev. Med.*, 2005, 56:401-423.

Systemic Delivery Using Liposomes:

Lewis, D. L. et al. *Nat. Genet.*, 2002, 32:107-8; Paul, C. P. et al. *Nat. Biotechnol.*, 2002, 20:505-8; Song, E. et al. *Nat. Med.*, 2003, 9:347-51; Sorensen, D. R. et al. *J Mol Biol.*, 2003, 327:761-6.

Virus Mediated Transfer:

Abbas-Terki, T. et al. *Hum Gene Ther.*, 2002, 13:2197-201; Barton, G. M. and Medzhitov, R. *Proc Natl Acad Sci USA*, 2002, 99:14943-5; Devroe, E. and Silver, P. A. *BMC Biotechnol.*, 2002, 2:15; Lori, F. et al. *Am J Pharmacogenomics*, 2002, 2:245-52; Matta, H. et al. *Cancer Biol Ther.*, 2003, 2:206-10; Qin, X. F. et al. *Proc Natl Acad Sci USA*, 2003, 100:183-8; Scherr, M. et al. *Cell Cycle*, 2003, 2:251-7; Shen, C. et al. *FEBS Lett.*, 2003, 539:111-4; Lee S. K. et al., *Blood*, 2005, 106(3):818-826, epub Apr. 14, 2005.

Peptide Delivery:

Morris, M. C. et al. *Curr Opin Biotechnol.*, 2000, 11:461-6; Simeoni, F. et al. *Nucleic Acids Res.*, 2003, 31:2717-24.

Song E. et al. describe antibody mediated in vivo delivery of siRNAs via cell-surface receptors (Song E. et al., *Nat. Biotechnol.*, 2005, 23(6):709-717, epub May 22, 2005). This cell-specific delivery technique can be used to target interfering RNA molecules to the cell-surface receptors on megakaryocytes and megakaryocyte progenitors.

Other technologies that may be suitable for delivery of polynucleotide PKC-ι inhibitors, such as interfering RNA, to the target cells are based on nanoparticles or nanocapsules such as those described in U.S. Pat. No. 6,649,192B and 5,843,509B. Recent technologies that may be employed for selecting, delivering, and monitoring interfering RNA molecules include Raab, R. M. and Stephanopoulos, G. *Biotechnol. Bioeng.*, 2004, 88:121-132; Huppi, K. et al. *Mol. Cell*, 2005, 17:1-10; Spagnou, S. et al. *Biochemistry*, 2004, 43:13348-13356; Muratovska, A. and Eccles, M. R. *FEBS Lett.*, 2004, 558:63-68; Kumar, R. et al. *Genome Res.*, 2003, 13:2333-2340; Chen, A. A. et al. *Nucleic Acids Res.*, 2005, 33:e190; Dykxhoorn, D. M. et al. *Gene Ther.*, 2006, epub ahead of print; Rodriguez-Lebron, E. and Paulson, H. L. *Gene Ther.*, 2005, epub ahead of print; Pai, S. I. et al. *Gene Ther.*, 2005, epub ahead of print; Raoul, C. et al. *Gene Ther.*, 2005, epub ahead of print; Manfredsson, F. P. et al. *Gene Ther.*, 2005, epub ahead of print; Downward, J. *BMJ*, 2004, 328: 1245-1248.

A mixture of PKC-ι inhibitors, of the same type or different types, may be introduced into cells in vitro or in vivo. For example, a mixture or pool of polynucleotide PKC-ι inhibitors such as interfering RNA molecules (e.g., 2-4 interfering molecules or more) can be introduced into cells (Oleinikov A. V. et al., *Nucleic Acids Research*, 2005, 33(10):e92). Preferably, the interfering RNA molecules target different regions of the PKC-ι mRNA. Preferably, the interfering RNA molecules have been previously validated as individually functioning to reduce PKC-ι expression. The individual interfering RNAs of the mixture can be chemically synthesized (Elbashir S. M. et al., *Genes Dev.*, 2001, 15:188-200) or introduced as short DNA templates containing RNA polymerase promoter, which are transcribed within the cells in vitro or in vivo (Yu J. Y. et al., *Proc. Natl. Acad. Sci. USA*, 99:6047-6052).

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The PKC-ι inhibitor can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a PKC-ι inhibitor can include a single treatment or can include a series of treatments.

The polynucleotide PKC-ι inhibitors (e.g., interfering RNA, antisense oligonucleotide, or ribozyme) can be introduced (administered) into cells (such as mammalian cells) in vitro or in vivo using known techniques, as those described herein, to suppress gene expression. Similarly, genetic constructs (e.g., transcription vectors) containing DNA of the invention may be introduced into cells in vitro or in vivo using known techniques, as described herein, for transient or stable expression of RNA, to suppress gene expression. When administered to the cells in vivo, the polynucleotide PKC-ι inhibitors can be administered to a subject systemically (e.g., intravenously), for example, or administered locally at the site of the cells (such as the prostate).

The cells in which the polynucleotide PKC-ι inhibitors are introduced may be any cell, such as a megakaryocyte or megakaryocyte progenitor, containing PKC-ι mRNA. The cells can be primary cells, cultured cells, cells of cell lines, etc. In one embodiment, the cells are from prostate.

As used herein, the terms "subject", "patient", and "individual" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one mammalian species to another mammalian species), relative to the subject.

The polynucleotide PKC-ι inhibitors of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci. USA* 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotide PKC-ι inhibitors can be small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., (2002), supra; Miyagishi and Taira, *Nature Biotechnol.* 20:497-500 (2002); Paddison et al. (2002), supra; Paul (2002), supra; Sui (2002) supra; Yu et al. (2002), supra.

SiRNAs targeting PKC-ι mRNA may be fused to other nucleotide molecules, or to polypeptides, in order to direct their delivery or to accomplish other functions. Thus, for example, fusion proteins comprising a siRNA oligonucleotide that is capable of specifically interfering with expression of PKC-ι may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/H is (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode polynucleotide PKC-ι inhibitors (e.g., siRNA), and in particular to "recombinant nucleic acid constructs" that include any nucleic acid such as a DNA polynucleotide segment that may be transcribed to yield PKC-ι-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci. USA* 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a PKC-ι mRNA sequence may be transcribed under the control of a single promoter such that the siRNA polynucleotide forms a hairpin molecule (Paul et al., supra). In such instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotide PKC-ι inhibitors can be expressed in mammalian cells, yeast, bacteria, or other cells under the control of appropriate promoters, providing ready systems for evaluation of siRNA polynucleotides that are capable of interfering with PKC-ι expression as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor Laboratory Press, N. Y., (2001).

The appropriate DNA sequence(s) may be inserted into the vector by a variety of procedures. in general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N. Y.); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the E. coli lac or tip, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Examples of Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., Biotechniques 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above). A tissue-specific promoter allows preferential expression of the polynucleotide PKC-ι inhibitor in a given target tissue, thereby avoiding expression in other tissues. The majority of studies in this field to date have utilized the promoter and enhancer for prostate specific antigen (PSA) (Martiniello-Wilks et al., Hum. Gene Ther. 9 (11): 1617-1626, 1998). Other examples of prostate tissue-specific promoters have been reported, including the promoters for probasin (Yan et al., Prostate, 32 (2): 129-139, 1997; Matusik, U.S. Pat. No. 5,783,681, Jul. 21, 1998) and prostatic acid phosphatase (Zelivianskietal., Biochem. Biophys. Res. Commun., 245 (1): 108-112, 1998).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as E. coli, Streptomyces, Salmonella typhimurium; fungal cells, such as yeast; insect cells, such as Drosophila S2 and Spodoptera Sf9; animal cells, such as CHO, COS or 293 cells; adenoviruses; plant cells, or any suitable cell already adapted to in vitro propagation or so established de novo.

Various mammalian cell culture systems can also be employed to produce polynucleotide PKC-ι inhibitors from recombinant nucleic acid constructs of the present invention. The invention is therefore directed in part to a method of producing a polynucleotide, such as an siRNA, by culturing a host cell comprising a recombinant nucleic acid construct that comprises at least one promoter operably linked to a polynucleotide PKC-ι inhibitor. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organdies; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

In general, the target nucleic acid is DNA or RNA. However, inventive methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the sensitivity of the target cells to radiation therapy may be extracted by a variety of techniques such as that described by Sambrook, et al. (Molecular Cloning: A Laboratory Manual, Cold Spring Harbor, N.Y., 1989; incorporated in its entirety herein by reference).

Cells expressing the target nucleic acid isolated from a subject can be obtained in a biological specimen from the subject. The cells, or nucleic acid, can be isolated from tumor tissue, blood, plasma, serum, lymph, lymph nodes, spleen, bone marrow, or any other biological specimen containing the target nucleic acid. Tumor tissue, blood, plasma, serum, lymph, spleen, and bone marrow are obtained by various medical procedures known to those of skill in the art.

The inventive methods are useful for producing a clinical response to treatment of prostate cancer or other cell proliferation disorders. A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g., its cells do not invade surrounding tissues or metastasize to distant sites. The term "malignant" refers to a tumor that is metastatic, invades contiguous tissue or no longer under normal cellular growth control.

As used herein, "a clinical response" is the response of a subject to modulation of the gene of interest. Criteria for determining a response to therapy are widely accepted and enable comparisons of the efficacy alternative treatments (see Slapak and Kufe, Principles of Cancer Therapy, in Harrisons's Principles of Internal Medicine, $13^{th}$ edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

As used herein, the terms "administer", "introduce", "apply", "treat", "transplant", "implant", "deliver", and grammatical variations thereof, are used interchangeably to provide PKC-ι inhibitors to target cells in vitro (e.g., ex vivo) or in vivo, or provide genetically modified (engineered) cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

PKC-ι inhibitors (also referred to herein as "active compounds") can be incorporated into pharmaceutical compositions suitable for administration. Such compositions typically comprise the PKC-ι-inhibiting nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to target cells with monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical canier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Assays. The invention provides a method (also referred to herein as a "screening assay") for identifying PKC-ι inhibitors, i.e., candidate or test compounds or agents (e.g., peptides, peptidomimetics, small molecules or other drugs) that bind to the PKC-ι protein or have a stimulatory or inhibitory effect on, for example, the PKC-ι gene expression or PKC-ιgene activity. Such identified compounds may be useful for the modulation of drug resistance. In one embodiment, the invention provides assays for screening candidate or test compounds which bind to or modulate the activity of the target gene protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. *Proc. Natl. Acad. Sci. USA,* 1993, 90:6909; Erb et al. *Proc. Natl. Acad. Sci. USA,* 1994, 91:11422; Zuckennann et al. *J. Med. Chem.,* 1994, 37:2678; Cho et al. *Science,* 1993, 261:1303; Carrell et al. *Angew. Chem. Int. Ed. Engl.,* 1994, 33:2059; Carell et al. *Angew. Chem. hit. Ed. Engl.,* 1994, 33:2061; and Gallop et al. *J. Med. Chem.,* 1994, 37:1233.

Libraries of compounds may be presented in solution (e.g., Houghten *Bio/Techniques,* 1992, 13:412-421), or on beads (Lam *Nature,* 1991, 354:82-84), chips (Fodor Nature, 1993, 364:555-556), bacteria (U.S. Pat. No. 5,223,409), spores (U.S. Pat. Nos. 5,571,698; 5,403,484; and 5,223,409), plasmids (Cull et al. *Proc. Natl. Acad. Sci. USA,* 1992, 89:1865-1869) or on phage (Scott and Smith Science, 1990, 249:386-390; Devlin Science, 1990, 249:404-406; Cwirla et al. *Proc. Natl. Acad. Sci.,* 1990, 87:6378-6382; and Felici *J. Mol: Biol.,* 1991, 222:301-310).

In one embodiment, an assay is a cell-based assay in which a cell which expresses the target gene protein, or a biologically active portion thereof, is contacted with a test compound and the ability of the test compound to bind to the target gene protein is determined. The cell, for example, can be a yeast cell or a cell of mammalian origin. Determining the ability of the test compound to bind to the target gene protein can be accomplished, for example, by coupling the test compound with a radioisotope or enzymatic label such that binding of the test compound to the target gene protein or biologically active portion thereof can be determined by detecting the labeled compound in a complex. For example, test compounds can be labeled with $^{125}$I, $^{35}$C, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses the target gene protein, or a biologically active portion thereof, with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or a biologically active portion thereof as compared to the known compound.

In another embodiment, an assay is a cell-based assay comprising contacting a cell expressing the target gene protein, or a biologically active portion thereof, with a test compound and determining the ability of the test compound to modulate (e.g., stimulate or inhibit) the activity of the target gene protein or biologically active portion thereof. Determining the ability of the test compound to modulate the activity of the target gene or a biologically active portion thereof can be accomplished, for example, by determining the ability of the target gene protein to bind to or interact with the target gene target molecule. As used herein, a "target molecule" is a molecule with which the target gene protein binds or interacts in nature, for example, a molecule in the nucleus or cytoplasm of a cell which expresses the target gene protein. The target gene target molecule can be a non-target gene molecule or the target gene protein or polypeptide. The target, for example, can be a second intracellular protein which has catalytic activity, a protein which naturally binds to the target gene, or a protein which facilitates the association of DNA with the target gene.

Determining the ability of the target gene protein to bind to or interact with the target gene target molecule can be accomplished by one of the methods described above for determining direct binding. In a preferred embodiment, determining the ability of the target gene protein to bind to or interact with the target gene target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting the target gene protein or biologically active portion thereof with a test compound and determining the ability of the test compound to bind to the target gene protein or biologically active portion thereof. Binding of the test compound to the target gene protein can be determined either directly or indirectly as described above. In a preferred embodiment, the assay includes contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or biologically active portion thereof as compared to the known compound.

In another embodiment, an assay is a cell-free assay comprising contacting the target gene protein or biologically active portion thereof with a test compound and determining the ability of the test compound to modulate (e.g., stimulate or inhibit) the activity of the target gene protein or biologically active portion thereof. Determining the ability of the test compound to modulate the activity of the target gene can be accomplished, for example, by determining the ability of the target gene protein to bind to the target gene target molecule by one of the methods described above for determining direct binding. In an alternative embodiment, determining the ability of the test compound to modulate the activity of the target gene can be accomplished by determining the ability of the target gene protein further modulate the target gene target molecule. For example, the catalytic/enzymatic activity of the target molecule on an appropriate substrate can be determined as previously described.

In yet another embodiment, the cell-free assay comprises contacting the target gene protein or biologically active portion thereof with a known compound which hinds the target gene to form an assay mixture, contacting the assay mixture with a test compound, and determining the ability of the test compound to interact with the target gene protein, wherein determining the ability of the test compound to interact with the target gene protein comprises determining the ability of the target gene protein to preferentially bind to or modulate the activity of the target gene target molecule.

The cell-free assays of the present invention are amenable to use of both native and variant forms (e.g., peptide fragments and fusion proteins) of the target gene. In the case of cell-free assays comprising a hydrophobic form of the target gene, it may be desirable to utilize a solubilizing agent such that the hydrophobic form of the target gene is maintained in solution.

Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the target gene or its target molecule to facilitate separation of complexed from uncomplexed forms of one or both of the proteins, as well as to accommodate automation of the assay. Binding of a test compound to the target gene, or interaction of the target gene with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/target gene fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or the target gene protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the target gene binding or activity determined using standard techniques.

Other techniques for immobilizing proteins on matrices can also be used in the screening assays of the invention. For example, either the target gene or its target molecule can be immobilized utilizing conjugation of biotin and streptavidin. Biotinylated target gene or target molecules can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the target gene or target molecules but which do not interfere with binding of the target gene protein to its target molecule can be derivatized to the wells of the plate, and unbound target or the target gene trapped in the wells by antibody conjugation. Methods for detecting such complexes, in addition to those described above for the GST-immobilized complexes, include immunodetection of complexes using antibodies reactive with the target gene or target molecule, as well as enzyme-linked assays which rely on detecting an enzymatic activity associated with the target gene or target molecule.

In another embodiment, modulators of the target gene expression are identified in a method in which a cell is contacted with a candidate compound and the expression of the target gene (mRNA or protein, or the copy number of the target gene) in the cell is determined. The level of expression of the target gene in the presence of the candidate compound is compared to the level of expression of the target gene in the absence of the candidate compound. The candidate compound can then be identified as a modulator of the target gene expression based on this comparison. For example, when expression of the target gene mRNA or protein is greater (statistically significantly greater) in the presence of the candidate compound than in its absence, the candidate compound is identified as a stimulator of the target gene mRNA or protein expression. Alternatively, when expression of the target gene mRNA or protein is less (statistically significantly less) in the presence of the candidate compound than in its absence, the candidate compound is identified as an inhibitor of the target gene mRNA or protein expression. The level of the target gene mRNA or protein expression in the cells, or the number of the target gene copies per cell can be determined by methods described herein for detecting the target gene genomic DNA, mRNA, or protein.

Target gene proteins can be used as "bait proteins" in a two-hybrid assay or three hybrid assay (see, e.g., U.S. Pat. No. 5,283,317; Zervos et al. *Cell*, 1993, 72:223-232; Madura et al. *J. Biol. Chem.*, 1993, 268:12046-12054; Bartel et al. *Bio/Techniques*, 1993, 14:920-924; Iwabuchi et al. *Oncogene*, 1993, 8:1693-1696; and WO94/10300), to identify other proteins, which bind to or interact with the target gene ("target gene-binding proteins" or "target gene-bp") and modulate the target gene activity.

The two-hybrid system is based on the modular nature of most transcription factors, which consist of separable DNA-binding and activation domains. Briefly, the assay utilizes two different DNA constructs. In one construct, the gene that codes for the target gene is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming the target gene-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the target gene.

This invention further pertains to novel agents identified by the above-described screening assays and uses thereof for treatments as described herein.

Predictive Medicine. The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the target gene protein and/or nucleic acid expression as well as the target gene activity, in the context of a biological sample (e.g., blood, serum, cells, tissue) to thereby determine whether an individual is afflicted with a disease or disorder, or is at risk of developing a disorder, associated with aberrant target gene expression or activity (e.g., altered drug resistance). The invention also provides for prognostic (or predictive) assays for determining whether an individual is at risk of developing a disorder associated with the target gene protein, nucleic acid expression or activity (e.g., altered drug resistance). For example, mutations in the target gene can be assayed in a biological sample. Such assays can be used for prognostic or predictive purpose to thereby prophylactically treat an individual prior to the onset of a disorder characterized by or associated with the target gene protein, nucleic acid expression or activity. For example, because prostate cancer is associated with instances where the PKC-ι is expressed at a higher level in cells than normal, expression of the PKC-ι target gene can be used as an indicator of prostate cancer.

Another aspect of the invention provides methods for determining the target gene protein, nucleic acid expression or the target gene activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Diagnostic Assays.

The invention provides a method of assessing expression, especially undesirable expression, of a cellular target gene. Undesirable (e.g., excessive) expression may indicate the presence, persistence or reappearance of prostate cancer. More generally, aberrant expression may indicate the occurrence of a deleterious or disease-associated phenotype contributed to by the target gene.

An exemplary method for detecting the presence or absence of the target gene in a biological sample involves obtaining a biological sample (preferably from a body site implicated in a possible diagnosis of diseased or malignant tissue) from a test subject and contacting the biological sample with a compound or an agent capable of detecting the target gene protein or nucleic acid (e.g., mRNA, genomic DNA) that encodes the target gene protein such that the presence of the target gene is detected in the biological sample. The presence and/or relative abundance of the target gene indicates aberrant or undesirable expression of a cellular the target gene, and correlates with the occurrence in situ of prostate cancer.

A preferred agent for detecting the target gene mRNA or genomic DNA is a labeled nucleic acid probe capable of hybridizing to the target gene mRNA or genomic DNA. The nucleic acid probe can be, for example, a full-length the target gene nucleic acid, or a portion thereof, such as an oligonucleotide of at least 15, 30, 50, 100, 250 or 500 nucleotides in length and sufficient to specifically hybridize under stringent conditions to the target gene mRNA or genomic DNA. Other suitable probes for use in the diagnostic assays of the invention are described herein.

A preferred agent for detecting the target gene protein is an antibody capable of binding to the target gene protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect the target gene mRNA, protein, or genomic DNA in a biological sample in vitro as well as in vivo. For example, in vitro techniques for detection of the target gene mRNA include Northern hybridizations and in situ hybridizations. In vitro techniques for detection of the target gene protein include enzyme linked immunosorbent assays (ELISAs), Western blots, immunoprecipitations and immunofluorescence. In vitro techniques for detection of the target gene genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a human serum isolated by conventional means from a subject.

In another embodiment, the methods further involve obtaining a control biological sample from a control subject, contacting the control sample with a compound or agent capable of detecting the target gene protein, mRNA, or genomic DNA, such that the presence of the target gene protein, mRNA or genomic DNA is detected in the biological sample, and comparing the presence of the target gene protein, mRNA or genomic DNA in the control sample with the presence of the target gene protein, mRNA or genomic DNA in the test sample.

The invention also encompasses kits for detecting the presence of the target gene in a biological sample (a test sample). Such kits can be used to determine if a subject is suffering from or is at increased risk of developing a disorder associated with aberrant expression of the target gene (e.g., the presence of a drug resistance cancer). For example, the kit can comprise a labeled compound or agent capable of detecting the target gene protein or mRNA in a biological sample and means for determining the amount of the target gene in the sample (e.g., an anti-target gene antibody or an oligonucleotide probe which binds to DNA encoding the target gene). Kits may also include instruction for observing that the tested subject is suffering from or is at risk of developing a disorder associated with aberrant expression of the target gene if the amount of the target gene protein or mRNA is above or below a normal level.

For antibody-based kits, the kit may comprise, for example: (1) a first antibody (e.g., attached to a solid support) which binds to the target gene protein; and, optionally, (2) a second, different antibody which binds to the target gene protein or the first antibody and is conjugated to a detectable agent.

For oligonucleotide-based kits, the kit may comprise, for example: (1) a oligonucleotide, e.g., a detectably labeled oligonucleotide, which hybridizes to the target gene nucleic acid sequence or (2) a pair of primers useful for amplifying the target gene nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the target gene.

Pharmacogenomics. Agents, or modulators which have a stimulatory or inhibitory effect on the target gene activity (e.g., PKC-ι) as identified by a screening assay can be administered to individuals to treat (prophylactically or therapeutically) disorders (e.g., prostate cancer) associated with aberrant target gene activity. In conjunction with such treatment, the pharmacogenomics (i.e., the study of the relation PKC-ι between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder, *Clin. Chem.,* 1997, 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans).

Thus, the activity of the target gene product (PKC-ι), expression of the target gene nucleic acid, or mutation content of the target genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with the target gene modulator, such as a modulator identified by one of the exemplary screening assays described herein.

Monitoring of Effects During Clinical Trials. Monitoring the influence of agents (e.g., drugs, compounds) on the expression or activity of the target gene (e.g., the ability to modulate the PKC-ι phenotype of a cell) can be applied not only in basic drug screening, but also in clinical trials. For example, the effectiveness of an agent determined by a screening assay to decrease the target gene expression, protein levels, or downregulate the target gene activity, can be monitored in clinical trails of subjects exhibiting increased target gene expression, protein levels, or upregulated target gene activity.

Alternatively, the effectiveness of an agent determined by a screening assay to increase the target gene expression, protein levels, or upregulate target gene activity (e.g., to decrease megakaryocyte production), can be monitored in clinical trials of compounds designed to increase the target gene expression, protein levels, or upregulate target gene activity. In such clinical trials, the expression or activity of the target gene and, preferably, other genes that have been implicated in, for example, a cellular proliferation disorder, can be used as a "read out" or markers of the drug resistance of a particular cell.

For example, and not by way of limitation, genes, including the target gene, that are modulated in cells by treatment with an agent (e.g., compound, drug or small molecule) which modulates the target gene activity (e.g., identified in a screening assay) can be identified. Thus, to study the effect of agents on cellular proliferation disorders, for example, in a clinical trial, cells can be isolated and RNA prepared and analyzed for the levels of expression of the target gene and other genes implicated in the disorder. The levels of gene expression (i.e., a gene expression pattern) can be quantified by Northern blot analysis or RT-PCR, or as is otherwise known in the art, or alternatively by measuring the amount of protein produced, by one of the methods as described herein, or by measuring the levels of activity of the target gene or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of the target gene protein, mRNA, or genomic DNA in the preadministration sample; (iii) obtaining one or more post-administration samples from the subject; (iv) detecting the level of expression or activity of the target gene protein, mRNA, or genomic DNA in the post-administration samples; (v) comparing the level of expression or activity of the target gene protein, mRNA, or genomic DNA in the pre-administration sample with the target gene protein, mRNA, or genomic DNA in the post administration sample or samples; and (vi) altering the administration of the agent to the subject accordingly. For example, increased administration of the agent may be desirable to decrease the expression or activity of the target gene to lower levels than detected, i.e., to increase the effectiveness of the agent.

Methods of Treatment. The present invention provides for both prophylactic and therapeutic methods of treating a subject at risk of (or susceptible to) a disorder or having a disorder associated with aberrant target gene expression or activity. Alternatively, the target gene expression or activity may be normal (non-aberrant) but a decrease in target gene expression or activity would nonetheless have a beneficial effect on the subject. Such disorders include various prostate cancers.

Prophylactic Methods. In one aspect, the invention provides a method for preventing in a subject, a disease or condition associated with an aberrant target gene expression or activity (e.g., the development of drug resistance), by administering to the subject an agent which modulates the target gene expression. Subjects at risk for a condition which is caused or contributed to by aberrant target gene expression or activity can be identified by, for example, any or a combination of diagnostic or prognostic assays as is known in the art. Administration of a prophylactic agent can occur prior to the manifestation of symptoms characteristic of target gene aberrancy, such that a disease or disorder is prevented or, alternatively, delayed in its progression. For example, administration of a prophylactic agent to a patient in need of a bone marrow transplant may prevent or delay the development of platelet production dropping below a critical threshold. Depending on the type of the target gene aberrancy, for example, the target gene agonist or the target gene antagonist agent can be used for treating the subject. The appropriate agent can be determined based on screening assays described herein.

Therapeutic Methods. Another aspect of the invention pertains to methods of modulating the target gene expression or activity for therapeutic purposes. The modulation of expression of the target gene disclosed in the method of the invention involves contacting a cell with an agent that modulates one or more of the activities of the target gene protein activity associated with the cell. An agent that modulates the target gene protein activity can be an agent as described herein, such as a nucleic acid or a protein, a naturally-occurring cognate ligand of the target gene protein, a peptide, the target gene peptidomimetic, or other small molecule. In one embodiment, the agent stimulates one or more of the biological activities of the target gene protein. Examples of such stimulatory agents include active the target gene protein and a nucleic acid molecule encoding the target gene that has been introduced into the cell. In another embodiment, the agent inhibits one or more of the biological activities of the target gene protein. Examples of such inhibitory agents include antisense target gene nucleic acid molecules and anti-target gene antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of the target gene protein or nucleic acid molecule. In one embodiment, the method involves administering an agent, or combination of agents that modulates (e.g., upregulates or downregulates) the target gene expression or activity. In another embodiment, the method involves administering the target gene protein or nucleic acid molecule as therapy to compensate for reduced or aberrant target gene expression or activity.

For example, in one embodiment, the method involves administering a desired drug to an individual with a cell population expressing relatively high target gene levels, and coadministering an inhibitor of the target gene expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an the target gene antisense oligonucleotide in combination with one or more other antisense oligonucleotides) can be administered to the individual sufficiently in advance of administration of the drug to allow the antisense composition to permeate the individual's tissues, especially tissue comprising the transformed cells to be eradicated; to be internalized by transformed cells; and to disrupt the target gene expression and/or protein production.

Inhibition of the target gene activity is desirable in situations in which the target gene is abnormally upregulated, e.g., in prostate carcinogenesis.

The dosage ranges for the administration of the therapeutic agents of the invention are those large enough to produce the desired effect in which the symptoms of prostate cancer are treated. The dosage should not be so large as to cause adverse side effects, such as unwanted cross-reactions, anaphylactic reactions, and the like. Generally, the dosage will vary with the age, condition, sex and extent of the symptoms in the patient and can be determined by one of skill in the art. The dosage can be adjusted by the individual physician in the event of any counterindications. The dosage amount may depend on the specific prostate cancer which is treated and can be readily determined using known dosage adjustment techniques by a physician having ordinary skill in treatment of these disorders. The dosage amount will generally lie within an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1-20 mg/kg. The preferred dose of about 0.5-5 mg/kg is particularly useful for compounds containing the therapeutic agents disclosed herein, in one or more dose administrations daily, for one or several days.

Any of the compositions described herein may be formulated for pharmacological or therapeutic administration either to a mammal, or more preferably to a human. As such, the compositions may be contained in a pharmaceutically acceptable carrier. The preferred mode of administration of a peptide active agent is by injection, either intravenous, intraarterial, intramuscular or subcutaneous. Other routes of administration may also be possible and would be included within the scope of the present disclosure.

The compositions may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

A peptide can be formulated into a composition in a neutral or salt form. Pharmaceutically acceptable salts, include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The therapeutic agents of the invention can be administered parenterally by injection or by gradual perfusion over time. The therapeutic agents of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The invention also relates to a method for preparing a medicament or pharmaceutical composition comprising the therapeutic agents of the invention, the pharmaceutical composition being used for therapy of hepatocellular carcinoma.

As used herein the terms "cancer", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-cancerous (e.g., benign), malignant, metastatic, and non-metastatic cells. Detection of cancerous cell is of particular interest.

"PKC-ι antagonist" is a compound that specifically binds to PKC-ι, preferably human PKC-ι or binds to a PKC-ι polynucleotide or fragment thereof, and inhibits the activity and/or expression of PKC-ι protein or polynucleotide. Examples thereof include ligands that bind PKC-ι such as antibodies and antibody fragments, recombinant or native. Other examples include antisense oligonucleotides that bind to a PKC-ι polynucleotide or fragment thereof.

In a further embodiment of the invention, the PKC-ι molecule can be used as a target for molecular therapy. For this, several approaches, such as the application of small interfering RNA (siRNA) as PKC-ι antagonists targeting the PKC-ι transcript, can be used to inhibit or downregulate the expression of PKC-ι in prostate cancer cells. In addition, suppression of the expression of PKC-ι can render prostate cells more sensitive to current therapeutic drugs or gene therapy, improving the efficacy of the treatments.

In yet another embodiment of the invention, RNAi directed to the suppression of PKC-ι expression is used for the therapeutic treatment of cancers, preferably prostate cancer. The following is a discussion of relevant art pertaining to RNAi. The discussion is provided only for understanding of the invention that follows. The summary is not an admission that any of the work described below is prior art to the claimed invention.

RNA interference refers to the process of sequence specific post-transcriptional gene silencing in animals mediated by short interfering RNAs (siRNAs) (Fire et al., 1998, Nature, 391, 806). As currently understood, the presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, Nature, 409, 363). Short interfering RNAs derived from Dicer activity are typically about 21 to about 23 nucleotides in length and comprise about 19 base pair duplexes. The RNAi response also features an endonuclease complex containing a siRNA, commonly referred to as an RNA-induced silencing complex (RISC), which mediates cleavage of single-stranded RNA having sequence homologous to the siRNA. As such, siRNA molecules of the invention can be used to mediate gene silencing via interaction with RNA transcripts wherein such interaction results in gene silencing either at the transcriptional level or post-transcriptional level.

By "inhibit", "downregulate", "knockdown" or "silence" it is meant that the expression of the gene, or level of RNAs or equivalent RNAs encoding PKC-ι, is reduced below that observed in the absence of the nucleic acid molecules of the invention. In one embodiment, inhibition or downregulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or downregulation with antisense oligonucleotides is preferably below that level observed in the presence of, for example, an oligonucleotide with scrambled sequence or with mismatches. In another embodiment, inhibition or downregulation of PKC-ι with the nucleic acid molecule of the instant invention is greater in the presence of the nucleic acid molecule than in its absence.

This invention relates to compounds, compositions, and methods useful for modulating the expression of genes, such as PKC-ι, using short interfering nucleic acid (siNA) molecules. This invention further relates to compounds, compositions, and methods useful for modulating the expression and activity of PKC-ι and/or PKC-ι genes, or genes involved in PKC-ι pathways of gene expression and/or PKC-ι activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of PKC-ι and/or PKC-ι genes. A siRNA of the invention can be unmodified or chemically-modified. A siRNA of the instant invention can be chemically synthesized, expressed from a vector or enzymatically synthesized. The instant invention may also feature various chemically-modified synthetic short interfering nucleic acid (siNA) molecules capable of modulating PKC-ι and/or PKC-ι gene expression or activity in cells by RNA interference (RNAi). The use of chemically-modified siNA improves various properties of native siNA molecules through increased resistance to nuclease degradation in vivo and/or through improved cellular uptake. The siNA molecules of the instant invention provide useful reagents and methods for a variety of therapeutic, diagnostic, target validation, genomic discovery, genetic engineering, and pharmacogenomic applications.

In one embodiment, the invention features a double-stranded short interfering ribonucleic acid (siRNA) molecule that down-regulates expression of PKC-ι gene, wherein said siRNA molecule comprises about 19 to about 23 base pairs.

In another embodiment, the invention features a siRNA molecule comprising a region, for example, the antisense region of the siRNA construct, complementary to a sequence comprising a PKC-ι and/or PKC-ι gene sequence or a portion thereof.

In one embodiment, the invention features a medicament comprising a siRNA molecule of the invention.

In one embodiment, the invention features an active ingredient comprising a siRNA molecule of the invention.

In one embodiment, the invention features a composition comprising a siRNA molecule of the invention in a pharmaceutically acceptable carrier or diluent.

Thus, based on the foregoing, the invention provides novel methods of diagnosing, treating and/or preventing cancers characterized by PKC-ι overexpression based on the detection of PKC-ι or the use of PKC-ι as a target for therapeutic intervention or prophylactic intervention.

It should be understood, however, that this invention is not limited to the particular embodiments described, as such may, of course, vary. It is also to be understood that the terminology used herein is for the purpose of describing particular embodiments only, and is not intended to be limiting.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each tenth Unless defined otherwise, all technical and scientific terms have the same meaning as commonly understood by one of ordinary skill in the art to which this invention belongs. Although any methods and materials similar or equivalent to those described herein can be used in the practice or testing of the present invention, the preferred methods and materials are now described.

All publications and patent applications mentioned herein are incorporated by reference to disclose and describe the methods and/or materials in connection with which the publications are cited.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting.

MATERIALS AND METHODS

Reagents and Antibodies

Polyclonal primary antibodies were purchased from the following companies: β-actin (sc-1616) goat polyclonal, PKC-α (sc-8393) mouse monoclonal (Santa Cruz Biotechnology, CA); Anti-PKC-ι mouse monoclonal catalog number 610176 (Transduction Laboratory, Lexington, Ky.). Secondary antibodies were purchased from the following companies: HRPi Goat×Mouse IgG catalog number JGM035146, HRP Goat×Rabbit IgG (catalog number JGZ035144) (Accurate, Westbury, N.Y.); HRP Bovine anti-goat IgG (sc-2350) (Santa Cruz Biotechnology, CA).

Specific antibodies were purchased from Santa Cruz Biotechnology and the amount of antibodies used was as follow: full PARP sc-7150 (5 μg, 1:1000 dilution) rabbit polyclonal antibody, caspase-7 sc-8510 (5 μg, 1:1000 dilution) goat polyclonal, survivn sc-17779 (5 μg, 1:1000 dilution) mouse monoclonal, cytochrome C sc-13560 (5 μg, 1:1000 dilution) mouse monoclonal, β-actin sc-1616 (5 μg, 1:1000 dilution) goat polyclonal, phospho-Bad (5 μg, 1:10000 dilution) ser-112, ser-136, ser-155 (sc-7998-R, sc-12970-R, sc-7999-R respectively).

Cleaved PARP (Asp214) (catalog number 9541) rabbit polyclonal (5 μg, 1:1000 dilutions) was purchased form Cell Signaling. Secondary antibody Goat×Mouse IgG (catalog number JGM035146; 1 μg, 1:10000 dilution) was from Accurate. Goat anti-rabbit sc-2004 (1 μg, 1:5000 dilutions) was from Santa Cruz. Anti-rabbit IgG (catalog number 7074; 1 μg, 1:1 000 dilution) was purchased form Cell Signaling.

Prostate Tissue Analysis

Human autopsy derived BPH and PIN tissues were obtained from the Cooperative Human Tissue Network (Southern Division) at The University of Alabama at Birmingham. Tissue specimens were obtained from males of varying ages (57-80 years old). The cancer prostate tissues were obtained from patient prostectomies from May-August 2007. The specimens were placed on ice immediately after prostactomy, frozen in liquid nitrogen within 30 minutes to 1 hour after prostectomy. Prostate tissues (0.5-1 g) were resuspended and sonicated in 2 mL homogenization buffer (50 mM HEPES [pH 7.5], 150 mM NaCl, 0.1% Tween-20, 1 mM EDTA (ethylenediamine-tetraacetic acid) and 2 mM EGTA (ethylene glycol bis(β-aminoethyl ether)-N,N,N',N',-tetraacetic acid), 0.1 mM orthovanadate, 1 mM NaF, 2 mM PMSF(phenyl-methylsulfonly fluoride), 2.5 μg/ml leupeptin, 1 mM DTT (dithiothreitol), 0.15 U/mL aprotinin (Agrawal et al., 1995). The suspension was sonicated for 3 fifteen seconds cycles on ice. Prostate tissue suspensions or cell lysates were centrifuged at 40,000 g for 30 min to obtain cell extracts. Protein content was measured according to Bradford (Bradford, 1976). Tissue extracts containing equal amounts of protein in each lane were run on SDS-PAGE gels according to Laemmli (Laemmli, 1970). Proteins were transblotted according to Towbin et al. (Towbin et al., 1979). The tissue lysates (100 μg) were Western blotted for PKC-α (10 μg, 1:500 dilution): and PKC-ι (5 μg, 1:4000 dilution) and β-actin (10 μg, 1:500 dilution). Secondary antibodies were obtained from Accurate (JGM035146, Westboro, N.Y. and JG2035744) and used at 1:15000 dilutions (1 μg). Immunoreactive bands were visualized with enhanced chemiluminescence according to manufactures instructions (ECL; Amersham, Piscataway, N. J.).

Densitometry

The intensity of each band was measured using Gel Base/Gel Blot-Pro software (Synoptics, LTD). Briefly, the background intensity was subtracted from the intensity of each band, to derive the corrected intensity.

Immunohistochemical Staining

Unstained sections of core biopsies from 10 patients with untreated prostate adenocarcinoma (1 core with adenocarcinoma from each patient), 8 patients with prostatic high grade prostatic intraepithelial neoplasm (HGPIN) (1 core with HGPIN from each patient) and 9 patients with benign prostate (1 core with from each patient) were used. Following deparaffinization of the sections, and antigen retrieval using citrate microwave antigen retrieval, blocking was performed. For detection of PKC-α, sections were incubated with anti-PKC-α (1:100 dilution) for 60 minutes followed by washing and detection with EnVision detection system using mouse IgG polymer and DAB chromogen. For detection of PKC-ι separate sections were subsequently incubated over night with purified mouse anti-PKC-ι (1:200 dilution; BD transduction laboratories), followed by washing and subsequent 30 minute incubation with 1:200 rat anti-mouse IgG2b. Final detection was done using DAB chromogen. All sections were examined for PKC-α and PKC-ι expression and scored using Allred semi quantitative scoring system (Allred et al., 1998). The Allred score is a composite of the percentage of cells that stained and the intensity of their staining. The percentage of cells staining is called proportion score and is classified from 0 through 5, and the intensity of cells staining is called intensity score and is rated as 1, 2 or 3; thus the composite score ranges between 0-8 with 0 being the lowest and 8 being the maximum score. The adenocarcinoma glands, glands with HGPIN, benign glands and stromal cells were scored separately.

Inhibition of Gene Expression with siRNA

For short interference RNAs: control siRNA-A (sc-37007), PKC-ι siRNA (h2) (sc-44320), PKC-ζ siRNA (sc-29451), PKC-δ siRNA (sc-36253), siRNA transfection reagent (se-29528), and transfection media (se-36868) were purchased from Santa Cruz Biotechnology, CA. RNA interference functions by a regulator mechanism for sequence-specific gene silencing through double stranded RNA (dsRNA). Sequence specific RNA that was 19-25 nucleotides in length were synthesized by Santa Cruz Biotechnology against PKC-ι. The PKC-ι siRNA is a pooled sequence which consists of three combined RNA sequences-mRNA locations. The gene accession number for PKC-ι is NM_002740. PKC-ι siRNA: 663 5'-CAAGCCAAGCGUUUCAACA-3' (SEQ ID NO: 1);5'-UGUUGAAACGCUUGGCUU G-3' (SEQ ID NO: 2); 739 5'-GGAACGAUUGGGUUGUCAU-3' (SEQ ID NO: 3); 5'-AUGACAACCCAAUCGUUUCC-3' (SEQ ID NO: 4); 2137 5'-CCCAAUAUCUUCUCUUGUA-3' (SEQ ID NO: 5); 5'-UACAAGAGAAGAUAUUGGG3' (SEQ ID NO: 6); PKC-ζ siRNA: 5'-AAGACGACACAUGUCUCUCAC-CCUGUCUC-3' (SEQ ID NO: 7); 5'-AUACAUUUCU ACAGCUAGC-3' (SEQ ID NO: 8) antisense; 5'-GAGA-CAGGGUGAGAGACAUGUGUCGUCUU-3' (SEQ ID NO: 9); 5'-GCUAGC UGUAGAAAUGUAU-3' (SEQ ID NO: 10) sense; PKC-ζ siRNA: 5'-UCAUAAAUCAGUUU-CUCAC-3' (SEQ ID NO: 11) antisense; 5'-AUGACAAA-GAAAUUCUGAC-3' (SEQ ID NO: 12) antisense; 5'-GUGAGAAACUGAUUUAUGA-3' (SEQ ID NO: 13) sense; 5'-GUCAGAAUUUCUUUGUCAU-3' (SEQ ID NO: 14) sense. Negative controls containing a scramble sequence that do not lead to the specific degradation of any known cellular mRNA were synthesized. The control siRNA-A sequence is proprietary and the manufacuture (Santa Cruz Biotechnology) does not reveal the sequence. The effects of PKC-ι, PKC-ζ, and PKC-δ siRNA were determined in exponentially growing RWPE-1 cells, LNCaP cells and DU145 cells in complete media over 72 hours. Cells were plated on 75 cm$^2$ at a density of 1.5 to 2.5×10$^5$ cells/flask.

The siRNAs complexes were made according to the following procedures: 60 μl of siRNAs (10 μM stock solution) were combined with 60 μl of tranfection reagent and incubated at room temperature for 30 minutes to make the siRNA complex. The siRNA complex was then added to twenty four hours post plated cells giving a final concentration of 50 nM of siRNA complex in complete media. The cells were incubated with either siRNA-A, or PKC-ι, PKC-ζ, and PKC-δ siRNA (50 nM for RWPE-1, 100 nM for LNCaP and 150 nM for DU-145 respectively). Following treatments, the cells were washed with phosphate buffered saline (PBS), trypsinized and resuspended in 2-3 ml of PBS.

Cell viability was quantified using trypan blue exclusion assay and the numbers of unstained cells were counted as mentioned above. Three independent experiments were carried out for each treatment with controls. Cell viability was determined relative to vehicle control using the mean and SD for each time point. Statistical determination by Student's T test using Minitab program (Minitab Inc. State College, Pa.).

Cell Cycle Analysis by Flow Cytometry

Confluent cell cultures were semi-synchronized by serum starvation for 48 hours. Cells were then incubated in serum and removed at specific times, washed in DPBS, trypsinized (catalog number 25-053-CI, Fisher Scientific), and fixed by dropwise addition (while vortexing) of cold ethanol until a concentration of 60% ethanol was reached. The day before analysis, 60% ethanol was decanted and PBTB (PBS, 0.2% Triton x100 and 1% bovine serum albumin) was added. Triton x100 (catalog number BP151-500) and bovine serum albumin (BSA) (catalog number B4287) were purchased from Fisher Scientific. The cells were counted and diluted to 1×10$^6$ cells/ml with PBTB. The cells were filter with cell strainer and 50 μl of RNase was added. Nuclei were analyzed for DNA content using a propidium iodide (PI) 10 μL staining protocol and flow cytometry (Allred et al., 1998). RNase (catalog number 83931) and PI (catalog number P4170) were purchased from Sigma. The distributions of 1×10$^6$ nuclei were quantified using a FAC STAR$^{Plus}$, flow cytometry (Becton Dickinson, San Jose, Calif.) and ModFitLT Cell Cycle Analysis program (Version 2.0; Verity Software House, Topsham, Me., USA). The results from three separate independent experiments were used to determine the mean viability and standard deviation for each time point.

Cells were treated with siRNA complex and removed at indicated times. The cells were washed in Dulbecco's phosphate-buffered saline (DPBS), trypsinized, and fixed by dropwise addition (while vortexing) of cold ethanol until a concentration of 60% ethanol was reached. The day before analysis, the cells were treated with 50 μl of RNase and propidium iodide (PI) 10 μL. The distributions of 1×10$^6$ nuclei were quantified using a FAC STAR$^{Plus}$ flow cytometry. The results from three separate independent experiments were used to determine the mean viability and standard deviation for each time point.

Kinase Assay

DU-145 cells (3.75×10$^5$) were grown as a monolayer in T75 flasks overnight. Whole cell lysates of (100 μg) were immunoprecipitated as follows: cell lystaes (50 μg) were pre-cleared for 30 min at 4° C. with anti-rabbit IgG-agarose beads (1:1 v/v, 10 μl) (catalog number A8914; Sigma Aldrich) and incubated with 5 μg of PKC-ι rabbit polyclonal antibody and/or IKKα/β rabbit polyclonal antibody (5 μg) overnight at 4° C. and then a further 1 h with anti-rabbit IgG-agarose beads (1:1 v/v, 50 μl). The immunoprecipitated samples were incubated with kinase buffer (50 μl of 3.03 mg/10 ml ATP, 30 mM of Tris p.H 7.4, 50 μl of 5 μg phosphotidylserine) at 30° C. in a water bath for 5 minutes. The reaction was terminated by placing the samples in ice. The PKC-ι inhibitor 1H-imidazole-4-carboxamide, 5-amino-1-[2,3-dihydroxy-4-[(phosphonooxy) methyl]cyclopentyl]-,[1R-(1a,2b,3b,4a)] (ICA-1; 100 nM) was synthesized by Southern Research Institute (Birmingham, Ala.).

The first negative control was immunoprecipitated with normal rabbit IgG beads with cell lysates (50 μg); the second negative control included cell lysate (50 μg) plus normal rabbit IgG (5 μg). The kinase reaction was performed as described above. Protein samples were separated by 10% SDS-PAGE and electroblotted onto supported nitrocellulose paper. Each blot was blocked for 1 h with 5% fat-free milk TTBS solutions at room temperature.

Protein bands were probed with their respective primary antibody p-IKKα/β rabbit polyclonal antibody (5 μg, 1:1000 dilution). Mouse monoclonal PKC-ι (5 μg, 1:1000 dilution). All the Immuoreactive bands were visualized with chemiluminescence according to the manufacturers' instructions (SuperSignal West Pico Chemiluminescent Substrate; PIERCE, Rockford, Ill.).

EXAMPLE 1

PKC-ι is Overexpressed in Malignant or Neoplastic Prostate Tissues

The relationship between the absence of PKC-ι in BPH tissue and its robust presence in malignant prostate tissue is summarized in Table 1. Western blots probing for PKC-ι in 6 BPH biopsies, 3 PIN, and 7 malignant tumors revealed absence of PKC-ι in BPH (Table 1). By comparison, PKC-ι was robustly present in two PIN and absent in one. PKC-ι was abundant in all malignant prostate tissue. Western blots corresponding to some of the data present in Table 1 are shown in FIGS. 1A and 1B. PKC-α and PKC-ι were identified in Western blots by bands with molecular weights of 80 kD and 67 kD, respectively which corresponded to the immunoreactive signal obtained from U-373MG glioma cells which contain PKC-α and PKC-ι (data not shown). Western blot controls for PKC-α did not show a pattern of expression specific to BPH, PIN or malignant prostate tumors. Control β-actin Western blots showed β-actin immunoreactive bands at a molecular weight of 42 kD. The β-actin immunoreactive bands were of equal intensity, indicating that equal amount of protein were loaded into each lane. The data presented in Table 1 and FIGS. 1A and 1B are also graphed in FIG. 1C which depicts a 100 fold increase in PKC-ι immunoreactivity in malignant prostate tissue when compared to BPH tissue. This data was subjected to a student's T-test and the level of PKC-ι in BPH tissue differed from that in malignant prostate (P=0.00048) and there was also a difference between normal prostate tissue and PIN (P=0.0357). This study demonstrates that PKC-ι is overexpressed in malignant prostate tissue and in some PIN compared to BPH tissues.

TABLE 1

Status of PKC-ι in BPH, PIN and malignant prostate tissues*

| Tissue Type | Not Present | Weakly Present | Positively Present |
|---|---|---|---|
| BPH | 6 | 0 | 0 |
| PIN | 1 | 0 | 2 |
| Malignant Prostate | 0 | 0 | 7 |

*Prostate tissue was obtained from prostate chips or prostatectomy.

Subsequently, immunohistochemistry was performed to address the query of the intracellular localization of PKC-α and PKC-ι. The immunohistochemistry data illustrates that PKC-α was expressed in the stromal cells but none to minimal expression was noted in majority of the benign glands (FIG. 10A), adenocarcinoma glands (FIG. 10C), and glands with HGPIN. In only one case the adenocarcinoma glands showed moderate expression of PKC-α. These adenocarcinoma glands expressing PKC-α had a Gleason pattern 4 (Table 2). It is speculated that the increase in PKC-α expression may be due to gene amplification or genetic duplication of PKC-α.

Figure 10:
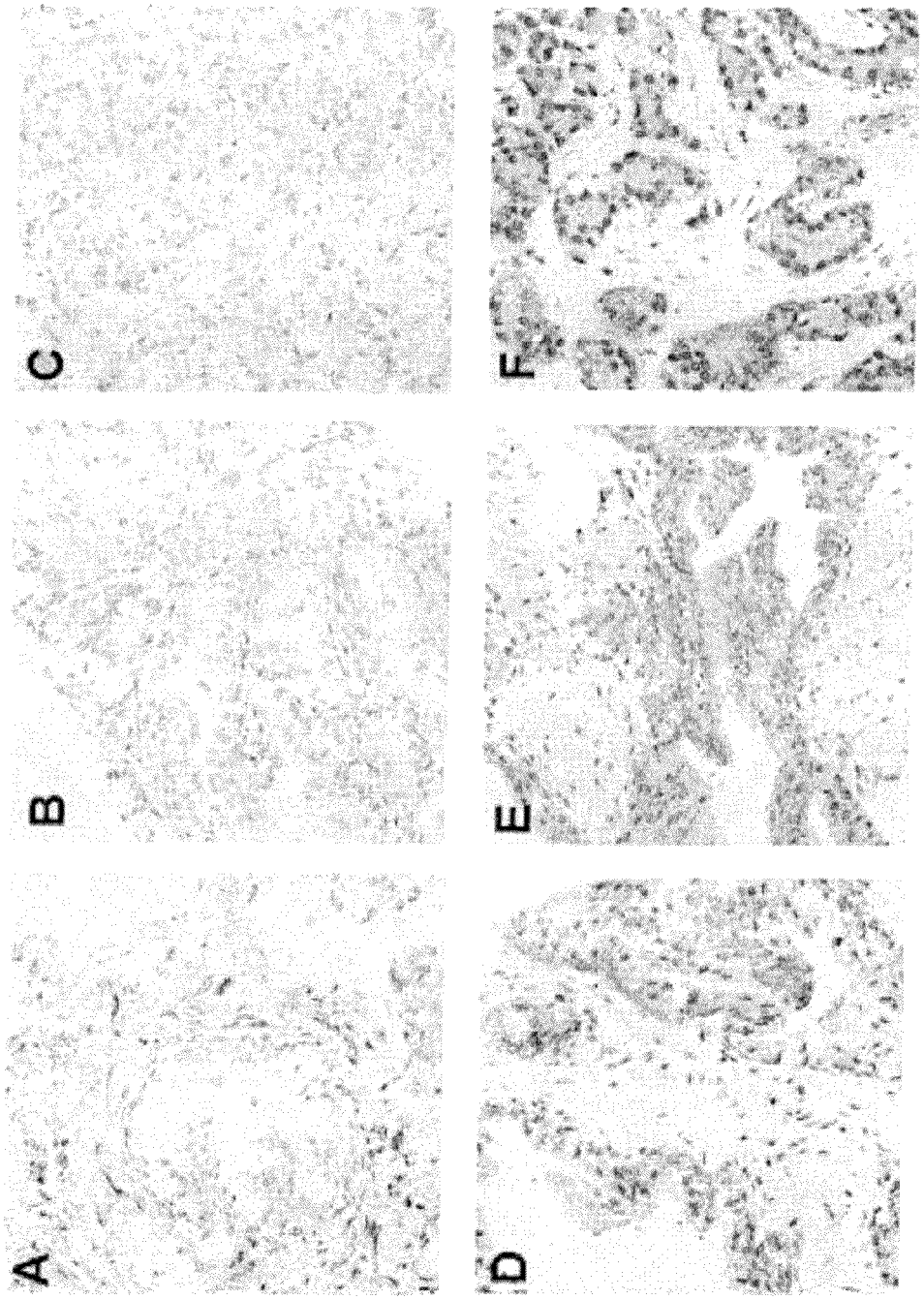
FIG. 10 are photographic results of immunohistochemistry studies of PKC-α and PKC-ι in benign, high grade PIN and malignant prostate tissue. Tissue was stained with PKC-ι antibody as a control for PKC-ι staining. Results depict PKC-ι staining in (A) benign prostate tissue, (B) high grade PIN (HGPIN), and (C) prostate adenocarcinoma. PKC-ι staining is illustrated for (D) benign prostate glands, (E) glands with HGPIN, and (F) prostatic adenocarcinoma glands. Results are representative of 9 benign prostate tissues, 8 HGPINs and 10 adenocarcinoma examined Magnification for all micrographs was ×400.

In contrast, PKC-ι expression was noted in all glands (proportion score of 5 in the majority of cases; Table 2 and FIG. 10F), however the intensity of staining was more in the adenocarcinoma glands with Allred scores of +8 and +7 (Table 2 and FIG. 10F) compared to benign glands (FIG. 10D) and glands with HGPIN (FIG. 10E and Table 2). The benign glands showed similar weak staining in samples obtained from patients with and without prostatic adenocarcinoma. The stromal cells had weak to moderate staining in samples with and without adenocarcinoma.

EXAMPLE 2

Immunoblot analysis of PKCs in siRNA Treated Prostate Cells

Figure 2:
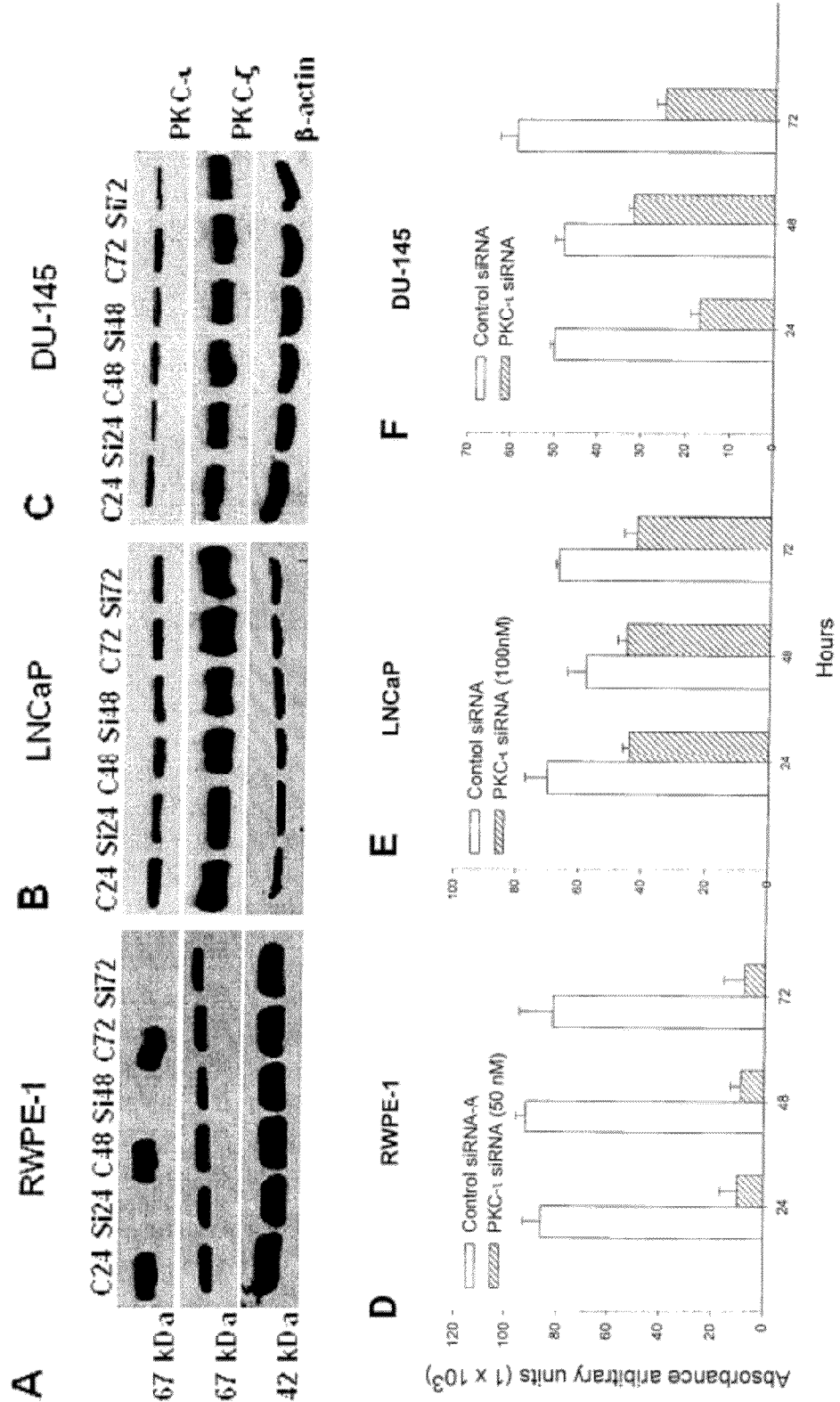
FIG. 2 is an immunoblot of three prostate cell lines following either no treatment or treatment with siRNA. Each cell line was harvested at 24 h, 48 h, or 72 h and protein blotted for the effects of either PKC-ι or PKC-ζ siRNA treatment. The figure also illustrates a graphical representation in absorbance units of the immunoblot results.
Figure 3:
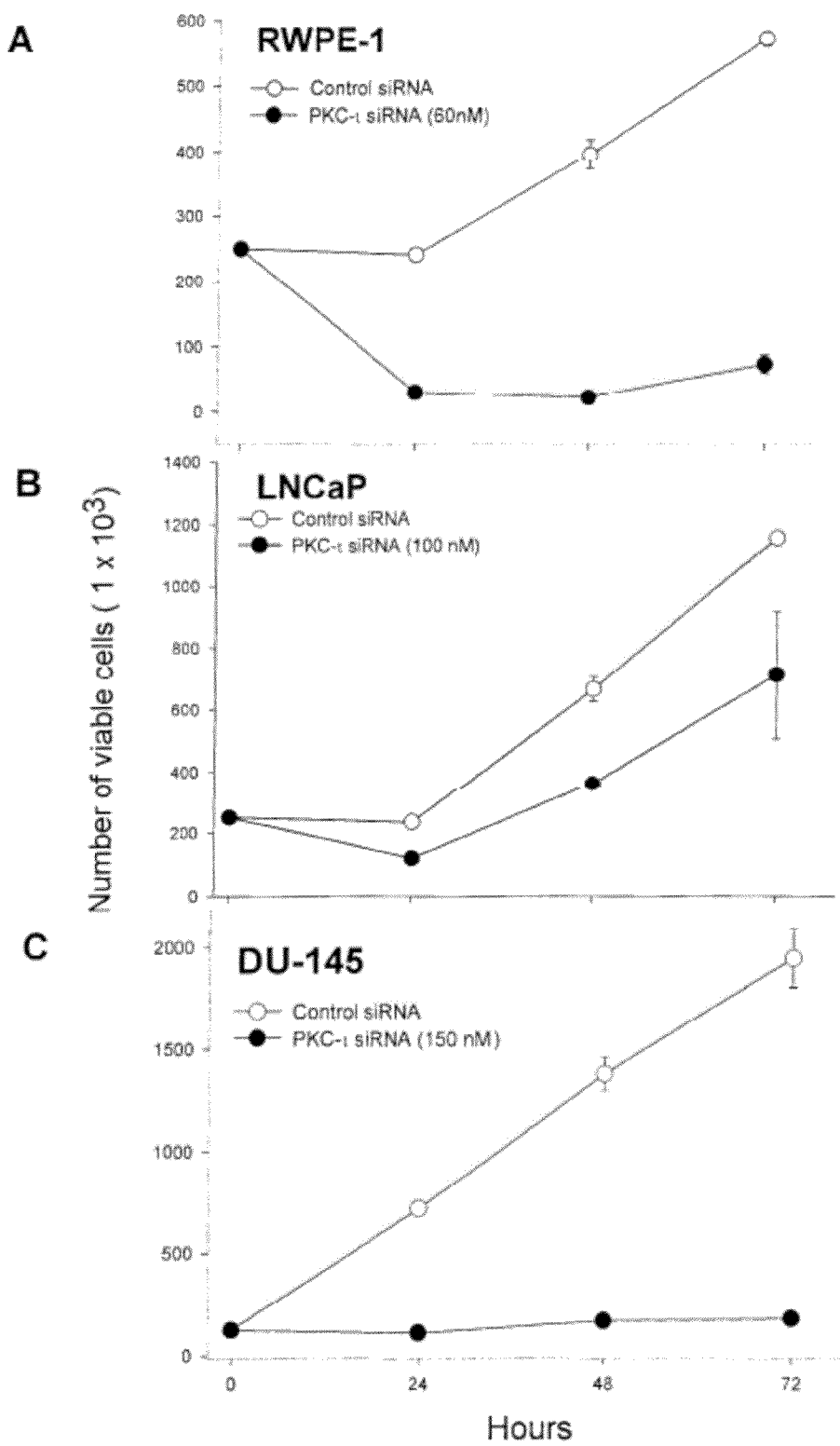
FIG. 3 details graphically the cellular viability of the three prostate cell lines following either no treatment or treatment with PKC-ι siRNA.

Immunoblotting of PKC-ι expression shows no effect in control siRNA (See FIG. 2 A-C). After counting the cells (from FIG. 3), the same populations of treated cells were immunoblot for PKC-ι, as described in "Materials and Methods." A protein concentration of 15 µg was loaded on each lane for each time point and separated by SDS-PAGE and Western blotted with anti-PKC-ι mouse monoclonal or anti-PKC-ζ rabbit polyclonal antibody. Immunoblotting for PKC-ι in PKC-ι siRNA treated RWPE-1 cells showed that expression decreased by 90-92%. Absorbance densitometry (FIGS. 2A and 2D) shows the average of three independent PKC-ι immunoblot for both RWPE-1 cell treatments (p=0.013, 0.005, 0.029). To show specificity, we immunobloted for PKC-ζ isoforms which is 98% identical to PKC-ι (FIG. 2A, second row).

There was no or very little PKC-ι present in PKC-ι siRNA treated cells compared to control siRNA. Furthermore, PKC-ι siRNA has no or very little effect on PKC-ζ indicating specificity (A-C). Stated another way, the PKC-ι siRNA effect was isospecific to the PKC-ι isozyme and did not affect the atypical PKC-ζ isoforms. Similarly, LNCaP cells were treated with control siRNA and PKC-ι siRNA (100 nM). However, there was no significant decrease in cell number (FIG. 3B).

Their p values were p=0.038, 0.096, 0.269 respectively. The siRNAs concentration was not increased due to some toxicity to cells. There was a slight decrease in LNCaP control cells post 24 hour transfection but later cells grew back between 24-72 hour. Immunoblot of PKC-ι shows no significant decrease in PKC-ι compare to control siRNA (p=0.138, 0.050, 0.560) (FIGS. 2B and E). Therefore, the cells continue to proliferate. PKC-ι siRNA did not affect PKC-ζ isoforms (FIG. 2A-C, second row).

Figure 5:
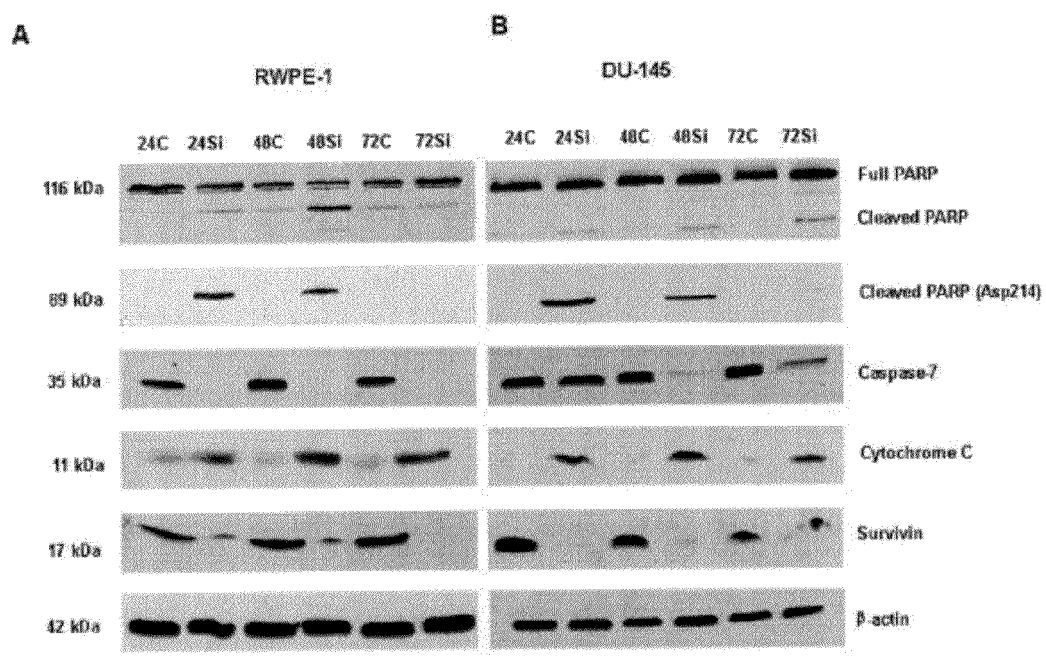
FIG. 5 is an immunoblot corresponding to known apoptotic cascade proteins of two prostate cell lines following either no treatment or treatment with PKC-ι siRNA.

In accordance with our hypothesis that PKC-ι may be antiapoptotic and required for cell survival in DU-145 cells. Treatment with PKC-ι siRNA (150 nM) showed a decrease in cell viability by more than 80% compared to control siRNA (p=0.002, 0.006, 0.004) (FIG. 5.2C). Immunoblotting for PKC-ι in PKC-ι siRNA treated DU-145 cells demonstrated a decrease in PKC-ι expression by 60-70% between 24-72 hours (FIG. 2C). The PKC-ι siRNA effect was isospecific to the PKC-ι isozyme and did not affect atypical PKC-ζ isoforms (FIG. 2C, second row). Absorbance densitometry (FIG. 2F) compared the effects of PKC-ι siRNA and show the average of three independent PKC-ι immunoblot for DU-145 cells (p=0.001, 0.022, 0.015).

EXAMPLE 3

PKC-ι siRNA Treatment Decreases Prostate Cell Viability and Inhibits Cell Cycle Progression To provide additional evidence that PKC-ι is required for cell proliferation in RWPE-1 cells, PKC-ι was temporarily inhibited using PKC-ι siRNA. Subconfluent RWPE-1 (A), LNCaP (B) and DU-145 (C)cells ($2.5 \times 10^5$) were treated with PKC-ι siRNA (50 nM for RWPE-1, 100 nM for LNCaP and 150 nM for DU-145) complex from 24-72 h as described in "Materials and Methods." At the indicated time, the viable cells were counted using trypan blue exclusion assay and a hematocyometry. Three independent experiments were performed and the mean of the viable cells and SD were plotted. After titrating PKC-ι siRNA concentrations from 50-100 nM, we used an optimal concentration of PKC-ι siRNA (50 nM) and control siRNA to suppress PKC-ι expression. It was shown that there is a decrease in cell proliferation in PKC-ι siRNA treated cells compared to control siRNA (FIG. 3A-C). Their standard values were as follow: RWPE-1 (0.005, 0.004, 0.001); LNCaP (0.038, 0.098, 0.269); DU-145 (0.002, 0.006, 0.004). Treatment with PKC-ι siRNA (50 nM) decreased the number of viable cells by 87-96% after 24-72 hours (p=0.005, 0.004, 0.001 respectively) compared to control cells (FIG. 3A). However, transfection with siRNA complex creates some toxicity to RWPE-1 cells. The control viable cells were lower than the number of original cells plated at 24 h time point but it was overcome over the 24 h of incubations.

Tables 2 and 3 show a numerical representation of the cell cycle data performed by flow cytometry. We established by flow cytometery (data not shown) which cell cycle phase was disrupted by treatment with PKC-ι siRNA. RWPE-1 cell cycle analysis showed a 44-63% decrease in S-phase and a more than two-fold increase in $G_2/M$ phase compared to control siRNA throughout the time period (Table 2). Thus, PKC-ι siRNA inhibits $G_2/M$ cell cycle phase in RWPE-1. However, in DU-145 cells, PKC-ι siRNA increased the $G_0/G_1$ phase by 34-36%, and decreased the DNA synthesis (S-phase) by 41-44% throughout the time course (Table 3). Hence, PKC-ι siRNA inhibited the $G_1/S$ transition in DU-145 cells.

TABLE 2

Summary of non-malignant prostate, RWPE-1, cell cycle phases after treatment with control siRNA and PKC-ι siRNA at indicated time*

| Time (h) | $G_0/G_1$ Control | $G_0/G_1$ siRNA | S Control | S siRNA | $G_2/M$ Control | $G_2/M$ siRNA |
|---|---|---|---|---|---|---|
| 24 | 59 +/− 1 | 63 +/− 1 | 32 +/− 1 | 18 +/− 1 | 8 +/− 1 | 20 +/− 1 |
| 48 | 56 +/− 1 | 70 +/− 1 | 36 +/− 1 | 13 +/− 1 | 15 +/− 4 | 18 +/− 2 |
| 72 | 59 +/− 2 | 67 +/− 1 | 32 +/− 2 | 12 +/− 1 | 9 +/− 1 | 22 +/− 2 |

*N = 3 independent experiments

TABLE 3

Summary of androgen-independent prostate carcinoma, DU-145, cell cycle phases after treatment with control siRNA and PKC-i siRNA at indicated time*

| Time (h) | $G_0/G_1$ Control | $G_0/G_1$ siRNA | S Control | S siRNA | $G_2/M$ Control | $G_2/M$ siRNA |
|---|---|---|---|---|---|---|
| 24 | 45 +/− 1 | 61 +/− 1 | 41 +/− 2 | 23 +/− 4 | 14 +/− 3 | 16 +/− 3 |
| 48 | 47 +/− 2 | 63 +/− 5 | 39 +/− 5 | 23 +/− 7 | 14 +/− 4 | 15 +/− 2 |
| 72 | 54 +/− 3 | 57 +/− 5 | 33 +/− 5 | 25 +/− 6 | 13 +/− 3 | 17 +/− 2 |

*N = 3 independent experiments.

EXAMPLE 4

PKC-ι siRNA Treatment Induces Apoptosis in Prostate Cells

Figure 4:
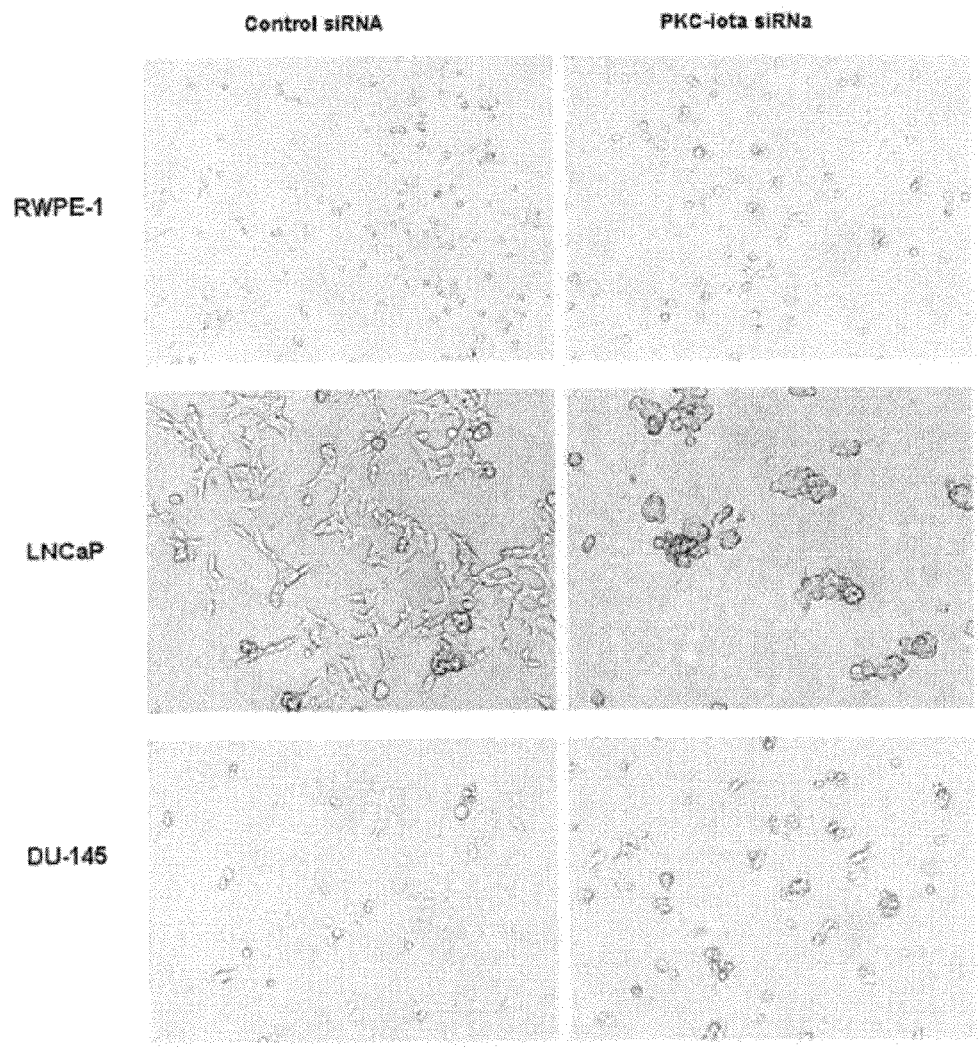
FIG. 4 depicts a microscopic view of the three prostate cell lines following either no treatment or treatment with PKC-ι siRNA.

We have shown that PKC-ι siRNA inhibits cell cycle phase in RWPE-1 and DU-145 cells. The cells were also observed under phase contrast microscopy. The cells treated with PKC-ι siRNA depicted cell rounding, cell membrane blebbing, chromatin condensation and lifting of cells from the flask, indicating cell death compared to control cells (FIG. 4).

After transfecting the cells with control siRNA or PKC-ι siRNA were analyzed by western blot for full PARP. Full PARP rabbit polyclonal antibody detected full PARP 113 kDa and activation of PARP (i.e cleaved PARP) at 89 kDa. RWPE-1 cells showed no significant changes in full PARP. In contrast, there was activation of PARP 89 kDa protein at 24 h siRNA treated cells and more significantly at the 48 h time point of siRNA treated cells (FIG. 5A-B). However, no significant changes occurred at 72 h time point. Similarly, control DU-145 cells shows no changes in full PARP protein level but there was significant activation of PARP at 24-72 h in siRNA treated cells compared to control siRNA (FIG. 5B). Hence, activation of PARP confirmed that there is DNA damage, indicating apoptosis in RWPE-1 and DU-145 cells.

PKC-ι siRNAs Treatment Activates Apoptosis Cascades in RWPE-1 and DU-145 cells.

Next, we showed that PKC-ι siRNA treatment provokes 'intrinsic' apoptosis. Fifteen microgram of whole cells lystates from both control and PKC-ι siRNA treated cells were run on 15% SDS-PAGE and Western blotted for cytochorme c. The increase in cytochrome c was observed in all the PKC-ι siRNA treated RWPE-1 cells and DU-145 cells (FIG. 5). To demonstrate activation of caspases during apoptosis, whole cell lysate (100 μg) of PKC-ι siRNA treated cells together with control cells were Western blotted for caspase-7. In RWPE-1, a decrease in pro-caspase-7 was observed at 24-72 h of PKC-ι siRNA treated cells. In contrast, the control siRNA treated cells showed the presence of pro-caspase-7 protein. However, in DU-145 PKC-ι siRNA treated cells a decrease in pro-caspase-7 was observed in time dependent manner at the 42 h and 72 h time points (FIG. 5B).

In addition, we also Western blotted for survivin protein (15 μg) in both cell lines after treatment with PKC-ι siRNA. There was a higher level of survivin in control cells compared to PKC-ι siRNA treated cells. Western blot of β-actin verified that protein loading for each sample was equal. All the Western blots were taken from the best of three independent experiments (FIG. 5).

Effects of PKC-ι siRNA on LNCaP Cells

Figure 6:
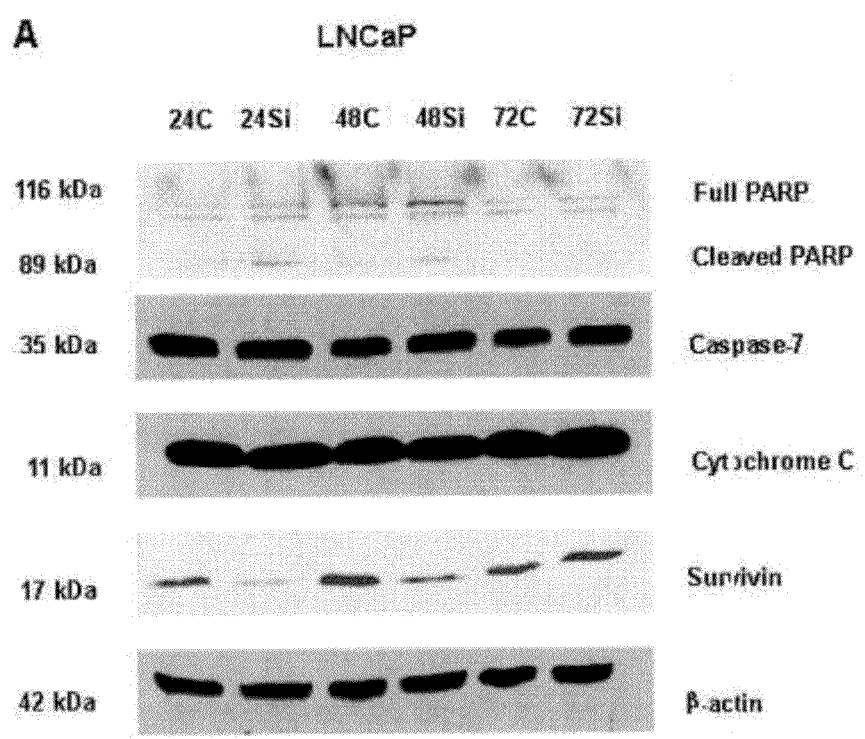
FIG. 6 is an immunoblot corresponding to known apoptotic cascade proteins of another prostate cell line following either no treatment or treatment with PKC-ι siRNA.

Similarly, LNCaP cells were analyzed for apoptosis although there was no significant reduction in cell proliferation (FIG. 6). Whole cell lysate of 15 μg was used to analyze for Full PARP and cleaved PARP. PKC-ι siRNA treated cells showed an activation of PARP (i.e. cleave PARP) at 24 h and 48 h time points. However, caspase-7 activation was not observed in both control and PKC-ι siRNA treated cells. In addition, there was no significant change in cytochrome c expression. However, a decrease in survivin was observed at 24 h and 48 h in PKC-ι siRNA treated cells.

Effects of siRNA on RWPE-1 Cdk7 and cdk2

Figure 7:
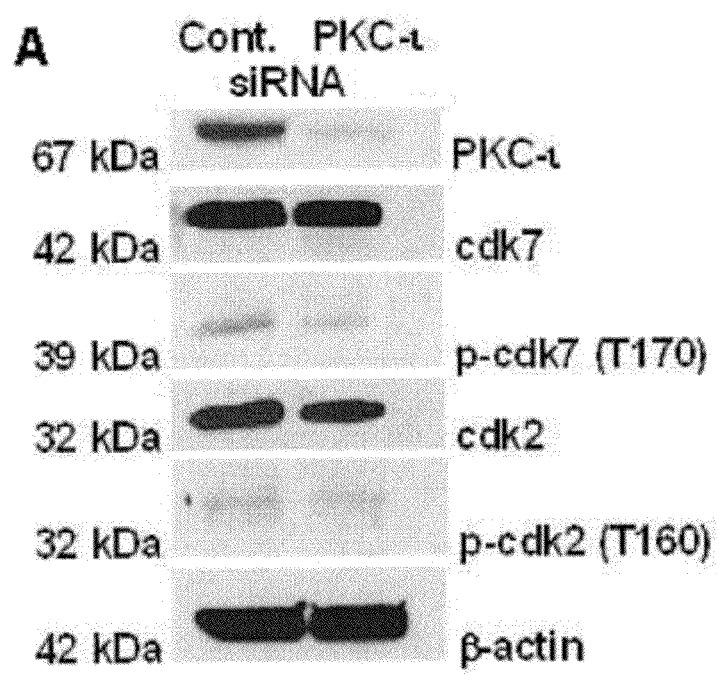
FIG. 7 corresponding to known cellular proliferation pathway proteins of a prostate cell line following either no treatment or treatment with PKC-ι siRNA.

Previously we have shown the association between PKC-ι and Cdk-7 in RWPE-1 cells. We next determined if treatment of PKC-ι siRNA impaired the cell proliferation pathway (PKC-ι→Cdk7→cdk2). The cells were incubated with PKC-ι siRNA complex for 48 h and 15 μg of whole cell lysates were Western blotted for PKC-ι Cdk7 and cdk2. There was a significant decrease in PKC-ι expression in PKC-ι siRNA treated cells compared to control siRNA tread cells (FIG. 7). There was no change in Cdk7 and cdk2 expression. One hundred and fifty micrograms of whole cell lysate was used for Western blotting of phosphorylation of Cdk7 and cdk2. We found that there was a significant changes in phosphorylation of Cdk7 (Th170) and cdk2 (Th160) in PKC-ι siRNA treated cells compared to control siRNA. Western blot of O-actin verified equal loading of protein in each sample.

PKC-ι siRNA Effects on Phosphorylation Status of Bad and Bad/Bcl-$x_L$ Heterodimerization PKC-ι is overexpressed in non-small cell lung cancer cells (NSCLC) and it has been reported to phosphorylate Bad at multiple sites for cell survival. To test whether PKC-ι can directly phosphorylate endogenous Bad, Bad protein (200 µg) was immunoprecipitated from control siRNA and PKC-ι siRNA treated (incubation time 24 h) RWPE-1 and DU-145 cells. Normal rabbit IgG agarose conjugate (5 µg) was used as a negative control. Results demonstrated no detectable association between PKC-ι and BAD. We also increased the protein level and performed reverse immunoprecipitation with PKC-ι antibody, but no association of Bad with PKC-ι was observed. Whereas immunoblot with phospho specific Bad (ser-112, ser-155, ser-136) showed no significant changes in phospho Bad ser-112, phosphorylation of Bad ser-155 and ser-136 decreased in RWPE-1 cells (FIG. 8A; second column).

Figure 8:
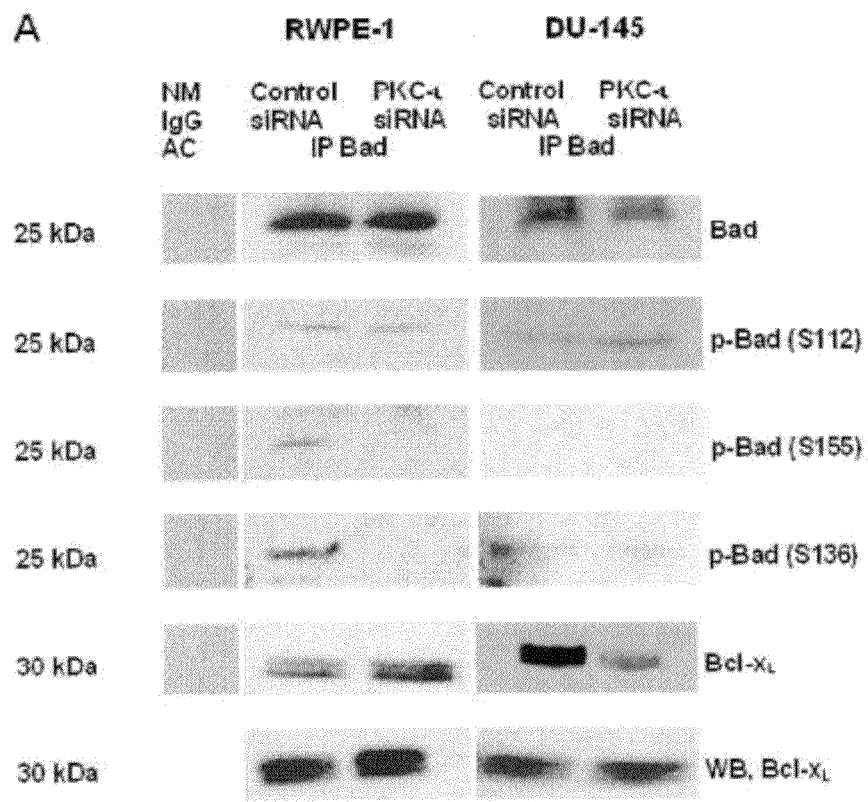
FIG. 8 is an immunoblot corresponding to known apoptotic cascade proteins of two prostate cell lines following either no treatment or treatment with PKC-ι siRNA.
Figure 8:
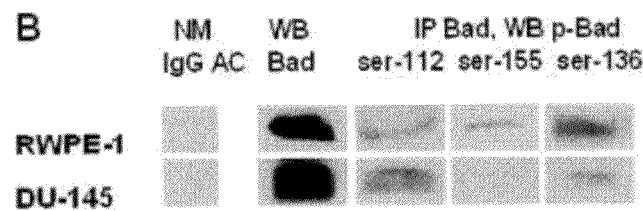

A similar experiment was performed with DU-145 (FIG. 8A, third column). First, we investigated if PKC-ι associates with Bad. Our result showed no association of PKC-ι and Bad (data not shown). However, we observed an increase in phosphorylation of Bad ser-112, no significant changes in p-Bad (ser-136) and p-Bad (ser-155).

Our results also showed the disruption of Bad/Bcl-$x_L$ heterodimerization in PKC-ε siRNA treated cells compared to control siRNA but the anti-apoptotic protein level of Bcl-$x_L$ remained the same. The disruption of Bad/Bcl-$x_L$ heterodimerization may play a critical role in mitochondria dysfunction and apoptosis in PKC-ι siRNA treated cells. We also found that there were different levels of phosphorylation of Bad RWPE-1 and DU145 cells (FIG. 8A). All three phospho serine sites (112, 155, 136) on Bad protein are expressed endogenously in RWPE-1 cells while DU-145 cells have only two p-Bad (ser-112 and ser-136) (FIG. 8B). Collectively, these results suggest that in DU-145 cells, phosphorylation of Bad (deactivation/survival) was not able to rescue the cells from PKC-ι siRNA induced apoptosis.

EXAMPLE 5

In Vivo Kinase Assay and ICA-1 Effects on Prostate Cells

Figure 9:
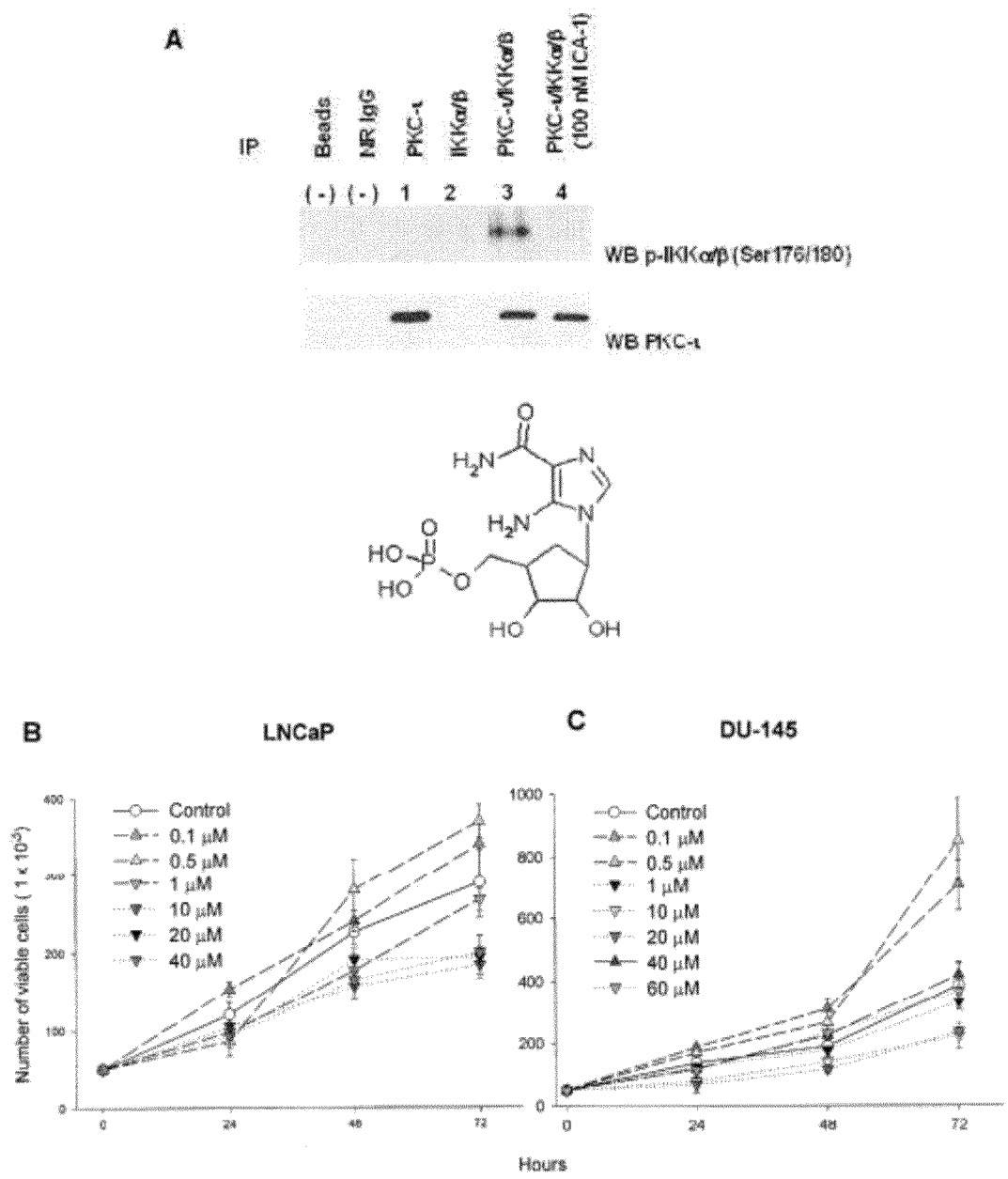
FIG. 9 is an immunoblot following immunoprecipitation that analyzes the effects of the PKC-ι inhibitor ICA-1. Further, the figure includes cellular viability graphs of two prostate cell lines either treated or treated with varying dosages of the PKC-ι inhibitor ICA-1.

It has been demonstrated that PKC-ι/ζ phosphorylates IKKα/β (Duran et al., 2003). To further demonstrate that IKKα/β is a true substrate of PKC-ι, IKKα/β and PKC-ι were co-immunoprecipitated and Western blots of p-IKKα/β (Ser176/180) demonstrated that PKC-ι, phosphorylates IKKα/β (FIG. 9). Cell lysates (50 µg) of an exponentially growing DU-145 cells were immunoprecipitated with either rabbit polyclonal PKC-ι antibody and/or IKKα/β rabbit polyclonal antibody. Lane 1 and 2 are the two negative controls: first is the sepharose beads (50 µl of 1:1 v/v), the second negative control contains sepharose beads (50 µl) and normal rabbit IgG. After immunoprecipitation, a kinase reaction was performed according to "Materials and Methods". Western blot analysis showed presence of phospho-IKKα/β (Ser176/180) in lane 3. Upon incubation with PKC-ι inhibitor (ICA-1; 100 nM) phosphorylation of IKKα/β was inhibited. In FIG. 9B, LNCaP and DU-145 cells (C) (50×10$^4$) were seeded in a T25 flask. After incubation for 24-72 hours with ICA-1 (0.1 µM-60 µM), both the control cells and ICA-1 treated cells were trypsinized and viable cells were counted using trypan blue exclusion assay and a hematocytometry. Triplicate experiments were performed for each cell line. The mean values of viable cells with SD were plotted. P>0.05 demonstrated an insignificant effect of ICA-1 on cell proliferation.

Little or no activation of IKKα/β was observed in control immunoprecipitated PKC-ι or IKKα/β samples. Additionally, activation of IKKα/β was inhibited when the putative PKC-ι inhibitor ICA-1 (100 nM) was incubated in co-immunoprecipitated PKC-ι and IKKα/β. The inhibitor binds to the kinase domain amino acid sequence 469-475.

However, ICA-1 does not significantly (p>0.05 for both cell lines) inhibit the cell proliferation of LNCaP or DU-145 cells (FIGS. 9B and C). Interestingly, low concentration of ICA-1 (0.1-0.5 µM) resulted in an increase in cell numbers while high concentration of ICA-1 (10-60 µM) resulted in a inhibition of cell growth. Thus ICA-1 can be an activator at low concentration and an inhibitor at high concentration.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Agrawal D, Dong F, Wang Y-Z, Kayda D, and Pledger W J. (1995) Regulation of Cyclin E and p27$^{Kip}$ during mitosis in BALB/c 3T3 cells. Cell Growth Diff. 6:1199-1205.

Allred D C, Harvey J M, Berardo M, et al: Prognostic and predictive factors in breast cancer by immunohistochemical analysis. Mod Pathol 11:155-168, 1998.

Bradford M M. (1976) A rapid and sensitive method for the quantitation of microgram quantities of protein utilizing the principle of protein-dye binding. Anal. Biochem. 72, 248-254.

Cornfor P, Evans J, Dodson A, Parsons K, Woolfenden A, Neoptolemos J, and Foster C S. Protein kinase C isozymes patterns characteristically modulated in early prostate cancer. American Journal of Pathology 154:137-144, 1999.

Davies A M, Gandara D, Lara P, Mack P, Lau D, Gumerlock P. (2003) Antisense oligonucleotides in the treatment of NSCLC. Clinical Lung Cancer 4:S68-S73.

Dean N M, McKay R, Condon T P, Bennett C F. (1994) Inhibition of protein kinase C-alpha expression in human A549 cells by antisense oligonucleotides inhibits induction of intercellular adhesion molecule 1 (CAM-1) mRNA by phorbol-esters. The Journal of Biological Chemistry 269:16416-24.

Diaz-Meco, M. T., Municio, M. M., Sanchez, P., Lozano, J. and Moscat, J. (1996). Lamda-interacting protein, a novel protein that specifically interacts with the Zinc finger domain of the atypical Protein Kinase C isotype λ/ι and stimulates its kinase activity in vitro and in vivo. Molec. and Cell Bio., 16, 105-114.

Duran A, Diaz-Meco MT and Moscat J. Essential role of Rel Ser311 phosphorylation by ζPKC in NF-κB transcriptional activation. The EMBO Journal 22:3910-3918, 2003.

Dutil E M, Toker A, and Newton A C. (1998) Regulation of conventional protein kinase C isozymes by phosphoinositide-dependent kinase 1(PDK-1). Current Biology 8:1366-1375.

Eder, A. M, Sui, X., Rosen, D. G., Nolden. L. K., Chen, K. W., Lahad, J. P., Kango-Singh, M., Lu, K. H., Warneke, C. L., Atkinson, E. N., Bedrosian, I., Keyomarsi, K., Kuo, W-I., Gray, J. W., Yin, J. C. P., Lui, J., Halder, G., Mills, G. B. (2005) Atypical PKCi contributes to poor prognosis through loss of apical-basal polarity and Cyclin E overexpression in ovarian cancer. PNAS 102:12519-12524.

Edwards A S, Faux M C, Scott J D, and Newton A C. (1999) Carboxyl-terminal phosphorylation regulates the function and subcellular localization of protein kinase C bII. J. Biol. Chem. 274:6461-6468.

Flescher E, Rotem R. (2002) Protein kinase C ε mediates the induction of p-glycoprotein in LNCaP prostate carcinoma cells. Cellular Signalling 14:37-43.

Fujii T, Garcia-Bermejo M L, Bernabo J L, Caamano J, Ohba M, Kuroki T, Li L, Yuspa S H, and Kazanietz M G. (2000) Involvement of protein kinase C (PKCδ) in phorbol ester-induced apoptosis in LNCaP prostate cancer cells. The Journal of Biological Chemistry 275:7574-7582.

Garcia-Bermejo M L, Leskow F C, Fujii T, Wang Q, Blumberg P M, Ohba M, Kuroki T, Han K, Lee J, Marquez V E, and Kazanietz M G (2002). Diacylglycerol (DAG)-lactones, a new class of protein kinase C (PKC) agonists, induce apoptosis in LNCaP prostate cancer cells by selective activation of PKC-α. The Journal of Biological Chemistry 244:645-655.

Gonzalex-Guerrico A M, Meshki J, Xiao L, Benavides F, Conti C J and M. G. Kazanietz. (2005) Molecular mechanisms of protein kinase C-induced apoptosis in prostate cancer cells. Journal of Biochemistry and Molecular Biology 38:639-645.

Gross A, McDonnell J M and Korsmeyer S J. Bcl-2 family members and the mitochondria in apoptosis. Genes Development 13: 1899-1911, 1999.

Hallahan D E, Virudachalam S, Grdina D. et al. (1992) The isoquinoline sulfonamide H7 attenuates radiation-mediated protein kinase C activation and delays the onset of x-ray induced G2 arrest. J. Radiat. Oncol. Biol. Phys. 24:687-692.

Hayashi A., Seki N, Hattori A, Kozuma S, Saito T. (1999) PKCη, a new member of the protein kinase C family, composes a fourth subfamily with PKCμ. Biochim et Biophys Acta 1450, 99-106.

Hirai T, Niino Y, Chida K. (2003) PKCII, a small molecule of protein kinase C ζ, specifically expressed in mouse brain. Neuroscience Lett, 348, 151-154.

Housey G M, Johnson M D, Hsiao W L M, et al. (1988) Overproduction of protein kinase C causes disordered growth control in rat fibroblasts. Cell 52:343-354.

Inoue T, Yoshida T, Shimizu Y, Kobayashi T, Yamasaki T, Toda Y, Segawa T, Kamoto T, Nakamura E, and Ogawa O. (2006) Requirement of androgen-dependent activation of protein kinase Cζ for androgen-dependent cell proliferation in LNCaP cells and its roles in transition to androgen-independent cells. Molecular Endocrinology 20:3053-3069.

Jaggi M, Rao P S, Smith D J, Hemstreet G P, and Balji K C. (2003) Protein kinase Cμ is down-regulated in androgen-independent prostate cancer. Biochemical and Biophysical Research Communications 307:254-260.

Kamata T, Sullivan NF and Wooten M W. (1987) Reduced protein kinase C activity in a ras-resistant cell line derived from Ki-MSV transformed cells. Oncogene 1:37.

Keranen L M, Dutil E M, and Newton A C. (1995) Protein kinase C is regulated in vivo by three functionally distinct phosphorylations. Current Biology 5:1 394-1403.

Kharait S, Dhir R, Lauffenburger D, Wells A. (2006) Protein kinase Cδ signaling downstream of the EGF receptor mediates migration and invasiveness of prostate cancer cells. Biochemical and Biophysical communications 343:848-856.

Lahn M, Sundell K, Gleave M, Lada F, Su C, Lit S, Ma D, Paterson D M and Bumol T F. (2004) Protein kinase C-α in prostate cancer. British Journal of Urology International 93:1076-7081.

Lamm M L, Long D D, Goodwin S M, Lee C. (1997) Transforming growth factor-beta1 inhibits membrane association of protein kinase C alpha in a human prostate cancer cell line, PC3. Endocrinology 138:4657-4664.

Li Q, Wang J M, Liu C, Xiao B L, Lu J X, Zou S Q. (2008) Correlation of aPKC-iota and E-cadherin expression with invasion and prognosis of cholangiocarcinoma. Hepatobiliary Pancreat Dis Int. 7:70-75.

Mizuguhi J, Makabayashi H, Yoshida Y. et al. (1988). Increased degradation of protein kinase C without diminution of mRNA level after treatment of WEHI-231 B lymphoma cells with phorbol esters. Biochem. Biophy. Res. Commun. 155:1311-1317.

Murray N R, Fields A P. (1997) Atypical Protein Kinase C iota Protects Human Leukemia Cells against Drug-induced Apoptosis. J Biol Chem 272:27521-27524.

Nishizuka, Y. (1992) Intracellular signally by hydrolysis of phospholipids and activation of protein kinase C. Science, 258, 607-614.

Oxley J E, Winkler M H, Gillatt D A, Peat D S. (2002) Her-2/neu oncogene amplification inclinically localized prostate cancer. Journal of Clinical Pathology 55:118-120.

Patel, R., Win, H., Desai, S. Patel, K., Matthews, J. A. and Acevedo-Duncan, M. (2008) Involvement of PKC-ι in Glioma Proliferation. Cell Proliferation 41:122-135.

Persons D A, Wilkison W O, Bell R M. et al. (1988) Altered growth regulation and enhanced tumorigenicity of NIH 3T3 fibroblasts transfected with protein kinase C-I DNA. Cell 52:447-458.

Powell C T, Birttis N J, Stec D, Hug H, Heston W D W, and Fair W R. (1996) Persistent membrane translocation of protein kinase Cα during 12-O-tetradecanoylphorbol-13-acetate-induced apoptosis of LNCaP human prostate cancer cells. Cell Growth and Differentiation 7:419-428.

Rao P S, Jaggi M, Smith D J, Hemstreet G P, and Balaji K C. (2003) Metallothionein 2A interacts with the kinase domain of PKC in prostate cancer. Biochemical and Biophysical Research Communications 310:1032-1038.

Regala, R. P., Weems, C., Jamison, L., Copland, J. A. Thompson, E. A., Fields, A. P. (2005) Atypical protein kinase ι plays a critical role in human lung cancer cell growth and tumorigenicity. J. Biol. Chem. 280:31109-31115.

Regala, R. P., Weems, C., Jamieson, L., Khoor, A., Edell, E. S., Lohse, C. M., Fields, A. P. (2005b) Atypical protein kinase ι is an oncogene in human non-small cell lung cancer. Cancer Res 65:8905-8911.

Rosenberg M and David S (2006). Protein kinase Cγ regulates myosin IIB phosphorylation, cellular localization, and filament assembly. Molecular Biology of the Cell 17:1364-1374.

Rusnak J M, and Lazo J S. (1996) Downregulation of protein kinase C suppresses induction of apoptosis in human prostatic carcinoma cells. Experimental Cell Research 224:189-199.

Selbie L A, Schmitz-Peiffer C, Sheng Y, Biden T. (1993) Molecular cloning and characterization of PKCiota, an atypical isoform of PKC derived from insulin-secreting cells. J Biol Chem, 268, 24296-24302.

Selzer, E., Okamoto, I., Lucas, T., Kodym, R., Pehamberger, H., and Jansen, B. (2002). Protein Kinase C isoforms in normal and transformed cells of the melanocytic lineage. Melanoma Research 12, 201-209.

Shih A, Zhang S, Cao H J, Boswell S, Wu Y, Tang H, Lennartz M R, Davis F B, Davis P J, and Lin H. (2004) Inhibitory effect of epidermal growth factor on resveratrol-induced apoptosis in prostate cancer cells is mediated by protein kinase C-α. Molecular Cancer Therapeutics 3:1355-1363.

Stewart J R and O'Brian C A. (2005) Protein kinase C-α mediates epidermal growth factor receptor transactivation in human prostate cancer cells. Molecular Cancer Therapeutics 4:726-732.

Towbin H, Staehelin T, and Gordon P E. (1979) Electrophoretic transfer of proteins form polyacrylamide gels to nitrocellulose sheets: Procedure and some applications. Proc. Natl. Acad. Sci. USA 76:4350-4354.

Weyman C M, Taparowsky E J, Wolfson M, et al. (1988) Partial down-regulation of protein kinase C in C3H10t1/2 mouse fibroblasts transfected with the human Ha-ras oncogene. Cancer Res. 48: 6535-6541.

Wu D, Thakore C U, Wescott G G, McCubrey J A and Terrian D M (2004). Integrin signaling links protein kinase C ε to the protein kinase B/Akt survival pathway in recurrent prostate cancer cells. Oncogene 23:5689-8672, 2004.

Xie J, Guo Q, Zhu H, Wooten M, Mattson M. (2000) Protein kinase C iota protects neural cells against apoptosis induced by amyloid beta-peptide. Mol Brain Res 82:107-113.

---

What is claimed is:

1. A method of diagnosing prostate cancer in a subject comprising:
   (a) obtaining a tissue sample from the prostate of a human subject;
   (b) determining in the sample a level of expression for PKC-ι, wherein said determining step comprises:
   contacting the sample with an antibody that recognizes PKC-ι protein in an immunoassay selected from western blot assay, enzyme-linked immunosorbent assay (ELISA), and immunohistochemical assay, and
   detecting the complex between the antibody and the PKC-ι protein;
   (c) comparing the expression level determined in (b) to a control, wherein the control is a level of expression of PKC-ι in a benign human prostate tissue; and
   (d) informing the human subject as having prostate cancer if the PKC-ι expression level determined in (b) is higher than the control or informing the human subject as not having prostate cancer if the PKC-ι expression level determined in (b) is lower than the control.

2. The method according to claim 1 wherein the determining determines the quantitative level of expression of PKC-ι in a prostate sample tissue.

3. The method according to claim 1 wherein said antibody is a monoclonal antibody.

4. The method according to claim 1 wherein said antibody is a polyclonal antibody.

5. The method according to claim 1 wherein said protein is contacted with said antibody in an enzyme-linked immunosorbent assay (ELISA).

6. The method according to claim 1 wherein said immunoassay is a western blot assay.

7. A method of providing treatment of prostate cancer to a human subject, comprising:
   (a) obtaining a tissue sample from the prostate of a human subject;
   (b) determining in the sample a level of expression for PKC-ι, wherein said determining: step comprises:
   contacting the sample with an antibody which recognizes PKC-ι protein; and
   detecting the complex between the antibody and the PKC-ι protein;
   (c) comparing the expression level determined in (b) to a control, wherein the control is a level of expression of PKC-ι in a benign human prostate tissue; and
   (d) providing treatment of prostate cancer to the human subject if the PKC-ι expression level determined in (b) is higher than the control.

8. The method according to claim 7 wherein said antibody is a monoclonal antibody.

9. The method according to claim 7 wherein said antibody is a polyclonal antibody.

10. The method according to claim 7 wherein said protein is contacted with said antibody in an immunoassay selected from the group consisting of radioimmunoassay, western blot assay, immunofluorescent assay, enzyme immunoassay, enzyme-linked immunosorbent assay (ELISA), immunoprecipitation, chemiluminescent assay, immunohistochemical assay, dot blot assay and slot blot assay.

11. The method according to claim 10 wherein said immunoassay is a western blot assay.

12. The method according to claim 10 wherein said immunoassay is an enzyme-linked immunosorbent assay (ELISA).

* * * * *

UNITED STATES PATENT AND TRADEMARK OFFICE
CERTIFICATE OF CORRECTION

PATENT NO. : 8,603,758 B2
APPLICATION NO. : 13/532364
DATED : December 10, 2013
INVENTOR(S) : Acevedo-Duncan et al.

It is certified that error appears in the above-identified patent and that said Letters Patent is hereby corrected as shown below:

In the Specification

Column 8,
Line 56, "meningal fluid" should read --meningeal fluid--.

Column 14,
Line 30, "PKC-ιcan" should read --PKC-ι can--.
Line 45, "PKC-L-directed" should read --PKC-ι-directed--.

Column 20,
Line 47, "for PKC- ι, or PKC- ι, may" should read --for PKC- ι, may--.

Column 22,
Line 30, "*Lab chip*," should read --*Lab Chip*,--.
Line 65, "phosohodiester" should read --phosphodiester--.

Column 29,
Line 53, "PKC-t" should read --PKC-ι--.

Column 32,
Lines 11-12, "(Elbashir S M. et al.," should read --(Elbashir, S.M., *et al.*,--.

Column 36,
Line 40, "ribozyrnes" should read --ribozymes--.
Line 61, "261:14111418" should read --261:1411-1418--.

Column 43,
Line 60, "pBAD/H is" should read --pBAD/His--.

Signed and Sealed this
Twenty-second Day of July, 2014

Michelle K. Lee
*Deputy Director of the United States Patent and Trademark Office*

Column 45,
Line 14, "procedures. in" should read --procedures. In--.
Line 34, "or tip," should read --or trp,--.

Column 46,
Lines 14-15, "(Zelivianskietal.," should read --(Zelivianskietal.,--.

Column 47,
Line 11, "organdies;" should read --organelles;--.

Column 50,
Line 28, "canier." should read --carrier.--.
Line 63, "Zuckennann" should read --Zuckermann--.

Column 52,
Line 40, "which hinds" should read --which binds--.
Lines 54-55, "solution.
   Examples" should read --solution. Examples--.

Column 62,
Line 63, "each tenth" should read --each term.--.

Column 63,
Line 24, "Lexington, Ky.)." should read --Lexington, KY).--.
Line 26, "HRPi Goat×Mouse" should read --HRP Goat×Mouse--.

Column 64,
Lines 50-51, "(se-29528)," should read --(sc-29528),--.
Line 51, "(se-36868)" should read --(sc-36868)--.

Column 65,
Lines 57-58, "Topsham, Me.," should read --Topsham, ME,--.

Column 70,
Line 47, "Effects of siRNA" should read --Effects of PKC-ι siRNA--.
Line 62, "O-actin" should read --β-actin--.

Column 71,
Line 21, "PKC-ε siRNA" should read --PKC-ι siRNA--.

Column 72,
Line 63, "Kuo, W-I.," should read --Kuo, W-L.,--.

CERTIFICATE OF CORRECTION (continued)
U.S. Pat. No. 8,603,758 B2

Column 73,
Line 59, "5:1 394-1403." should read --5:1394-1403.--.
Line 61, "kinase Co" should read --kinase Cδ--.

Column 74,
Line 37, "of PKC" should read --of PKCμ--.
Line 65, "resveratrol-induced" should read --reseveratrol-induced--.

Column 80,
Line 30, "determining: step" should read --determining step--.

SEQUENCE LISTING

<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: siRNA Complex

<400> SEQUENCE: 1
caagccaagc guuucaaca          19

<210> SEQ ID NO 2
<211> LENGTH: 19
<212> TYPE: RNA
<213> ORGANISM: Artificial Sequence
<220> FEATURE:
<223> OTHER INFORMATION: siRNA Complex

<400> SEQUENCE: 2
uguugaaacg cuuggcuug          19

<210> SEQ ID NO 3
<211> LENGTH: 19
<212> TYPE: RNA
<213> ORGANISM: Artificial Sequence
<220> FEATURE:
<223> OTHER INFORMATION: siRNA Complex

<400> SEQUENCE: 3
ggaacgauug gguugucau          19

<210> SEQ ID NO 4
<211> LENGTH: 20
<212> TYPE: RNA
<213> ORGANISM: Artificial Sequence
<220> FEATURE:
<223> OTHER INFORMATION: siRNA Complex

<400> SEQUENCE: 4
augacaaccc aaucguuucc          20

<210> SEQ ID NO 5
<211> LENGTH: 19
<212> TYPE: RNA
<213> ORGANISM: Artificial Sequence
<220> FEATURE:
<223> OTHER INFORMATION: siRNA Complex

<400> SEQUENCE: 5
cccaauaucu ucucuugua          19

<210> SEQ ID NO 6
<211> LENGTH: 19

```
-continued

<212> TYPE: RNA
<213> ORGANISM: Artificial Sequence
<220> FEATURE:
<223> OTHER INFORMATION: siRNA Complex

<400> SEQUENCE: 6
uacaagagaa gauauuggg                                                    19

<210> SEQ ID NO 7
<211> LENGTH: 29
<212> TYPE: RNA
<213> ORGANISM: Artificial Sequence
<220> FEATURE:
<223> OTHER INFORMATION: siRNA Complex

<400> SEQUENCE: 7
aagacgacac augucucuca cccugucuc                                         29

<210> SEQ ID NO 8
<211> LENGTH: 19
<212> TYPE: RNA
<213> ORGANISM: Artificial Sequence
<220> FEATURE:
<223> OTHER INFORMATION: siRNA Complex

<400> SEQUENCE: 8
auacauuucu acagcuagc                                                    19

<210> SEQ ID NO 9
<211> LENGTH: 29
<212> TYPE: RNA
<213> ORGANISM: Artificial Sequence
<220> FEATURE:
<223> OTHER INFORMATION: siRNA Complex

<400> SEQUENCE: 9
gagacagggu gagagacaug ugucgucuu                                         29

<210> SEQ ID NO 10
<211> LENGTH: 19
<212> TYPE: RNA
<213> ORGANISM: Artificial Sequence
<220> FEATURE:
<223> OTHER INFORMATION: siRNA Complex

<400> SEQUENCE: 10
gcuagcugua gaaauguau                                                    19

<210> SEQ ID NO 11
<211> LENGTH: 19
<212> TYPE: RNA
<213> ORGANISM: Artificial Sequence
<220> FEATURE:
<223> OTHER INFORMATION: siRNA Complex

<400> SEQUENCE: 11
ucauaaauca guuucucac                                                    19

<210> SEQ ID NO 12
<211> LENGTH: 19
<212> TYPE: RNA
<213> ORGANISM: Artificial Sequence
<220> FEATURE:
<223> OTHER INFORMATION: siRNA Complex

<400> SEQUENCE: 12
augacaaaga aauucugac                                                    19
```

```
<210> SEQ ID NO 13
<211> LENGTH: 19
<212> TYPE: RNA
<213> ORGANISM: Artificial Sequence
<220> FEATURE:
<223> OTHER INFORMATION: siRNA Complex

<400> SEQUENCE: 13
gugagaaacu gauuuauga                                              19

<210> SEQ ID NO 14
<211> LENGTH: 19
<212> TYPE: RNA
<213> ORGANISM: Artificial Sequence
<220> FEATURE:
<223> OTHER INFORMATION: siRNA Complex

<400> SEQUENCE: 14
gucagaauuu cuuugucau                                              19
```